United States Patent
Ohmoto et al.

(10) Patent No.: US 7,964,726 B2
(45) Date of Patent: Jun. 21, 2011

(54) TRICYCLIC COMPOUND AND USE THEREOF

(75) Inventors: Kazuyuki Ohmoto, Mishima-gun (JP); Masashi Kato, Mishima-gun (JP); Yoshifumi Kagamiishi, Mishima-gun (JP); Junichiro Manako, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1025 days.

(21) Appl. No.: 11/722,623

(22) PCT Filed: Dec. 21, 2005

(86) PCT No.: PCT/JP2005/023450
§ 371 (c)(1),
(2), (4) Date: Jun. 22, 2007

(87) PCT Pub. No.: WO2006/068164
PCT Pub. Date: Jun. 29, 2006

(65) Prior Publication Data
US 2008/0114012 A1     May 15, 2008

(30) Foreign Application Priority Data

Dec. 22, 2004 (JP) ................. 2004-371033
Sep. 9, 2005 (JP) ................. 2005-261914

(51) Int. Cl.
*C07D 401/04* (2006.01)
*C07D 221/06* (2006.01)
*C07D 221/20* (2006.01)
*A61K 31/4355* (2006.01)
*A61K 31/438* (2006.01)

(52) U.S. Cl. ............. 546/18; 546/79; 514/278; 514/290

(58) Field of Classification Search .............. 546/18, 546/79; 514/290, 278
See application file for complete search history.

(56) References Cited

U.S. PATENT DOCUMENTS

| | | | |
|---|---|---|---|
| 3,959,470 A | 5/1976 | Mashkovskym et al. | |
| 4,336,260 A | 6/1982 | Payne et al. | |
| 5,095,020 A | 3/1992 | Hulkenberg et al. | |
| 5,403,851 A | 4/1995 | D'Orlando et al. | |
| 6,043,252 A | 3/2000 | Bombrun | |
| 6,048,868 A | 4/2000 | Fourtillan et al. | |
| 6,350,757 B1 | 2/2002 | Goldstein et al. | |
| 7,368,444 B2 | 5/2008 | Seko et al. | |
| 7,403,851 B2 | 7/2008 | Kaufman et al. | |
| 2002/0010189 A1 | 1/2002 | Sui | |
| 2004/0072833 A1 | 4/2004 | Nakai et al. | |
| 2004/0116458 A1 | 6/2004 | Sawyer et al. | |
| 2004/0122035 A1 | 6/2004 | Orme et al. | |
| 2004/0132735 A1 | 7/2004 | Troxler et al. | |
| 2004/0147542 A1 | 7/2004 | Sawyer et al. | |
| 2004/0152736 A1 | 8/2004 | Chackalamannil et al. | |
| 2006/0154944 A1 | 7/2006 | Ohmoto et al. | |

FOREIGN PATENT DOCUMENTS

| | | |
|---|---|---|
| EP | 0740668 B1 | 7/1998 |
| EP | 1 438 973 A1 | 7/2004 |
| EP | 1 475 368 A | 11/2004 |
| FR | 1431702 | 4/1976 |
| GB | 1444980 | 8/1976 |
| JP | 3-287586 A | 12/1991 |
| JP | 09-508113 A | 8/1997 |
| JP | 9-511246 A | 11/1997 |
| JP | 2001-072679 A | 3/2001 |
| JP | 2002-517500 A | 6/2002 |
| JP | 2002-524564 A | 8/2002 |
| JP | 2004-501919 A | 1/2004 |
| JP | 2004-518729 A | 6/2004 |
| JP | 2004-518730 A | 6/2004 |
| JP | 2004-518730 A1 | 6/2004 |
| JP | 2004-532852 A | 10/2004 |
| WO | 95/26723 A1 | 10/1995 |
| WO | 97-43287 A1 | 11/1997 |
| WO | 99-64420 A1 | 12/1999 |
| WO | 00-015639 A1 | 3/2000 |

(Continued)

OTHER PUBLICATIONS

Dorwald F. A. Side Reactions in Organic Synthesis, 2005, Wiley: VCH, Weinheim p. IX of Preface.*

Limbach, M et al, Addition of Indole to methyl 2-chloro-2-cyclopropylideneacetate en route to Spirocyclopropanated Analogues or Demethoxyfumitremorgine C and Tadalafil,, Eur. J. Org. Chem., 2005, vol. 3, pp. 610 to 617.

(Continued)

*Primary Examiner* — Rita J Desai
(74) *Attorney, Agent, or Firm* — Sughrue Mion, PLLC

(57) ABSTRACT

The present invention relates to the compound represented by formula (I):

(I)

(wherein, all the symbols has the same meanings as that of the specification), a salt thereof, a solvate thereof or a prodrug thereof.

Since the compound of the present invention has an anti stress action, it is useful for preventive and/or therapeutic agent for a disease caused by stress, especially a digestive system disease caused by stress and is superior to oral absorption.

2 Claims, 1 Drawing Sheet

FOREIGN PATENT DOCUMENTS

| WO | 01-87038 A2 | 11/2001 |
|---|---|---|
| WO | 02-00657 A2 | 1/2002 |
| WO | 02-053565 A1 | 7/2002 |
| WO | 02-064590 A2 | 8/2002 |
| WO | 02-064591 A1 | 8/2002 |
| WO | 02-064591 A2 | 8/2002 |
| WO | 02-081471 A1 | 10/2002 |
| WO | 02-088123 A1 | 11/2002 |
| WO | 03-068753 A1 | 8/2003 |
| WO | 03/099821 A1 | 12/2003 |
| WO | 2004-113300 A1 | 12/2004 |
| WO | 2005/070930 A2 | 8/2005 |
| WO | 2005/089764 A1 | 9/2005 |

OTHER PUBLICATIONS

Yakhontov, L. N. et al., Azaindole derivatives,. XXXVIII. Normal and abnormal course of reactions during 12-aza-B-carboline synthesis, Khimiya Geterotsiklicheskikh Soedinenii, 1970, vol. 11, pp. 1550-1553.

Cain, M. et al., b-Carbolines: Synthesis and Neurochemical and Pharmacological actions on brain benzodiazepine receptors, J. Med. chem., 1982, vol. 25, 1081-1091.

Extended European Search Report issued in Appl. No. 05820106.2-2101/1829874, dated Dec. 3, 2009.

Chemical Abstracts Service; C. Balsamini, et al.; "N-benzhydryltryptamines and 1, 1-diphenyltetrandro-.beta.-carbolines: synthesis, x-ray crystal structure and benzodiazepine receptor affinity" XP002556789; retrieved from STN—Database accession No. 1989:526474; ISSN: 0014-827X; 1989; 2 pages in total.

International Search Report (PCT/ISA/210) for PCT/JP2004/009071, dated Oct. 5, 2004.

Manfred E. Wolff; "Burger's Medicinal Chemistry and Drug Discovery"; John Wiley & Sons, Inc., 19 vol. 1; 1995, pp. 975-977.

F. Zaragoza Dorwald; Side Reactions in Organic Synthesis, 2005; Wiley: VCH, Weinheim; p. IX of Preface.

Gilbert S. Banker; "Modern Pharmaceutics, $3^{rd}$ Edition, Revised and Expanded.", Marcel Dekker, New York, 1996, pp. 451 and 596.

European Offce Action for Application No. 04746540.6-2101 / 1637521, dated Jul. 29, 2009.

Michikazu Abe,et al.; "Reduction of Wrap Restraint Stress-Induced Defecation by MKC-242, a Novel Benzodioxan Derivative, via 5-$HT_{1A}$-Receptor Agonist Action in Rats."; Jpn. J. Pharmacol.; 1998; vol. 77; 211-217.

B. Bonaz, et al.; "Water-avoidance stress-induced *c-fos* expression in the rat brain and stimulation of fecal output: role of corticotropin-releasing factor"; 1994, Elsevier Science B.V., Brain Research, 641, pp. 21-28.

Haishan Wang, et al.; "Synthesis and Evaluation of Tryprostatin B and Demethoxyfumitremorgin C Analogues"; J. Med. Chem.; 2000 American Chemical Society, vol. 43, pp. 1577-1585.

Brian E.Love, et al.; "Preparation of I-Aryl- β-carbolines"; J. Org. Chem., 1994, vol. 59 No. 11; pp. 3219-3222.

Office Action (Non-final) issued on May 19, 2009 for U.S. Appl. No. 10/561,973.

\* cited by examiner

TRICYCLIC COMPOUND AND USE THEREOF

TECHNICAL FIELD

The present invention relates to a tricyclic heterocyclic ring compound useful for preventing and/or treating for a disease caused by stress, process for preparation thereof and use thereof.

BACKGROUND ART

A disease caused by stress means that by psychosocial or physical stress stimulation (stressor), the distortion (response to stress) in the body subjected to these stimulations occurs and any disorders in systemic various areas develop. Concretely, since stressor influences (response to stress) on the activities of nervous system, endocrine system and immune system to void these functions, these influences lead to organic lesions in brain itself or peripheral organs. In case of being subjected to excess stress, it causes diseases leading to marked reduce of quality of life (so-called, QOL).

Diseases caused by stress include, for example, central nervous system diseases (e.g. depression etc.), digestive system diseases (e.g. irritable bowel syndrome, gastric ulcer etc.), cardiovascular system diseases (e.g. essential hypertension etc.) and the like. As medicinal drugs for remedy for diseases caused by these stresses, anti depressant drug, anti anxiety drug and drug for symptomatic treatment against organic lesions of peripheral organs (e.g. antacids, gastric mucoprotective drugs etc.) have been developed for the purpose of alleviating psychological stressor. However, these drugs become effective to some extent, but these addictions, side effects or the like frequently develop. At present, the therapy for these diseases comes to definitive therapy. Therefore, the development of the preventing and/or therapeutic drug for diseases caused by stress having highly safety and coming to possible definitive therapeutic drug has been longed for.

Meanwhile, there are mitochondrial benzodiazepine receptor (hereinafter, it is abbreviated as MBR.) ("*Science* 198, 849-851, 1977", "*Proc. Natl. Acad. Sci.,* 89, 3805-3809, 1977") in mitochondrial outer membrane, which transport cholesterol from intracellular to the internal membrane of mitochondria that is the active site of P-450scc. Steroid synthesized in the brain is called as neurosteroid. Cholesterol, which is the steroid precursor, is converted into pregnenolone metabolized with side-chain cleavage enzyme P-450scc. This process is the first process of steroid production system. However, it has been indicated that this transport process was the rate-determining process in steroid production system rather than metabolism with P-450scc. It has been thought that the neurosteroid content in the brain could be adjusted if the function of MBRs could be regulated. It has been thought that as a result of balance between an excitatory signaling system and an inhibitory signaling system was collapsed by neurosteroid content in the brain varying under stress condition, the various stress-related diseases could be caused by changes of activities in nerve system, immune system and endocrine system which were regulated by these nerve systems.

As mentioned above, the disrupted balance between an excitatory signaling system and an inhibitory signaling system caused by stressor load can be improved to the desirable balanced condition by the increase or the inhibition of neurosteroid production, which is useful for prevention or treatment for stress-related diseases. Therefore, it is expected that the compounds having affinity for MBRs are extremely useful for prevention and/or treatment for these diseases, if they are supplied As the preventive and/or therapeutic agent for a disease caused by stress, the compound represented by formula (Y):

$$A^Y-X^Y-Y^Y-Z^Y-B^Y \quad (Y)$$

(wherein, $A^Y$ is cyclic group which may have a substituent(s), $X^Y, Y^Y$ and $Z^Y$ are each independently single bond or a spacer of which main chain has an atom number of 1-3, $B^Y$ is hydrocarbon which may have a substituent(s) or cyclic group which may have a substituent(s)), a salt thereof, a N-oxide thereof, a solvate thereof or a prodrug thereof is known to have the affinity to MBRs (see, WO04/113300).

In addition, as tri-cyclic compound (β-carboline derivative), the compounds represented by formula (Z):

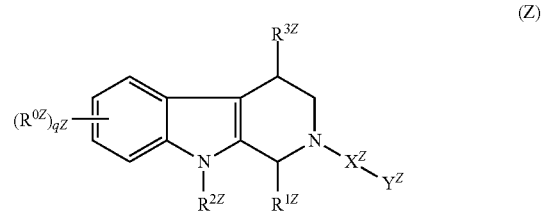

(wherein, $R^{OZ}$ is halogen atom, C1-6 alkyl etc.; $R^{1Z}$ is aryl which may be substituted etc.; $R^{2Z}$ is hydrogen atom, C1-6 alkyl etc.; $R^{3Z}$ is hydrogen atom, C1-6 alkyl, aryl etc.; $X^Z$ is C(=O), $SO_2$, C(=O)$NR^{aZ}$ etc.; Y is $(CH_2)_{nZ}$ aryl etc.; nZ is 0-4), a pharmaceutically acceptable salt thereof or a solvate thereof has been known as phosphodiesterase inhibitor (see, WO02/064591).

DISCLOSURE OF THE INVENTION

The Problems to be Solved by the Invention

As the preventive and/or therapeutic agent for a disease caused by stress, the development of the compound having anti stress effect and superior oral absorption has been longed for.

Means to Solve the Problem

As a result of the present inventors made further investigation to find out the compound having the affinity for MBRs as the preventive and/or therapeutic agent for a disease caused by stress, they found out that the compounds of the present invention represented by formula (I) had the affinity to MBRs and anti stress effect. Furthermore, they found out especially the compound of the present invention represented by formula (I-B-1-1) among the compound of the present invention represented by formula (I) shown strong anti stress effect in in vivo model and had superior oral absorption, and completed the present invention.

That is, the present invention relates to

[1] A compound represented by formula (I):

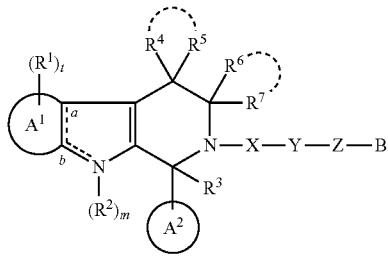

(I)

wherein $R^1$ is a hydrogen atom(s) or a substituent(s),
t is 0 or an integer of 1 to 8, when t is 2 or more, $R^1$s are same or different, two $R^1$s may together form a cyclic group which may have a substituent(s);
$R^2$, $R^3$, $R^4$, $R^5$, $R^6$ and $R^7$ are each independently a hydrogen atom(s) or a substituent(s), $R^4$ and $R^5$ and/or $R^6$ and $R^7$ may form a cyclic group which may have a substituent(s) together with their binding carbon atom;
ring $A^1$ is a monocyclic carbocyclic ring or a monocyclic heterocyclic ring;
ring $A^2$ is a cyclic group which may have a substituent(s);
B is a hydrogen atom, a hydrocarbon group which may have a substituent(s) or a cyclic group which may have a substituent(s);
X and Z are each independently a bond, C1-3 alkylene which may have a substituent(s), C2-3 alkenylene which may have a substituent(s) or C2-3 alkynylene which may have a substituent(s);
Y is a bond, —C(=O)—, —C(=S)—, —C(=O)NR$^8$—, —C(=S)NR$^8$—, —SO$_2$—, —C(=O)O— or —SO$_2$NR$^8$— group wherein X binds to a left side of each group,
$R^8$ is a hydrogen atom or a substituent;
m is 0 or 1;
⸺ is a single bond or a double bond wherein 1) a and b are not a double bond at the same time, 2) when m is 0, b is a double bond, 3) when m is 1, b is a single bond, a salt thereof, an N-oxide thereof, a solvate thereof, or a prodrug thereof,

[2] The compound according to above [1], wherein $R^4$ and $R^5$ form a cyclic group which may have a substituent(s) together with their binding carbon atom, a salt thereof, an N-oxide thereof, a solvate thereof, or a prodrug thereof,

[3] The compound according to above [1], wherein ring $A^1$ is a monocyclic heterocyclic ring, a salt thereof, an N-oxide thereof, a solvate thereof, or a prodrug thereof,

[4] The compound according to above [1], wherein ring $A^1$ is a monocyclic carbocyclic ring, a salt thereof, an N-oxide thereof, a solvate thereof, or a prodrug thereof,

[5] The compound according to above [1], wherein X is a bond, a salt thereof, an N-oxide thereof, a solvate thereof, or a prodrug thereof,

[6] The compound according to above [1], wherein Y is —C(=O)— or —C(=O)NR$^8$— wherein X binds to a left side of each group, a salt thereof, an N-oxide thereof, a solvate thereof, or a prodrug thereof,

[7] The compound according to above [1], wherein Z is a bond or C1-3 alkylene which may have a substituent(s), a salt thereof, an N-oxide thereof, a solvate thereof, or a prodrug thereof,

[8] The compound according to above [1], wherein B is C1-8 alkyl which may have a substituent(s), C3-10 monocyclic or bicyclic aromatic carbocyclic which may have a substituent(s), a carbocyclic ring which is partially or fully saturated, or 3-10 membered monocyclic or bicyclic aromatic heterocyclic ring which may be partially or fully saturated, and which contains 1 to 4 hetero atom(s) selected from an oxygen atom, a nitrogen atom and/or a sulfur atom, a salt thereof, an N-oxide thereof, a solvate thereof, or a prodrug thereof,

[9] The compound according to above [1], which is a compound represented by formula (I-A):

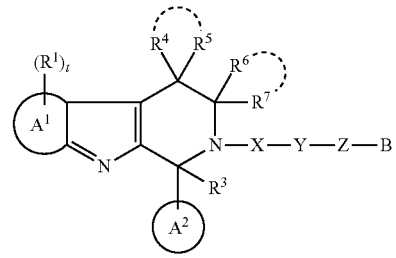

(I-A)

wherein all the symbols have the same meanings as described in [1], a salt thereof, an N-oxide thereof, a solvate thereof, or a prodrug thereof,

[10] The compound according to above [9], which is a compound represented by formula (I-A-1):

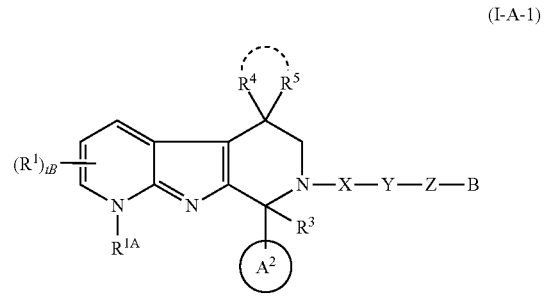

(I-A-1)

wherein $R^{1A}$ has the same meaning as $R^1$;
tB is 0 or an integer of 1 to 3, when tB is 2 or more, R's are same or different;
other symbols have the same meanings as described in above [1],
a salt thereof, an N-oxide thereof, a solvate thereof, or a prodrug thereof,

[11] The compound according to above [1], which is a compound represented by formula (I-B-1):

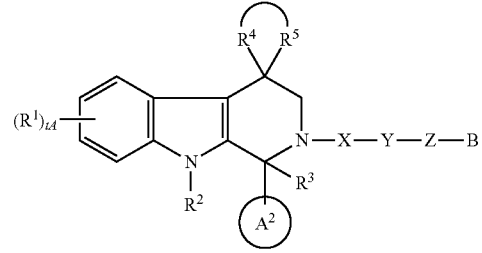

(I-B-1)

wherein tA is 0 or an integer of 1 to 4, when tA is 2 or more, R¹s are same or different;

R⁴ and R⁵ form cyclic group which may have a substituent(s) together with their binding carbon atom;

other symbols have the same meanings as described in above [1], a salt thereof, an N-oxide thereof, a solvate thereof, or a prodrug thereof,

[12] The compound according to above [1], which is a compound represented by formula (I-B-2):

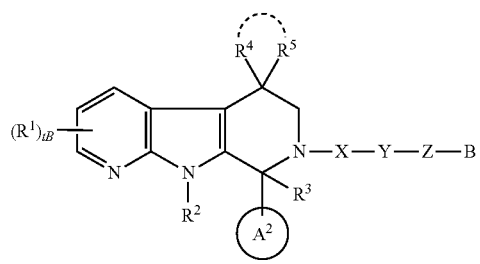

(I-B-2)

wherein all symbols have the same meaning as described in above [1] or [10], a salt thereof, an N-oxide thereof, a solvate thereof, or a prodrug thereof,

[13] The compound according to above [11], which is a compound represented by formula (I-B-1-1):

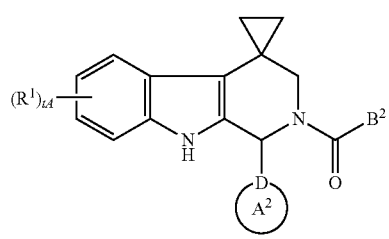

(I-B-1-1)

wherein B² is C1-8 alkyl which may have a substituent(s);

D is an atom which constitutes ring A² and is a carbon atom or a nitrogen atom,

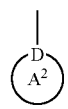

is a cyclic group which has at least two same or different substituents;

other symbols have the same meanings as described in above [1] or [11], a salt thereof, an N-oxide thereof, a solvate thereof, or a prodrug thereof,

[14] The compound according to above [13], wherein

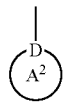

is a cyclic group which has two same or different substituents, a salt thereof, an N-oxide thereof, a solvate thereof, or a prodrug thereof,

[15] The compound according to above [14], wherein one substituent on ring A² is (1) C1-8 alkoxy which may have a substituent(s), or (2) C3-7 cycloalkyloxy which may have a substituent(s);

the other substituent is selected from (1) a halogen atom, (2) cyano, (3) C1-8 alkyl which may have a substituent(s) and (4) C1-8 alkoxy which may have a substituent(s), a salt thereof, an N-oxide thereof, a solvate thereof, or a prodrug thereof,

[16] The compound according to above [15], wherein one substituent on ring A² is selected from (1) methoxy which may have a fluorine atom(s), (2) isopropoxy which may have a fluorine atom(s), (3) cyclopentyloxy which may have a fluorine atom(s);

the other substituent is selected from (1) a fluorine atom, (2) a chlorine atom, (3) cyano, (4) methyl, and (5) methoxy which may have a fluorine atom(s), a salt thereof, an N-oxide thereof, a solvate thereof, or a prodrug thereof,

[17] The compound according to above [14], wherein the cyclic group represented by

is a benzene ring, a salt thereof, an N-oxide thereof, a solvate thereof, or a prodrug thereof,

[18] The compound according to above [13], wherein one substituent is substituted to an atom neighboring D, a salt thereof, an N-oxide thereof, a solvate thereof, or a prodrug thereof,

[19] The compound according to above [13], which is a compound represented by formula (I-B-1-1-a):

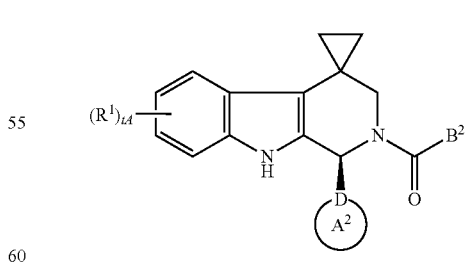

(I-B-1-1-a)

wherein ∕ is β-configuration and other symbols have the same meanings as described in above [13], a salt thereof, an N-oxide thereof, a solvate thereof, or a prodrug thereof,

[20] The compound according to above [14], which is a compound represented by formula (I-B-1-2):

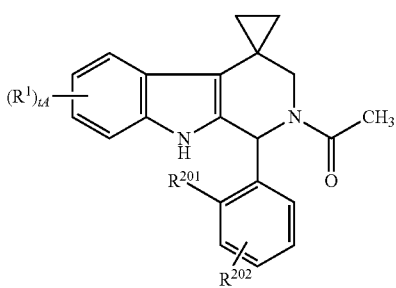

(I-B-1-2)

wherein R²⁰¹ is C1-8 alkoxy which may have a substituent(s) or C3-7 cycloalkyl which may have a substituent(s);

R²⁰² is a halogen atom, cyano, C1-8 alkyl which may have a substituent(s) or C1-8 alkoxy which may have a substituent(s);

other symbols have the same meanings as described in above [11], a salt thereof, an N-oxide thereof, a solvate thereof, or a prodrug thereof,

[21] The compound according to above [20], which is a compound represented by formula (I-B-1-2-a):

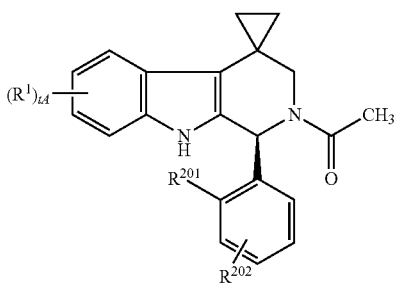

(I-B-1-2-a)

wherein all symbols have the same meanings as described in above [11], [19] or [20], a salt thereof, an N-oxide thereof, a solvate thereof, or a prodrug thereof,

[22] The compound according to above [20] or [21], wherein R²⁰¹ is selected from (1) methoxy which may have a fluorine atom(s), (2) isopropoxy which may have a fluorine atom(s), and (3) cyclopentyloxy which may have a fluorine atom(s);

R²⁰² is selected from (1) a fluorine atom, (2) a chlorine atom, (3) cyano, (4) methyl, and (5) methoxy which may have a fluorine atom(s), a salt thereof, an N-oxide thereof, a solvate thereof, or a prodrug thereof

[23] The compound according to above [1], which is
(1) 1-(1,3-benzodioxol-5-yl)-N-(3,5-dimethylphenyl)-1,9-dihydrospiro[β-carboline-4,1'-cyclopropane]-2(3H)-carboxamide,
(2) 2-acetyl-1-(2,4-difluorophenyl)-1,2,3,9-tetrahydrospiro[β-carboline-4,1'-cyclopropane],
(3) 2-acetyl-1-(3,4-difluorophenyl)-1,2,3,9-tetrahydrospiro[β-carboline-4,1'-cyclopropane],
(4) 2-acetyl-1-(3-fluorophenyl)-6-methoxy-1,2,3,9-tetrahydrospiro[β-carboline-4,1'-cyclopropane],
(5) 2-acetyl-6-fluoro-1-(3-fluorophenyl)-1,2,3,9-tetrahydrospiro[β-carboline-4,1'-cyclopropane],
(6) 2-acetyl-1-(2,4-difluorophenyl)-6-fluoro-1,2,3,9-tetrahydrospiro[β-carboline-4,1'-cyclopropane],
(7) 2-acetyl-1-(3,4-difluorophenyl)-6-fluoro-1,2,3,9-tetrahydrospiro[β-carboline-4,1'-cyclopropane],
(8) 2-acetyl-1-(3-fluorophenyl)-7-methoxy-1,2,3,9-tetrahydrospiro[β-carboline-4,1'-cyclopropane],
(9) 2-acetyl-7-fluoro-1-(3-fluorophenyl)-1,2,3,9-tetrahydrospiro[β-carboline-4,1'-cyclopropane],
(10) 2-acetyl-1-(3-fluorophenyl)-5-methoxy-1,2,3,9-tetrahydrospiro[β-carboline-4,1'-cyclopropane],
(11) 1-(2,6-difluorophenyl)-N-(3,5-dimethylphenyl)-1,9-dihydrospiro[β-carboline-4,1'-cyclopropane]-2(3H)-carboxamide,
(12) 1-(3,5-difluorophenyl)-N-(3,5-dimethylphenyl)-1,9-dihydrospiro[β-carboline-4,1'-cyclopropane]-2(3H)-carboxamide,
(13) 1-(2,4-difluorophenyl)-N-(3,5-dimethylphenyl)-1,9-dihydrospiro[β-carboline-4,1'-cyclopropane]-2(3H)-carboxamide,
(14) 1-(2,3-difluorophenyl)-N-(3,5-dimethylphenyl)-1,9-dihydrospiro[β-carboline-4,1'-cyclopropane]-2(3H)-carboxamide,
(15) 1-(2,5-difluorophenyl)-N-(3,5-dimethylphenyl)-1,9-dihydrospiro[β-carboline-4,1'-cyclopropane]-2(3H)-carboxamide,
(16) 1-(3,4-difluorophenyl)-N-(3,5-dimethylphenyl)-1,9-dihydrospiro[β-carboline-4,1'-cyclopropane]-2(3H)-carboxamide,
(17) 6-chloro-N-(3,5-dimethylphenyl)-1-(3-fluorophenyl)-1,9-dihydrospiro[β-carboline-4,1'-cyclopropane]-2(3H)-carboxamide,
(18) N-(3,5-dimethylphenyl)-1-(3-fluorophenyl)-6-methoxy-1,9-dihydrospiro[β-carboline-4,1'-cyclopropane]-2(3H)-carboxamide,
(19) 2-acetyl-1-(3-fluorophenyl)-6,7-dimethoxy-1,2,3,9-tetrahydrospiro[β-carboline-4,1'-cyclopropane],
(20) 2-acetyl-1-(2,4-difluorophenyl)-6,7-dimethoxy-1,2,3,9-tetrahydrospiro[β-carboline-4,1'-cyclopropane],
(21) 2-acetyl-1-(2,4-difluorophenyl)-7-fluoro-1,2,3,9-tetrahydrospiro[β-carboline-4,1'-cyclopropane],
(22) 2-acetyl-1-(3,4-difluorophenyl)-7-fluoro-1,2,3,9-tetrahydrospiro[β-carboline-4,1'-cyclopropane],
(23) 2-acetyl-5-fluoro-1-(3-fluorophenyl)-1,2,3,9-tetrahydrospiro[β-carboline-4,1'-cyclopropane],
(24) 2-acetyl-1-(2,4-difluorophenyl)-5-fluoro-1,2,3,9-tetrahydrospiro[β-carboline-4,1'-cyclopropane],
(25) 2-acetyl-1-(3,4-difluorophenyl)-5-fluoro-1,2,3,9-tetrahydrospiro[β-carboline-4,1'-cyclopropane],
(26) 2-acetyl-1-(3-fluorophenyl)-8-methoxy-1,2,3,9-tetrahydrospiro[β-carboline-4,1'-cyclopropane],
(27) 2-acetyl-1-(2,4-difluorophenyl)-8-methoxy-1,2,3,9-tetrahydrospiro[β-carboline-4,1'-cyclopropane],
(28) 2-acetyl-1-(3,4-difluorophenyl)-8-methoxy-1,2,3,9-tetrahydrospiro[β-carboline-4,1'-cyclopropane],
(29) 2-acetyl-1-(3-fluorophenyl)-6,8-dimethoxy-1,2,3,9-tetrahydrospiro[β-carboline-4,1'-cyclopropane],
(30) 2-acetyl-1-(3,4-difluorophenyl)-6,8-dimethoxy-1,2,3,9-tetrahydrospiro[β-carboline-4,1'-cyclopropane],
(31) 8-(2,2-difluoro-1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide,
(32) N-(3,5-dimethylphenyl)-8'-(3-fluorophenyl)-1',8'-dihydrospiro[cyclopropane-1,5'-pyrido[4',3':4,5]pyrrolo[2,3-b]pyridine]-7'(6H)-carboxamide,
(33) N-(3,5-dimethylphenyl)-8-(3-fluorophenyl)-9-methyl-5,6,8,9-tetrahydro-7H-pyrido[4',3':4,5]pyrrolo[2,3-b]pyridine-7-carboxamide,

(34) N-(3,5-dimethylphenyl)-8-(3-fluorophenyl)-1-methyl-1,5,6,8-tetrahydro-7H-pyrido[4',3':4,5]pyrrolo[2,3-b]pyridine-7-carboxamide,

(35) N-(3,5-dimethylphenyl)-6-(3-fluorophenyl)-5,6,8,9-tetrahydro-7H-pyrido[3',4':4,5]pyrrolo[2,3-c]pyridine-7-carboxamide,

(36) 7-acetyl-6-(3-fluorophenyl)-6,7,8,9-tetrahydro-5H-pyrido[3',4':4,5]pyrrolo[2,3-c]pyridine,

(37) N-(3,5-dimethylphenyl)-8'-(3-fluorophenyl)-1'-methyl-1',8'-dihydrospiro[cyclopropane-1,5'-pyrido[4',3':4,5]pyrrolo[2,3-b]pyridine]-7'(6'H)-carboxamide,

(38) 7'-acetyl-8'-(3-fluorophenyl)-1'-methyl-1',6',7',8'-tetrahydrospiro[cyclopropane-1,5'-pyrido[4',3':4,5]pyrrolo[2,3-b]pyridine,

(39) N-(3,5-dimethylphenyl)-8-(3-methoxyphenyl)-1-methyl-1,5,6,8-tetrahydro-7H-pyrido[4',3':4,5]pyrrolo[2,3-b]pyridine-7-carboxamide,

(40) 8-(2,2-difluoro-1,3-benzodioxol-5-yl)-N-(3,5-dimethylphenyl)-1-methyl-1,5,6,8-tetrahydro-7H-pyrido[4',3':4,5]pyrrolo[2,3-b]pyridine-7-carboxamide,

(41) N-(3,5-dimethylphenyl)-6-(3-fluorophenyl)-2-methoxy-5,6,8,9-tetrahydro-7H-pyrido[4',3':4,5]pyrrolo[3,2-b]pyridine-7-carboxamide,

(42) 2-chloro-N-(3,5-dimethylphenyl)-6-(3-fluorophenyl)-5,6,8,9-tetrahydro-7H-pyrido[4',3':4,5]pyrrolo[3,2-b]pyridine-7-carboxamide,

(43) N-(3,5-dimethylphenyl)-6-(3-fluorophenyl)-5,6,8,9-tetrahydro-7H-pyrido[4',3':4,5]pyrrolo[3,2-b]pyridine-7-carboxamide,

(44) 7-acetyl-2-chloro-6-(3-fluorophenyl)-6,7,8,9-tetrahydro-5H-pyrido[4',3':4,5]pyrrolo[3,2-b]pyridine,

(45) 7-acetyl-6-(3-fluorophenyl)-6,7,8,9-tetrahydro-5H-pyrido[4',3':4,5]pyrrolo[3,2-b]pyridine,

(46) 2-ethyl-1-(3-fluorophenyl)-1,2,3,9-tetrahydrospiro[β-carboline-4,1'-cyclopropane],

(48) 2-acetyl-5-methoxy-1-(2-methoxyphenyl)-1,2,3,9-tetrahydrospiro[β-carboline-4,1'-cyclopropane], or

(49) 4-(2-acetyl-5-methoxy-1,2,3,9-tetrahydrospiro[β-carboline-4,1'-cyclopropane]-1-yl)benzonitrile, a salt thereof, an N-oxide thereof, a solvate thereof, or a prodrug thereof,

[24] The compound as according to above [1,3], which is (1) 2-acetyl-1-(4-chloro-2-methoxyphenyl)-1,2,3,9-tetrahydrospiro[β-carboline-4,1'-cyclopropane], (2) 2-acetyl-1-(4-chloro-2-methoxyphenyl)-5-fluoro-1,2,3,9-tetrahydrospiro[β-carboline-4,1'-cyclopropane], (3) 2-acetyl-1-(4-chloro-2-methoxyphenyl)-5,6-difluoro-1,2,3,9-tetrahydrospiro[β-carboline-4,1'-cyclopropane], (4) 2-acetyl-1-(4-chloro-2-methoxyphenyl)-6-fluoro-1,2,3,9-tetrahydrospiro[β-carboline-4,1'-cyclopropane], (5) 2-acetyl-1-(4-chloro-2-methoxyphenyl)-5-methoxy-1,2,3,9-tetrahydrospiro[β-carboline-4,1'-cyclopropane], (6) 2-acetyl-5-chloro-1-(4-chloro-2-methoxyphenyl)-1,2,3,9-tetrahydrospiro[β-carboline-4,1'-cyclopropane], (7) 2-acetyl-5-chloro-1-(2-methoxy-4-methylphenyl)-1,2,3,9-tetrahydrospiro[β-carboline-4,1'-cyclopropane], (8) 2-acetyl-5-fluoro-1-(2-fluoro-6-methoxyphenyl)-1,2,3,9-tetrahydrospiro[β-carboline-4,1'-cyclopropane], (9) 2-acetyl-6-fluoro-1-(4-fluoro-2-methoxyphenyl)-1,2,3,9-tetrahydrospiro[β-carboline-4,1'-cyclopropane],

(10) 2-acetyl-5-fluoro-1-(4-fluoro-2-methoxyphenyl)-1,2,3,9-tetrahydrospiro[β-carboline-4,1'-cyclopropane],

(11) 2-acetyl-1-(5-fluoro-2-methoxyphenyl)-5-methoxy-1,2,3,9-tetrahydrospiro[β-carboline-4,1'-cyclopropane],

(12) 2-acetyl-1-(4-fluoro-2-methoxyphenyl)-5-methoxy-1,2,3,9-tetrahydrospiro[β-carboline-4,1'-cyclopropane],

(13) 2-acetyl-1-(2,4-dimethoxyphenyl)-5-methoxy-1,2,3,9-tetrahydrospiro[β-carboline-4,1'-cyclopropane]

(14) 2-acetyl-1-(2-fluoro-6-methoxyphenyl)-5-methoxy-1,2,3,9-tetrahydrospiro[β-carboline-4,1'-cyclopropane],

(15) 2-acetyl-1-(4-chloro-2-methoxyphenyl)-6,7-dimethoxy-1,2,3,9-tetrahydrospiro[β-carboline-4,1'-cyclopropane],

(16) 2-acetyl-1-(2-methoxy-4-methylphenyl)-1,2,3,9-tetrahydrospiro[β-carboline-4,1'-cyclopropane],

(17) 2-acetyl-5-fluoro-1-(2-methoxy-4-methylphenyl)-1,2,3,9-tetrahydrospiro[β-carboline-4,1'-cyclopropane],

(18) 2-acetyl-1-(4-chloro-2-methoxyphenyl)-6-methoxy-1,2,3,9-tetrahydrospiro[β-carboline-4,1'-cyclopropane],

(19) 2-acetyl-1-(4-fluoro-2-methoxyphenyl)-6-methoxy-1,2,3,9-tetrahydrospiro[β-carboline-4,1'-cyclopropane],

(20) 2-acetyl-6-methoxy-1-(2-methoxy-4-methylphenyl)-1,2,3,9-tetrahydrospiro[β-carboline-4,1'-cyclopropane],

(21) 2-acetyl-1-(2-fluoro-6-methoxyphenyl)-6-methoxy-1,2,3,9-tetrahydrospiro[β-carboline-4,1'-cyclopropane],

(22) 2-acetyl-6,7-dimethoxy-1-(2-methoxy-4-methylphenyl)-1,2,3,9-tetrahydrospiro[β-carboline-4,1'-cyclopropane],

(23) 2-acetyl-1-(4-chloro-2-methoxyphenyl)-5-methyl-1,2,3,9-tetrahydrospiro[β-carboline-4,1'-cyclopropane],

(24) 2-acetyl-1-(2-methoxy-4-methylphenyl)-5-methyl-1,2,3,9-tetrahydrospiro[β-carboline-4,1'-cyclopropane],

(25) 2-acetyl-1-(2,3-dihydro-1-benzofuran-7-yl)-6-methoxy-1,2,3,9-tetrahydrospiro[β-carboline-4,1'-cyclopropane],

(26) 2-acetyl-1-(4-chloro-2-methoxyphenyl)-6-methoxy-5-methyl-1,2,3,9-tetrahydrospiro[β-carboline-4,1'-cyclopropane],

(27) 2-acetyl-1-(4-chloro-2-methoxyphenyl)-5,6-dimethoxy-1,2,3,9-tetrahydrospiro[β-carboline-4,1'-cyclopropane],

(28) (1S)-2-acetyl-1-(4-chloro-2-methoxyphenyl)-5-fluoro-1,2,3,9-tetrahydrospiro[β-carboline-4,1'-cyclopropane],

(29) (−)-2-acetyl-1-(4-chloro-2-methoxyphenyl)-5,6-difluoro-1,2,3,9-tetrahydrospiro[β-carboline-4,1'-cyclopropane],

(30) (+)-2-acetyl-1-(4-chloro-2-methoxyphenyl)-5,6-difluoro-1,2,3,9-tetrahydrospiro[β-carboline-4,1'-cyclopropane],

(31) (+)-2-acetyl-1-(4-chloro-2-methoxyphenyl)-5-methoxy-1,2,3,9-tetrahydrospiro[β-carboline-4,1'-cyclopropane],

(32) (+)-2-acetyl-1-(2-fluoro-6-methoxyphenyl)-5-methoxy-1,2,3,9-tetrahydrospiro[β-carboline-4,1'-cyclopropane],

(33) (+)-2-acetyl-5-fluoro-1-(2-fluoro-6-methoxyphenyl)-1,2,3,9-tetrahydrospiro[β-carboline-4,1'-cyclopropane],

(34) (+)-2-acetyl-1-(4-chloro-2-methoxyphenyl)-6,7-dimethoxy-1,2,3,9-tetrahydrospiro[β-carboline-4,1'-cyclopropane],

(35) 2-acetyl-5-chloro-1-(4-fluoro-2-methoxyphenyl)-1,2,3,9-tetrahydrospiro[β-carboline-4,1'-cyclopropane],

(36) 2-acetyl-5,6-difluoro-1-(4-fluoro-2-methoxyphenyl)-1,2,3,9-tetrahydrospiro[β-carboline-4,1'-cyclopropane],

(37) 2-acetyl-5,6-difluoro-1-(2-methoxy-4-methylphenyl)-1,2,3,9-tetrahydrospiro[β-carboline-4,1'-cyclopropane],

(38) 2-acetyl-5-chloro-1-(2-fluoro-6-methoxyphenyl)-1,2,3,9-tetrahydrospiro[β-carboline-4,1'-cyclopropane],

(39) 2-acetyl-1-(4-chloro-2-isopropoxyphenyl)-1,2,3,9-tetrahydrospiro[β-carboline-4,1'-cyclopropane],

(40) 2-acetyl-1-[4-chloro-2-(cyclopentyloxy)phenyl]-1,2,3,9-tetrahydrospiro[β-carboline-4,1'-cyclopropane],

(41) 4-(2-acetyl-1,2,3,9-tetrahydrospiro[β-carboline-4,1'-cyclopropane]-1-yl)-3-methoxybenzonitrile,
(42) 2-acetyl-1-(4-chloro-2-methoxyphenyl)-5,7-difluoro-1,2,3,9-tetrahydrospiro[β-carboline-4,1'-cyclopropane],
(43) 2-acetyl-1-(4-chloro-2-methoxyphenyl)-8-fluoro-1,2,3,9-tetrahydrospiro[β-carboline-4,1'-cyclopropane],
(44) 4-(2-acetyl-5-fluoro-1,2,3,9-tetrahydrospiro[β-carboline-4,1'-cyclopropane]-1-yl)-3-methoxybenzonitrile,
(45) 2-acetyl-5,6-dimethoxy-1-(2-methoxy-4-methylphenyl)-1,2,3,9-tetrahydrospiro[β-carboline-4,1'-cyclopropane],
(46) 2-acetyl-1-(2,3-dihydro-1-benzofuran-7-yl)-5-methoxy-1,2,3,9-tetrahydrospiro[β-carboline-4,1'-cyclopropane],
(47) 2-acetyl-5-methoxy-1-(2-methoxy-4-methylphenyl)-1,2,3,9-tetrahydrospiro[β-carboline-4,1'-cyclopropane],
(48) 2-acetyl-1-(4-chloro-2-methoxyphenyl)-6,8-dimethoxy-1,2,3,9-tetrahydrospiro[β-carboline-4,1'-cyclopropane],
(49) 2-acetyl-6-chloro-1-(4-chloro-2-methoxyphenyl)-1,2,3,9-tetrahydrospiro[β-carboline-4,1'-cyclopropane],
(50) 2-acetyl-1-(4-chloro-2-methoxyphenyl)-5-fluoro-8-methoxy-1,2,3,9-tetrahydrospiro[β-carboline-4,1'-cyclopropane],
(51) 2-acetyl-5-fluoro-1-(4-fluoro-2-methoxyphenyl)-8-methoxy-1,2,3,9-tetrahydrospiro[β-carboline-4,1'-cyclopropane],
(52) (+)-2-acetyl-1-(2-fluoro-6-methoxyphenyl)-6-methoxy-1,2,3,9-tetrahydrospiro[β-carboline-4,1'-cyclopropane],
(53) (+)-2-acetyl-1-(2-methoxy-4-methylphenyl)-5-methyl-1,2,3,9-tetrahydrospiro[β-carboline-4,1'-cyclopropane],
(54) (+)-2-acetyl-1-(4-chloro-2-methoxyphenyl)-6-methoxy-5-methyl-1,2,3,9-tetrahydrospiro[β-carboline-4,1'-cyclopropane],
(55) (+)-2-acetyl-5-fluoro-1-(4-fluoro-2-methoxyphenyl)-1,2,3,9-tetrahydrospiro[β-carboline-4,1'-cyclopropane],
(56) (+)-2-acetyl-5,6-difluoro-1-(2-methoxy-4-methylphenyl)-1,2,3,9-tetrahydrospiro[β-carboline-4,1'-cyclopropane], or
(57) (+)-2-acetyl-5-chloro-1-(4-chloro-2-methoxyphenyl)-1,2,3,9-tetrahydrospiro[β-carboline-4,1'-cyclopropane],
a salt thereof, an N-oxide thereof, a solvate thereof, or a prodrug thereof,

[25] A pharmaceutical composition comprising the compound represented by formula (I) described in above [1], a salt thereof, an N-oxide thereof, a solvate thereof, or a prodrug thereof,

[26] The pharmaceutical composition according to above [25], which is an agent for preventing and/or treating a disease caused by stress,

[27] The pharmaceutical composition according to above [26], wherein the disease caused by stress is a digestive system disease caused by stress,

[28] The pharmaceutical composition according to above [27], wherein the digestive system disease caused by stress is irritable bowel syndrome, ulcerative colitis, or Crohn's disease,

[29] A pharmaceutical composition comprising the compound represented by formula (I) described in above [1], a salt thereof, an N-oxide thereof, a solvate thereof, or a prodrug thereof and one or more kind of agents selected from an antianxiety, an antidepressant, an anticholinergic, a gastrointestinal tract function regulator, a gastrointestinal tract prokinetic drug, an antidiarrheal, an evacuant, a calcium antagonist, a phosphodiesterase inhibitor and a serotonin antagonist in combination,

[30] A method for preventing and/or treating a disease caused by stress in a mammal comprising administering an effective amount of the compound represented by formula (I) described in above [1], a salt thereof, an N-oxide, a solvate or a prodrug thereof to the mammal,

[31] Use of the compound represented by formula (I) according to above [1], a salt thereof, an N-oxide thereof, a solvate thereof or a prodrug thereof for preparing an agent for preventing and/or treating a disease caused by stress, and so on.

In the specification, a disease caused by stress is a general term of a disease developed by psychological or physical stressor and includes all diseases known so called psychosomatic disorders. It includes, concretely, central nervous system diseases caused by stress, respiratory system diseases caused by stress, digestive system diseases caused by stress, cardiovascular system diseases caused by stress, uropathy/reproductive system diseases caused by stress, gynecologic diseases caused by stress, endocrine/metabolic diseases caused by stress, opthalmologic diseases caused by stress, otolaryngological diseases caused by stress, dental surgery/dentistry diseases caused by stress, surgical/orthopedic diseases caused by stress, skin diseases caused by stress, other diseases caused by stress and so on. It preferably includes, central nervous system diseases caused by stress, respiratory system diseases caused by stress and/or digestive system diseases caused by stress. It more preferably includes digestive system diseases caused by stress.

In the specification, central nervous system diseases caused by stress include, for example, anxiety related disease, neurosis, panic disorder, sleep disorder, depression, reactive depression, epilepsy, Parkinson's disease, Perkinsonian syndrome, schizophrenia, autonomic dystonia, Huntington's disease, Alzheimer's disease, affective disorder, cognitive disorder, migraine, tension headache, cluster headache, posttraumatic stress disorder (PTSD), dissociative disorder, insomnia, nervous cough, psychogenic convulsive seizure, psychogenic syncopal attack, maladjustment to job, burn-out syndrome, chronic fatigue syndrome, writer's cramp, spastic torticollis and so on. They preferably include anxiety related disease, sleep disorder, depression and/or epilepsy.

In the specification, respiratory system diseases caused by stress include, for example, asthma, bronchial asthma, hyperventilation syndrome, laryngeal spasm, chronic obstructive pulmonary diseases and so on. They preferably include asthma.

In the specification, digestive system diseases caused by stress include, for example, irritable bowel syndrome, peptic ulcer, functional dyspepsia, gastric ulcer, duodenal ulcer, biliary tract dyskinesia, esophageal spasm, gastric atony, aerophagy, chronic gastritis, chronic hepatitis, chronic pancreatitis, eating disorder (e.g. neurogenic emaciation, anorexia, bulimia etc.), nervous (psychogenic) vomiting, nervous (psychogenic) nausea, inflammatory bowel disease (e.g. ulcerative colitis, Crohn's disease), abdominal tense syndrome, gastrointestinal neurosis (e.g. borborygmus-phobia etc.) and so on. They preferably include irritable bowel syndrome, ulcerative colitis, Crohn's disease.

In the specification, cardiovascular system diseases caused by stress include, for example, essential hypertension, arrhythmia, (neurological) angina pectoris, essential hypotension, orthostatic dysregulation, myocardial infarction, arteriosclerosis, vertigo and so on. They preferably include essential hypertension, arrhythmia and/or angina pectoris.

In the specification, uropathy/reproductive system diseases caused by stress include, for example, dysuria, nervous pollakisuria (hyperreflexic bladder), nocturia, enuresis, psychogenic ischuria, impotentia, prostatism, urethral syndrome and so on. They preferably include dysuria.

In the specification, gynecologic disorder caused by stress include, for example, menopausal disorder, menstrual pain, amenorrhea, menstrual disorder, premenstrual syndrome, infertility, frigidity, serious vomiting of pregnancy, abortion, immature birth, functional metrorrhagia and so on.

In the specification, endocrine/metabolic diseases caused by stress include, for example, Bartter's syndrome, hyperthyroidism, glucose metabolism disorder (e.g. diabetes, (reflex) hypoglycemia etc.), lipid metabolism disorder (e.g. hyperlipidemia etc.), gout, osteoporosis, hypothalamus disease, pituitarium disease, parathyroid disease, adrenal cortex/adrenal medulla disease, gonadal disease, psychogenic polydipsia, adiposity and so on.

In the specification, opthalmologic diseases caused by stress include, for example, asthenopia, central retinitis, floaters, blepharospasm, primary glaucoma, vertigo, eye hysteria and so on.

In the specification, otolaryngological diseases caused by stress include, for example, tinnitus, vertigo, psychogenic deafness, chronic sinusitis, allergic rhinitis, smell disorder, stuttering, anaudia, Meniere's disease, laryngopharynx discomfort, kinetosis, trachyphonia and so on.

In the specification, dental surgery/dentistry diseases caused by stress include, for example, temporomandibular arthrosis, glossopharyngeal neuralgia, sudden glossodynia, stomatitis, toothache, ozostomia, abnormal salivation, bruxism and so on.

In the specification, surgical/orthopedic diseases caused by stress include, for example, postoperative abdominal neurosis, dumping syndrome, polysurgery, plastic postoperative neurosis, rheumatoid arthritis, low back pain, cervico-omobrachial syndrome, stiff neck, fibrositis, polyarthralgia, systemic myalgia, gout, spinal irritation, tic and so on.

In the specification, skin diseases caused by stress include, for example, chronic urticaria, atopic dermatitis, hyperhidrosis, eczema, skin pruritus, alopecia areata and so on.

In the specification, other diseases caused by stress include, for example, cancer, systemic lupus erythematosus and so on.

In the specification, anxiety related diseases include, for example, neurosis, generalized anxiety disorder (GAD), social-anxiety disorder (SAD), panic disorder, hyperactivity disorder, attention-deficit, personality disorder, bipolar disorder, autism and so on.

In the specification, cyclic group in "cyclic group which may have a substituent(s)" represented by ring $A^2$ includes, for example, carbocyclic ring, heterocyclic ring and so on.

Said carbocyclic ring includes, for example, C3-20 mono-, bi-, tri- or tetra-aromatic carbocyclic ring partially or fully saturated, spiro-linked bi-, tri-, or tetra-carbocyclic ring, and bridged bi-, tri-, or tetra-carbocyclic ring and so on.

Said C3-20 mono-, bi-, tri- or tetra-aromatic carbocyclic ring partially or fully saturated means, for example, benzene, azulene, naphthalene, phenanthrene, anthracene, triphenylene, chrysene, naphthacene, pleiadene, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, fluoranthene, acephenanthrylene, aceanthrylene, pyrene and so on.

Said spiro-linked bi-, tri-, or tetra-carbocyclic ring, and bridged bi-, tri-, or tetra-carbocyclic ring mean, for example, spiro[4.4]nonane, spiro[4.5]decane, spiro[5.5]undecane, bicyclo[2.2.1]heptane, bicyclo[2.2.1]hepta-2-ene, bicyclo[3.1.1]heptane, bicyclo[3.1.1]hepta-2-ene, bicyclo[2.2.2]octane, bicyclo[2.2.2]octa-2-ene, adamantane, noradamantane and so on.

Said heterocyclic ring includes, for example, 3-20 membered mono-, bi-, tri-, or tetra-aromatic heterocyclic ring optionally partially or fully saturated containing 1 to 5 hetero atom(s) selected from oxygen, nitrogen and sulfur atom(s) and so on.

Said 3-20 membered mono-, bi-, tri-, or tetra-aromatic heterocyclic ring optionally partially or fully saturated containing 1 to 5 hetero atom(s) selected from oxygen, nitrogen and sulfur atom(s) includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, pyridonaphthyridine, pyrazoloisoquinoline, pyrazolonaphthyridine, pyrimidoindole, indolizinoindole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydro furan, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, tetrapyridonaphthyridine, tetrahydro-β-carboline (e.g. 2,3,4,9-tetrahydro-1H-β-carboline etc.), tetrahydropyridopyrrolopyridine (e.g. 6,7,8,9-tetrahydro-5H-pyrido[4',3':4,5]pyrrolo[2,3-b]pyridine, 2,3,4,9-tetrahydro-1H-pyrido[4',3':4,5]pyrrolo[2,3-c]pyridine, 6,7,8,9-tetrahydro-5H-pyrido[3',4':4,5]pyrrolo[2,3-c]pyridine, 6,7,8,9-tetrahydro-5H-pyrido[4',3':4,5]pyrrolo[3,2-b]pyridine etc.), 6,7,8,9-tetrahydro-5H-pyrido[4',3':4,5]pyrrolo[2,3-d]pyrimidine, dihydroazepinoindole, hexahydroazepinoindole (e.g. 1,2,3,4,5,10-hexahydroazepino[3,4-b]indole, 1,2,3,4,5,6-hexahydroazepino[4,3-b]indole etc.), tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydrooxazinoindole, hexahydroindolizinoindole, dihydroindolobenzdiazepine, octahydroindoloquinolizine, hexahydroimidazopyridoindole, hexahydropyrrolothiazepinoindole, dioxolane, dioxane, dithiolane, dithiane, dioxaindan, benzodioxane, chroman, benzodithiolane, benzodithiane, azaspiro[4.4]nonane, oxazaspiro[4.4]nonane, oxazaspiro[2.5]octane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,3,4,9-tetrahydrospiro[β-carboline-1,1'-cyclopentane], 1,2,3,9-tetrahydrospiro[β-carboline-4,1'-cyclopropane], 1,2,4,9-tetrahydrospiro[β-carboline-3,1'-cyclopropane], 1,2,3,9-tetrahydrospiro[β-carboline-4,1'-cyclobutane], 1,2,4,9-tetrahydrospiro[β-carboline-3,1'-cyclobutane], 1,2,3,9-tetrahydrospiro[β-carboline-4,1'-cyclopentane], 1,2,4,9-tetrahydrospiro[β-carboline-3,1'-cyclopentane], azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1,3-benzodioxol and so on.

In the specification, substituent in "cyclic group which may have a substituent(s)" represented by $A^2$ includes, for example, (1) hydrocarbon which may have a substituent(s), (2) carbocyclic ring which may have a substituent(s), (3) heterocyclic ring which may have a substituent(s), (4) hydroxyl which may have a substituent(s), (5) mercapto which may have a substituent(s), (6) amino which may have a substituent(s), (7) carbamoyl which may have a substituent(s), (8) sulfamoyl which may have a substituent(s), (9) carboxyl, (10) alkoxycarbonyl (e.g. C1-6 alkoxycarbonyl etc., such as methoxycarbonyl, ethoxycarbonyl, propoxycarbonyl, isopropoxycarbonyl, tert-butoxycarbonyl and so on), (11) sulfo ($-SO_3H$), (12) sulfino ($-SO_2H$), (13) phosphono ($-P(=O)OH_2$), (14) nitro, (15) cyano, (16) amidino, (17) imino, (18) dihydroborono ($-B(OH)_2$), (19) halogen atom (e.g. fluorine, chlorine, bromine, iodine), (20) alkylsufinyl (e.g. C1-4 alkylsulfinyl etc., such as methylsulfinyl, ethylsulfinyl and so on), (21) aromatic ring sulfinyl (e.g. C6-10 aromatic ring sulfinyl etc., such as phenylsulfinyl and so on), (22) alkylsulfonyl (e.g. C1-4 alkylsulfonyl etc., such as methylsulfonyl, ethylsulfonyl and so on), (23) aromatic ring sulfonyl (e.g. C6-10 aromatic ring sulfonyl etc., phenylsulfonyl and so on), (24) oxo, (25) thioxo, (26) (C1-6 alkoxyimino) methyl (e.g. (methoxyimino)methyl etc.), (27) acyl (28) formyl, (29) alkyl substituted with hydroxyl which may have a substituent(s), (30) alkyl substituted with mercapto which may have a substituent(s), (31) alkyl substituted with amino which may have a substituent(s), (32) (alkyl which may have a substituent(s))oxycarbonyl, (33) tri(C1-6 alkyl)silyl (e.g. trimethylsilyl etc.) and so on. These optional substituents may be substituted 1-5 at the replaceable position.

Hydrocarbon in "(1) hydrocarbon which may have a substituent(s)" includes, for example, alkyl, alkenyl, alkynyl, alkylidene, alkenylidene and so on.

Alkyl includes, for example, straight-chain or branched-chain C1-20 alkyl and so on, such as methyl, ethyl, n-propyl, isopropyl, n-butyl, isobutyl, sec-butyl, tert-butyl, n-pentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl etc. Straight-chain or branched-chain C1-8 alkyl is preferred. Straight-chain or branched-chain C1-6 alkyl is more preferred.

Alkenyl includes, for example, straight-chain or branched-chain C2-8 alkenyl and so on, such as ethenyl, propenyl, butenyl, pentenyl, hexenyl, heptenyl, octenyl etc. Straight-chain or branched-chain C2-6 alkenyl is preferred.

Alkynyl includes, for example, straight-chain or branched-chain C2-8 alkynyl and so on, such as ethynyl, propynyl, butynyl, pentynyl, hexynyl, heptynyl, octynyl etc. Straight-chain or branched-chain C2-6 alkynyl is preferred.

Alkylidene includes, for example, straight-chain or branched-chain C1-8 alkylidene and so on, such as methylidene, ethylidene, propylidene, butylidene, pentylidene, hexylidene, heptylidene, octylidene etc.

Alkenylidene includes, for example, straight-chain or branched-chain C2-8 alkenylidene and so on, such as ethenylidene, propenylidene, butenylidene, pentenylidene, hexenylidene, heptenylidene, octenylidene etc.

Here, substituent of hydrocarbon includes, for example, hydroxyl, mercapto, amino, carboxyl, nitro, cyano, mono- or di-C1-6 alkylamino (e.g. methylamino, ethylamino, propylamino, dimethylamino, diethylamino etc.), N-aromatic ring amino (e.g. N-phenylamino etc.), N-aromatic ring-N-alkylamino (e.g. N-phenyl-N-methylamino, N-phenyl-N-ethylamino, N-phenyl-N-propylamino, N-phenyl-N-butylamino, N-phenyl-N-pentylamino, N-phenyl-N-hexylamino etc.), acylamino, N-acyl-N-alkylamino, C1-6 alkoxy (e.g. methoxy, ethoxy, propoxy, isopropoxy, hexyloxy etc.), C3-7 cycloalkyl-C1-6 alkoxy (e.g. cyclohexylmethyloxy, cylcopentylethyloxy etc.), C3-7 cycloalkyloxy (e.g. cylcohexyloxy etc.), C7-15 aralkyloxy (e.g. benzyloxy, phenethyloxy, phenylpropyloxy, naphthylmethyloxy, naphthylethyloxy etc.), phenoxy, C1-6 alkoxycarbonyl (e.g. methoxycarbonyl, ethoxycarbonyl, tert-butoxycarbonyl etc.), C1-6 alkylcarbonyloxy (e.g. acetoxy, ethylcarbonyloxy etc.), C1-6 alkylthio (e.g. methylthio, ethylthio, propylthio, butylthio, pentylthio, hexylthio etc.), halogen atom (e.g. florine, chlorine, bromine, iodine), alkylsulfonyl (e.g. C1-4 alkylsulfonyl etc., such as methylsulfonyl, ethylsulfonyl and so on), aromatic ring sulfonyl (e.g. C6-10 aromatic ring sulfonyl etc., such as phenylsulfonyl and so on), carbamoyl which may have a substituent(s) (e.g. carbamoyl without substituent, N-mono-C1-6 alkylcarbamoyl (e.g. N-methylcarbamoyl, N-ethylcarbamoyl, N-propylcarbamoyl, N-isopropylcarbamoyl, N-butylcarbamoyl etc.), N,N-di C1-6 alkylcarbamoyl (e.g. N,N-dimethylcarbamoyl, N,N-diethylcarbamoyl, N,N-dipropylcarbamoyl, N,N-dibutylcarbamoyl etc.), piperidine-1-ylcarbonyl etc.), acyl, carbocyclic ring which may have a substituent(s), and heterocyclic ring which may have a substituent(s) etc. These optional substituents may be substituted 1-4 at the replaceable position. Here, alkyl in N-acyl-N-alkylamino means, for example, straight-chain or branched-chain C1-6 alkyl and so on, such as methyl, ethyl, propyl, isopropyl, butyl, isobutyl, sec-butyl, tert-butyl, pentyl, hexyl etc. In addition, acyl in acyl, acylamino and N-acyl-N-alkylamino has the same meanings as that of the after-mentioned (27) acyl. Additionally, carbocylic ring which may have a substituent(s) and heterocyclic ring which may have a substituent(s) have the same meanings as that of the after-mentioned (2) carbocyclic ring which may have a substituent(s), and (3) heterocyclic ring which may have a substituent(s).

Carbocylcic ring in "(2) carbocyclic ring which may have a substituent(s)" has the same meanings as that of carbocyclic ring represented by the above described ring $A^2$. Here, substituent of carbocyclic ring includes, for example, straight-chain or branched-chain C1-8 alkyl optionally with hydroxyl (e.g. methyl, ethyl, propyl, isopropyl, butyl, isobutyl, sec-butyl, tert-butyl, pentyl, hexyl, heptyl, octyl etc.), straight-chain or branched-chain C2-6 alkenyl (e.g. ethenyl, propenyl, butenyl, pentenyl, hexenyl etc.), straight-chain or branched-chain C2-6 alkynyl (e.g. ethynyl, propynyl, butynyl, pentynyl, hexynyl etc.), hydroxyl, straight-chain or branched-chain C1-6 alkoxy (e.g. methoxy, ethoxy, propoxy, isopropoxy, butoxy, isobutyloxy, tert-butoxy, pentyloxy, hexyloxy etc.), mercapto, straight-chain or branched-chain C1-6 alkylthio (e.g. methylthio, ethylthio, propylthio, isopropythio, butylthio, isobutylthio, tert-butylthio, pentylthio, hexylthio etc.), amino, mono- or di-C1-6 alkylamino (e.g. methylamino, ethylamino, propylamino, isopropylamino, butylamino, isobutylamino, tert-butylamino, pentylamino, hexylamino, dimethylamino, diethylamino, dipropylamino, N-methyl-N-ethylamino etc.), halogen atom (e.g. florine, chlorine, bromine, iodine), cyano, nitro, carboxyl, straight-chain or branched-chain C1-6 alkoxycarbonyl (e.g. methoxycarbonyl, ethoxycarbonyl, tert-butoxycarbonyl etc.), straight-chain or branched-chain C1-6 alkylcarbonyloxy (e.g. acetoxy, ethylcarbonyloxy etc.), trihalomethyl (e.g. trifluoromethyl etc.), trihalomethoxy (e.g. trifluoromethoxy etc.), trihalomethylthio (e.g. trifluoromethylthio etc.), dihalomethylthio (e.g. difluoromethylthio etc.), oxo, carbocylic ring (it has the same meanings as that of carbocyclic ring represented by the above described ring $A^2$), heterocyclic ring (it has the same meanings as that of heterocyclic ring represented by the above described ring $A^2$) and so on. These optional substituents may be substituted 1-4 at the replaceable position.

Heterocyclic ring in "(3) heterocyclic ring which may have a substituent(s)" has the same meanings as that of heterocyclic ring represented by the above described ring $A^2$. Here, substituent of heterocyclic ring has the same meanings as that of substituent in the above described "(2) carbocyclic ring which may have a substituent(s)".

Substituent in "(4) hydroxyl which may have a substituent(s)", "(5) mercapto which may have a substituent(s)" and "(6) amino which may have a substituent(s)" include, for example, hydrocarbon which may have a substituent(s) (it has the same meanings as that of the above described "(1) hydrocarbon which may have a substituent(s)"), carbocyclic ring which may have a substituent(s) (it has the same meanings as that of the above described "(2) carbocyclic ring which may have a substituent(s)"), heterocyclic ring which may have a substituent(s) (it has the same meanings as that of the above described "(3) heterocyclic ring which may have a substituent(s)"), alkylsulfonyl (e.g. C1-4 alkylsulfonyl etc., such as methylsulfonyl, ethylsulfonyl and so on), aromatic ring sulfonyl (e.g. C6-10 aromatic ring sulfonyl etc., such as phenylsulfonyl and so on), acyl (it has the same meanings as that of the after described (27) acyl), (alkyl which may have a substituent(s)) oxycarbonyl (it has the same meanings as that of the after described "(32) (alkyl which may have a substituent(s)) oxycarbonyl") and so on.

Here, "(4) hydroxyl which may have a substituent(s)" includes, for example, C1-8 alkoxy (e.g. methoxy, ethoxy, propoxy, isopropoxy, butoxy, isobutoxy, sec-butoxy, tert-butoxy, pentyloxy, hexyloxy, heptyloxy, octyloxy etc.), hydroxy substituted with carbocyclic ring which may have a substituent(s) (e.g. cyclopropyloxy, cyclobutyloxy, cyclopentyloxy, cyclohexyloxy, cycloheptyloxy, cyclooctyloxy etc.) and so on.

"(7) Carbamoyl which may have a substituent(s)" includes, for example, carbamoyl without substituent, N-mono-C1-6 alkylcarbamoyl (e.g. N-methylcarbamoyl, N-ethylcarbamoyl, N-propylcarbamoyl, N-isopropylcarbamoyl, N-butylcarbamoyl etc.), N,N-di C1-6 alkylcarbamoyl (e.g. N,N-dimethylcarbamoyl, N,N-diethylcarbamoyl, N,N-dipropylcarbamoyl, N,N-dibutylcarbamoyl etc.), piperidine-1-ylcarbonyl and so on.

"(8) Sulfamoyl which may have a substituent(s)" includes, for example, sulfamoyl without substituent, N-mono-C1-6 alkylsulfamoyl (e.g. N-methylsulfamoyl, N-ethylsulfamoyl, N-propylsulfamoyl, N-isopropylsulfamoyl, N-butylsulfamoyl etc.), N,N-di C1-6 alkylsulfamoyl (e.g. N,N-dimethylsulfamoyl, N,N-diethylsulfamoyl, N,N-dipropylsulfamoyl, N,N-dibutylsulfamoyl etc.) and so on.

"(27) Acyl" includes, for example, alkylcarbonyl which may have a substituent(s) (wherein, alkyl which may have a substituent(s) has the same meanings as that of alkyl which may have a substituent(s) in the above described "(1) hydrocarbon which may have a substituent(s)"), alkenylcarbonyl which may have a substituent(s) (wherein, alkenyl which may have a substituent(s) has the same meanings as that of alkenyl which may have a substituent(s) in the above described "(1) hydrocarbon which may have a substituent(s)"), alkynylcarbonyl which may have a substituent(s) (wherein, alkynyl which may have a substituent(s) has the same meanings as that of alkynyl which may have a substituent(s) in the above described "(1) hydrocarbon which may have a substituent(s)"), carbocyclic ring carbonyl which may have a substituent(s) (wherein, carbocyclic ring which may have a substituent(s) has the same meanings as that of the above described "(2) carbocyclic ring which may have a substituent(s)"), heterocyclic ring carbonyl which may have a substituent(s) (wherein, heterocyclic ring which may have a substituent(s) has the same meanings as that of the above described "(3) heterocyclic ring which may have a substituent(s)") and so on.

Hydroxyl which may have a substituent(s) in "(29) alkyl substituted with hydroxyl which may have a substituent(s)" has the same meanings as that of the above described "(4) hydroxyl which may have a substituent(s)". Mercapto which may have a substituent(s) in "(30) alkyl substituted with mercapto which may have a substituent(s)" has the same meanings as that of the above described "(5) mercapto which may have a substituent(s)". Amino which may have a substituent(s) in "(31) alkyl substituted with amino which may have a substituent(s)" has the same meanings as that of the above described "(6) amino which may have a substituent(s)". In addition, alkyl in "(29) alkyl substituted with hydroxyl which may have a substituent(s)", "(30) alkyl substituted with mercapto which may have a substituent(s) and "(31) alkyl substituted with amino which may have a substituent(s)" includes, for example straight-chain or branched-chain C1-6 alkyl and so on, such as methyl, ethyl, propyl, isopropyl, butyl, isobutyl, sec-butyl, tert-butyl, pentyl, hexyl etc.

Alkyl which may have a substituent(s) in "(32) (alkyl which may have a substituent(s)) oxycarbonyl" has the same meanings as that of "alkyl which may have a substituent(s)" in "(1) hydrocarbon which may have a substituent(s)".

In the specification, "hydrocarbon which may have a substituent(s)" represented by B has the same meanings as that of "(1) hydrocarbon which may have a substituent(s)" in substituent of "cyclic group which may have a substituent(s)" represented by ring $A^2$.

In the specification, "cyclic group which may have a substituent(s)" represented by B has the same meanings as that of "cyclic group which may have a substituent(s)" represented by ring $A^2$.

In the specification, "substituent" represented by $R^1$, $R^2$, $R^3$, $R^4$, $R^5$, $R^6$, $R^7$ or $R^8$ has the same meanings as that of "cyclic group" in "cyclic group which may have a substituent(s)" represented by ring $A^2$.

In the specification, "substituent" in "cyclic group which may have a substituent(s)" formed by two $R^1$ taken together, and "cyclic group which may have a substituent(s)" formed by $R^4$ and $R^5$ and/or $R^6$ and $R^7$ taken together with their binding carbon atoms, has the same meanings as that of substituent in "cyclic group which may have a substituent(s)" represented by ring $A^2$.

In the specification, "cyclic group" in "cyclic group which may have a substituent(s)" formed by two $R^1$ taken together, and "cyclic group which may have a substituent(s)" formed by $R^4$ and $R^5$ and/or $R^6$ and $R^7$ taken together with their binding carbon atoms, includes, for example, C3-10 mono-aromatic carbocyclic ring, which is partially or fully saturated, 3-10 membered mono-aromatic heterocyclic ring which may be partially or fully saturated, which may contain 1 to 2 hetero atom(s) selected from oxygen atom, nitrogen atom and sulfur atom(s) and so on.

Said C3-10 mono-aromatic carbocyclic ring, which is partially or fully saturated includes, for example, cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclootadiene ring and so on.

Said 3-10 membered mono-aromatic heterocyclic ring which may be partially or fully saturated, which may contain 1 to 4 hetero atom(s) selected from oxygen atom, nitrogen atom and sulfur atom(s) includes, for example, aziridine, azetidine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodizepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrotiepine, dihydrooxazole, tetrahydrooxazole (oxazolidine), dihydroisooxazole, tetrahydroisooxazole (isooxazolidine), dihydrothiazole, tetrahydrothiazole (isothiazolidine), dihydrooxazine, tetrahydrooxazine, dihydrooxazepine, tetrahydrooxazepine, perhydrooxazepine, dihydrothiazine, tetrahydrothiazine, dihydrothiazepine, tetrahydrothiazepine, perhydrothiazepine, morpholine, thiomorpholine, oxathiane, dioxolane, dioxane, dithiolane, dithiane ring and so on.

"Mono-carbocyclic ring" represented by ring $A^1$ includes, for example, C3-10 mono-aromatic carbocyclic ring, which is partially or fully saturated and so on. Said C3-10 mono-aromatic carbocyclic ring, which is partially or fully saturated includes, for example, cyclopropene, cyclobutene, cyclohexene, cycloheptene, cyclooctene, cyclopentadiene, cyclohexadiene, cycloheptadiene, cyclooctadiene, benzene ring and so on.

"Mono-heterocyclic ring" represented by ring $A^1$ includes, for example, 3-10 membered mono-aromatic heterocyclic ring which may be partially or fully saturated, which may contain 1 to 5 hetero atom(s) selected from oxygen atom, nitrogen atom and sulfur atom(s) and so on. Said 3-10 membered mono-aromatic heterocyclic ring which may be partially or fully saturated, which may contain 1 to 5 hetero atom(s) selected from oxygen atom, nitrogen atom and sulfur atom(s) includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodizepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrotiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane ring and so on.

In the specification, C1-3 alkylene in "C1-3 alkylene which may have a substituent(s)" represented by X or Z includes, for example, methylene, ethylene, propylene and so on.

In the specification, C2-3 alkenylene in "C2-3 alkenylene which may have a substituent(s)" represented by X or Z includes, for example, ethenylene, propenylene and so on.

In the specification, C2-3 alkynylene in "C2-3 alkynylene which may have a substituent(s)" represented by X or Z includes, for example, ethynylene, propynylene and so on.

In the specification, "substituent" in "C1-3 alkylene which may have a substituent(s)", "C2-3 alkenylene which may have a substituent(s)" or "C2-3 alkynylene which may have a substituent(s)" has the same meanings as that of substituent in "cyclic group which may have a substituent(s)" represented by ring $A^2$. These optional substituents may be substituted 1-2 at the replaceable position.

Ring $A^1$ preferably includes, benzene, pyridine, pyrimidine, pyrazine ring and so on. X preferably includes, bond, C1-3 alkylene which may have a substituent(s), C2-3 alkenylene which may have a substituent(s), C2-3 alkynylene which may have a substituent(s). It more preferably includes, bond, C1-3 alkylene which may have a substituent(s). It particularly preferably includes bond.

Y preferably includes, —C(=O)—, —C(=S)—, —C(=O)NR$^8$—, —SO$_2$—, —C(=O)O— or —SO$_2$NR$^8$— group (proviso that a left side of each group binds to X). It more preferably includes, —C(=O)—, —C(=S)—, —C(=O)NR$^8$— or —C(=O)O— group. It particularly preferably includes —C(=O)— or —C(=O)NR$^8$— group.

Z preferably includes, bond, C1-3 alkylene which may have a substituent(s), C2-3 alkenylene which may have a substituent(s), C2-3 alkynylene which may have a substituent(s). It more preferably includes, bond, C1-3 alkylene which may have a substituent(s).

"Hydrocarbon which may have a substituent(s)" represented by B preferably includes, C1-8 alkyl, C2-8 alkenyl or C2-8 alkynyl which may be substituted by 1 to 4 substituent(s) arbitrarily selected from hydroxyl, mercapto, amino, carboxyl, nitro, cyano, mono- or di-C1-6 alkylamino, C1-6 alkoxy, C1-6 alkylcarbonyloxy, C1-6 alkylthio, halogen atom, acyl, carbocyclic ring which may have a substituent(s), and heterocyclic ring which may have a substituent(s). It more preferably includes, C1-8 alkyl which may be substituted by 1 to 4 substituent(s) arbitrarily selected from carbocyclic ring which may have a substituent(s), and heterocyclic ring which may have a substituent(s).

"Cyclic group which may have a substituent(s)" represented by B or ring $A^2$ preferably includes, C3-10 mono- or bi-aromatic carbocyclic ring partially or fully saturated (e.g. benzene, cyclopentane, naphthalene, adamantane etc.), or 3-10 membered mono or bi-aromatic heterocyclic ring which may be partially or fully saturated, which may contain 1 to 4 hetero atom(s) selected from oxygen atom, nitrogen atom and sulfur atom(s) (e.g. pyridine, thiophene, tetrahydropyran, dihydrobenzofuran, 1,3-benzodioxol etc.) which may be substituted by 1 to 4 substituent(s) arbitrarily selected from C1-8 alkyl, C1-8 alkyl which may have a substituent(s), C2-8 alkenyl, C2-8 alkynyl, carbocyclic ring, heterocyclic ring, hydroxyl, C1-8 alkoxy (e.g. methoxy, ethoxy, propoxy, isopropoxy, butoxy, isobutoxy, sec-butoxy, tert-butoxy, pentyloxy, hexyloxy, heptyloxy, octyloxy etc.), C1-8 alkoxy which may have a substituent(s), C3-7 cycloalkyloxy (e.g. cyclopropyloxy, cyclobutyloxy, cyclopentyloxy, cyclohexyloxy, cycloheptyloxy etc.), C3-7 cycloalkyloxy which may have a substituent(s), mercapto, C1-8 alkylthio (e.g. methylthio, ethylthio, propylthio, isopropylthio, butylthio, isobutylthio, sec-butylthio, tert-butylthio, pentylthio, hexylthio, heptylthio, octylthio etc.), amino, NR$^{101}$R$^{102}$ (wherein, R$^{101}$ and R$^{102}$ are each independently hydrogen atom, or C1-8 alkyl), carboxyl, C1-6 alkoxycarbonyl, nitro, ciano, halogen atom, oxo, acyl, formyl and tri(C1-6 alkyl) silyl etc.

"Cyclic group which may have a substituent(s)" represented by ring $A^2$ is preferably substituted by at least two same or different substituents. In addition, said at least two same or different substituents may be taken together with their binding atoms to form cyclic group (this cyclic group has the same meanings as that of "cyclic group" in the above described "cyclic group which may have a substituent(s)" which two R$^1$ are taken together to form, "cyclic group which may have a substituent(s)" which R$^4$ and R$^5$ and/or R$^6$ and R$^7$ are taken together with their binding carbon atoms to form. It includes, for example, furan, pyran, oxazole, isoxazole, oxazine, dihydrofuran, tetrahydrofuran, dihydropyran, tetrahydropyran, dihydrooxazole, tetrahydrooxazole (oxazolidine), dihydroisoxazole, tetrahydroisoxazole (isoxazolidine), dihydrooxazine, tetrahydrooxazine, morpholine, oxathiane, dioxolane, dioxane ring etc.). Ring $A^2$ is more preferably substituted by two same or different substituents.

Said two same or different substituents preferably includes, for example, (1) halogen atom (e.g. fluorine, chlorine, bromine, iodine), (2) cyano, (3) C1-8 alkyl which may have a substituent(s) (it has the same meanings as the described above), (4) C1-8 alkoxy which may have a substituent(s) (it has the same meanings as the described above), (5) C3-7 cycloalkyloxy which may have a substituent(s) (it has the same meanings as the described above) and the like. Here, "substituent" in "C1-8 alkyl which may have a substituent(s)", "C1-8 alkoxy which may have a substituent(s)" or "C3-7 cycloalkyloxy which may have a substituent(s)" includes, for example, C1-8 alkyl, C2-8 alkenyl, C2-8 alkynyl, carbocyclic ring, heterocyclic ring, hydroxyl, C1-8 alkoxy, mercapto, C1-8 alkylthio, amino, NR$^{101}$R$^{102}$ (wherein, R$^{101}$ and R$^{102}$ are each independently hydrogen atom or C1-8 alkyl), carboxyl, C1-6 alkoxycarbonyl, nitro, cyano, halogen atom, oxo, acyl, formyl, tri(C1-6 alkyl) silyl and the like. These optional substituents may be substituted 1-9 at the replaceable position. It preferably includes halogen atom and the like. It more preferably includes fluorin atom. Here, "C1-8 alkoxy" in "C1-8 alkoxy which may have a substituent(s)" preferably includes methoxy, isopropoxy and the like. "C3-7 cycloalkyloxy which may have a substituent(s)" preferably includes cyclopentyloxy and the like. Said two same or different substituents more preferably includes, for example, (1) fluorine atom, (2) chlorine atom, (3) cyano, (4) methyl, (5) methoxy, (6) isopropoxy, (7) cyclopentyloxy and the like. One substituent among said two same or different substituents preferably includes C1-8 alkoxy which may have a substituent(s) or C3-7 cycloalkyloxy which may have a substituent(s). It particularly preferably includes methoxy, isopropoxy, cyclopentyloxy.

In addition, when

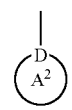

(wherein all the symbols have the same meanings as the described above)

is a cyclic group which has at least two same or different substituents, one substituent of said two same or different substituents is preferably substituted to an atom neighboring D. Such a substituent preferably includes, for example, C1-8 alkoxy which may have a substituent(s) or C3-7 cycloalkyloxy which may have a substituent(s) and the like.

"Cyclic group" represented by

preferably includes, benzene, thiophene, cyclopentane, or tetrahydropyran and the like. It more preferably includes benzene and the like. It further preferably includes

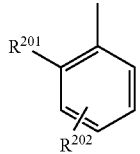

(wherein, $R^{201}$ is C1-8 alkoxy which may have a substituent(s) or C3-7 cycloalkyloxy which may have a substituent(s), $R^{202}$ is halogen atom, cyano, C1-8 alkyl which may have a substituent(s) or C1-8 alkoxy which may have a substituent(s)) and the like. $R^{201}$ is more preferably the substituent selected from (1) methoxy which may be substituted by fluorine atom, (2) isopropoxy which may be substituted by fluorine atom and (3) cyclopropyloxy which may be substituted by fluorine atom. $R^{202}$ is more preferably one substituent selected from (1) fluorine atom, (2) chlorine atom, (3) cyano, (4) methyl and (5) methoxy. $R^{201}$ is particularly preferably methoxy which may be substituted by fluorine atom.

In addition, when $R^{201}$ and $R^{202}$ are taken together with their binding atom to form cyclic group, "cyclic group" represented by

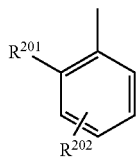

(wherein, all the symbols have the same meanings as the described above) preferably includes the ring represented by

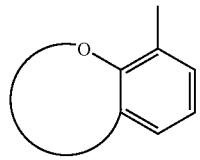

(wherein

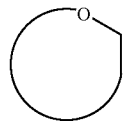

is 5-6 membered mono-heterocyclic ring which may further include one hetero atom selected from oxygen atom, nitrogen atom and sulfur atom) and the like. Here, 5-6 membered mono-heterocyclic ring which may further include one hetero atom selected from oxygen atom, nitrogen atom and sulfur atom includes, for example, furan, pyran, oxazole, isoxazole, oxazine, dihydrofuran, tetrahydrofuran, dihydropyran, tetrahydropyran, dihydrooxazole, tetrahydrooxazole (oxazolidine), dihydroisoxazole, tetrahydroisoxazole (isoxazolidine), dihydrooxazine, tetrahydrooxazine, morpholine, oxathiane, dioxolane, dioxane and the like.

"Substituent" represented by $R^1$, $R^2$, $R^3$, $R^4$, $R^5$, $R^6$ or $R^7$ preferably includes C1-8 alkyl, C2-8 alkenyl, C2-8 alkynyl, carbocyclic ring, heterocyclic ring, hydroxyl, C1-8 alkoxy, mercapto, C1-8 alkylthio, amino, $NR^{101}R^{102}$ (wherein $R^{101}$ and $R^{102}$ are each independently hydrogen atom or C1-8 alkyl), carboxyl, C1-6 alkoxycarbonyl, nitro, cyano, halogen atom, oxo, acyl, formyl, tri(C1-6 alkyl) silyl and the like.

"Cyclic group which may have a substituent(s)" which $R^4$ and $R^5$ and/or $R^6$ and $R^7$ are taken together with their binding carbon atoms to represent, preferably includes C3-8 cycloalkyl (e.g. cyclopropyl, cyclobutyl, cyclopentyl, cyclohexyl, cycloheptyl, cyclooctyl etc.) which may be substituted by 1 to 4 substituent(s) selected from C1-8 alkyl, C2-8 alkenyl, C2-8 alkynyl, carbocyclic ring, heterocyclic ring, hydroxyl, C1-8 alkoxy, mercapto, C1-8 alkylthio, amino, $NR^{101}R^{102}$ (wherein $R^{101}$ and $R^{102}$ are each independently hydrogen atom or C1-8 alkyl), carboxyl, C1-6 alkoxycarbonyl, nitro, cyano, halogen atom, oxo, acyl, formyl, tri(C1-6 alkyl) silyl and the like.

$R^4$ and $R^5$ are preferably taken together their binding carbon atoms to form cyclic group which may have a substituent(s). Such a cyclic group preferably includes cyclopropyl, cyclobutyl, cyclopentyl, cyclohexyl and the like. It more preferably includes cyclopropyl and the like.

In the specification, D is preferably a carbon atom and the like.

In the specification, "C1-8 alkyl which may have a substituent(s)" represented by $B^2$ has the same meanings as that of "C1-8 alkyl which may have a substituent(s)" represented by B. It is preferably C1-8 alkyl without substituent and the like. It is more preferably methyl and the like.

In the specification, "C1-8 alkoxy which may have a substituent(s)" or "C3-7 cycloalkyloxy which may have a substituent(s)" represented by $R^{201}$ has the same meanings as that of "C1-8 alkoxy which may have a substituent(s)" or "C3-7 cycloalkyloxy which may have a substituent(s)" in "two same or different substituents" among the above described ring $A^2$, respectively. "Halogen atom", "C1-8 alkyl which may have a substituent(s)" or "C1-8 alkoxy which may have a substituent(s)" represented by $R^{202}$ has the same meanings as that of "halogen atom", "C1-8 alkyl which may have a substituent(s)" or "C1-8 alkoxy which may have a substituent(s)" in "two same or different substituents" among the above described ring $A^2$, respectively.

The compound represented by formula (I) preferably includes the compound represented by formula (I-A):

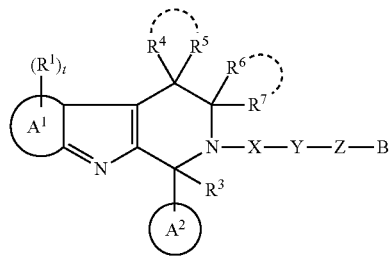

(I-A)

(wherein, all the symbols have the same meanings as the described above), or the compound represented by formula (I-B):

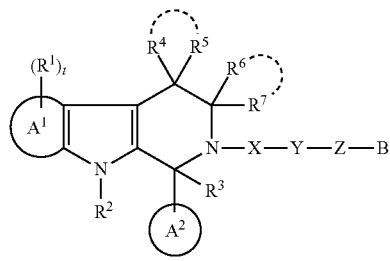

(I-B)

(wherein, all the symbols have the same meanings as the described above).

The compound represented by formula (I-A) preferably includes the compound represented by formula (I-A-1):

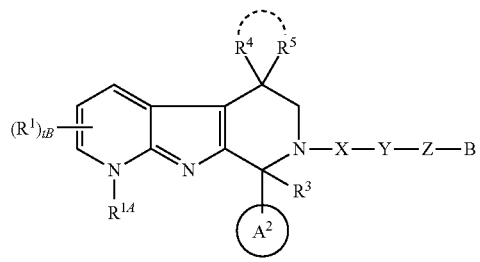

(I-A-1)

(wherein, $R^{1A}$ has the same meanings as that of $R^1$, tB is 0 or an integer of 1 to 3, the other symbols have the same meanings as the described above).

The compound represented by formula (I-B) preferably includes the compound represented by formula (I-B-1)

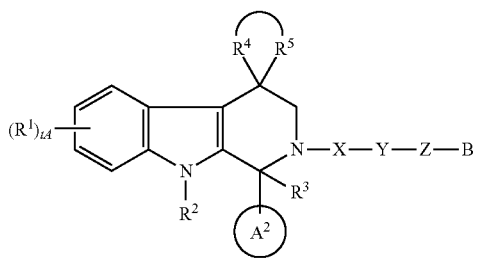

(I-B-1)

(wherein, tA is 0 or an integer of 1 to 4, $R^4$ and $R^5$ are taken together with their binding carbon atom to form cyclic group which may have a substituent(s), the other symbols have the same meanings as the described above), the compound represented by formula (I-B-2)

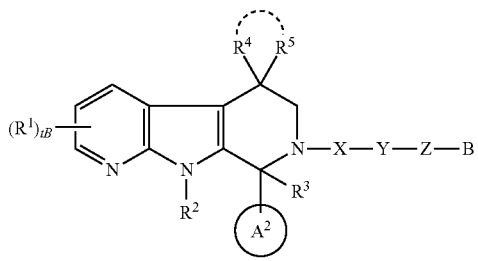

(I-B-2)

(wherein, all the symbols have the same meanings as the described above), the compound represented by formula (I-B-3)

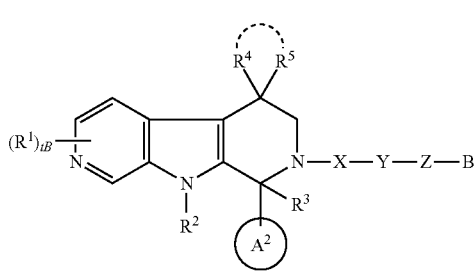

(I-B-3)

(wherein, all the symbols have the same meanings as the described above), the compound represented by formula (I-B-4)

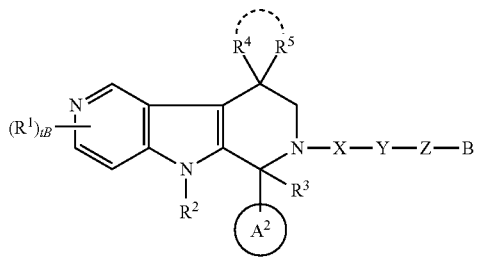

(I-B-4)

(wherein, all the symbols have the same meanings as the described above), or the compound represented by formula (I-B-5)

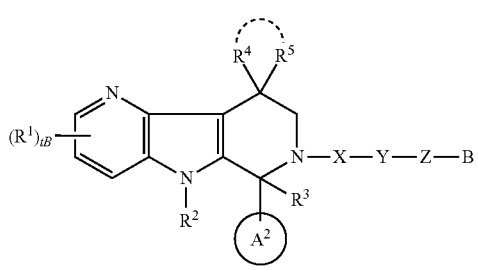

(I-B-5)

(wherein, all the symbols have the same meanings as the described above).

In addition, among the compound represented by formula (I-B-1), it preferably includes the compound of which ring $A^2$ is a cyclic group having at least two same or different substituents. Concretely, it preferably includes the compound represented by formula (I-B-1-1)

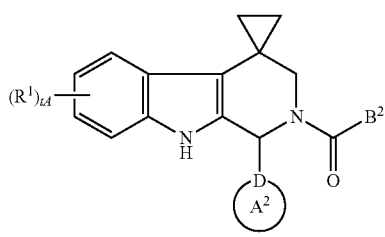

(I-B-1-1)

(wherein, all the symbols have the same meanings as the described above).

It particularly preferably includes the compound represented by formula (I-B-1-2)

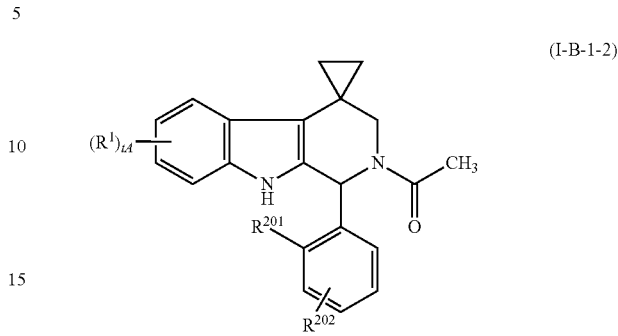

(I-B-1-2)

(wherein, all the symbols have the same meanings as the described above).

Additionally, among the compound represented by formula (I), both the compound represented by formula (I-C)

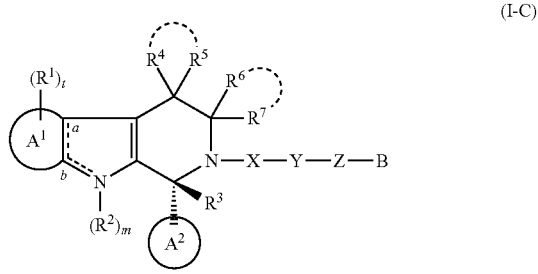

(I-C)

(wherein, all the symbols have the same meanings as the described above) and the compound represented by formula (I-D)

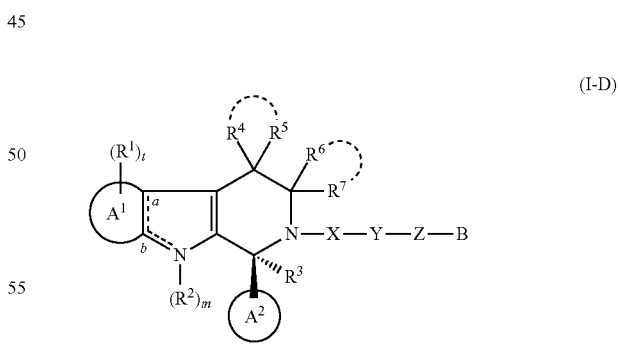

(I-D)

(wherein, all the symbols have the same meanings as the described above) are preferred. It particularly preferably includes the compound represented by formula (I-C).

In addition, in case of the compound represented by formula (I-B-1-1) or formula (I-B-1-2), it preferably includes ring $A^2$ is β-configuration. Concretely, it preferably includes the compound represented by formula (I-B-1-1-a)

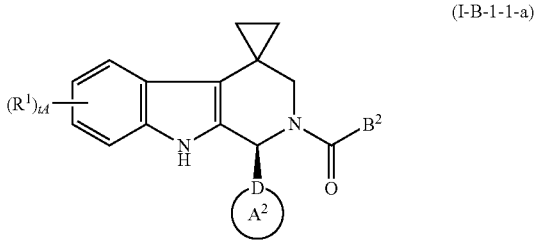

(I-B-1-1-a)

(wherein, all the symbols have the same meanings as the described above). It particularly preferably includes the compound represented by formula (I-B-1-2-a)

(I-B-1-2-a)

(wherein, all the symbols have the same meanings as the described above).

Preferable compounds for preparing the pharmaceutical composition which is a preventive and/or therapeutic agent for the diseases caused by stress include all the compounds of the present invention showed in Examples. Particularly preferable compounds include, for example, 2-acetyl-1-(4-chloro-2-methoxyphenyl)-1,2,3,9-tetrahydrospiro[β-carboline-4,1'-cyclopropane],
2-acetyl-1-(4-chloro-2-methoxyphenyl)-5-fluoro-1,2,3,9-tetrahydrospiro[β-carboline-4,1'-cyclopropane],
2-acetyl-1-(4-chloro-2-methoxyphenyl)-5,6-difluoro-1,2,3,9-tetrahydrospiro[β-carboline-4,1'-cyclopropane],
2-acetyl-1-(4-chloro-2-methoxyphenyl)-6-fluoro-1,2,3,9-tetrahydrospiro[β-carboline-4,1'-cyclopropane],
2-acetyl-1-(4-chloro-2-methoxyphenyl)-5-methoxy-1,2,3,9-tetrahydrospiro[β-carboline-4,1'-cyclopropane],
2-acetyl-5-chloro-1-(4-chloro-2-methoxyphenyl)-1,2,3,9-tetrahydrospiro[β-carboline-4,1'-cyclopropane],
2-acetyl-5-chloro-1-(2-methoxy-4-methylphenyl)-1,2,3,9-tetrahydrospiro[β-carboline-4,1'-cyclopropane],
2-acetyl-5-fluoro-1-(2-fluoro-6-methoxyphenyl)-1,2,3,9-tetrahydrospiro[β-carboline-4,1'-cyclopropane],
2-acetyl-6-fluoro-1-(4-fluoro-2-methoxyphenyl)-1,2,3,9-tetrahydrospiro[β-carboline-4,1'-cyclopropane],
2-acetyl-5-fluoro-1-(4-fluoro-2-methoxyphenyl)-1,2,3,9-tetrahydrospiro[β-carboline-4,1'-cyclopropane],
2-acetyl-1-(5-fluoro-2-methoxyphenyl)-5-methoxy-1,2,3,9-tetrahydrospiro[β-carboline-4,1'-cyclopropane],
2-acetyl-1-(4-fluoro-2-methoxyphenyl)-5-methoxy-1,2,3,9-tetrahydrospiro[β-carboline-4,1'-cyclopropane],
2-acetyl-1-(2,4-dimethoxyphenyl)-5-methoxy-1,2,3,9-tetrahydrospiro[β-carboline-4,1'-cyclopropane],
2-acetyl-1-(2-fluoro-6-methoxyphenyl)-5-methoxy-1,2,3,9-tetrahydrospiro[β-carboline-4,1'-cyclopropane],
2-acetyl-1-(4-chloro-2-methoxyphenyl)-6,7-dimethoxy-1,2,3,9-tetrahydrospiro[β-carboline-4,1'-cyclopropane],
2-acetyl-1-(2-methoxy-4-methylphenyl)-1,2,3,9-tetrahydrospiro[β-carboline-4,1'-cyclopropane],
2-acetyl-5-fluoro-1-(2-methoxy-4-methylphenyl)-1,2,3,9-tetrahydrospiro[β-carboline-4,1'-cyclopropane],
2-acetyl-1-(4-chloro-2-methoxyphenyl)-6-methoxy-1,2,3,9-tetrahydrospiro[β-carboline-4,1'-cyclopropane],
2-acetyl-1-(4-fluoro-2-methoxyphenyl)-6-methoxy-1,2,3,9-tetrahydrospiro[β-carboline-4,1'-cyclopropane],
2-acetyl-6-methoxy-1-(2-methoxy-4-methylphenyl)-1,2,3,9-tetrahydrospiro[β-carboline-4,1'-cyclopropane],
2-acetyl-1-(2-fluoro-6-methoxyphenyl)-6-methoxy-1,2,3,9-tetrahydrospiro[β-carboline-4,1'-cyclopropane],
2-acetyl-6,7-dimethoxy-1-(2-methoxy-4-methylphenyl)-1,2,3,9-tetrahydrospiro[β-carboline-4,1'-cyclopropane],
2-acetyl-1-(4-chloro-2-methoxyphenyl)-5-methyl-1,2,3,9-tetrahydrospiro[β-carboline-4,1'-cyclopropane],
2-acetyl-1-(2-methoxy-4-methylphenyl)-5-methyl-1,2,3,9-tetrahydrospiro[β-carboline-4,1'-cyclopropane],
2-acetyl-1-(2,3-dihydro-1-benzofuran-7-yl)-6-methoxy-1,2,3,9-tetrahydrospiro[β-carboline-4,1'-cyclopropane],
2-acetyl-1-(4-chloro-2-methoxyphenyl)-6-methoxy-5-methyl-1,2,3,9-tetrahydrospiro[β-carboline-4,1'-cyclopropane],
2-acetyl-1-(4-chloro-2-methoxyphenyl)-5,6-dimethoxy-1,2,3,9-tetrahydrospiro[β-carboline-4,1'-cyclopropane],
(1S)-2-acetyl-1-(4-chloro-2-methoxyphenyl)-5-fluoro-1,2,3,9-tetrahydrospiro[β-carboline-4,1'-cyclopropane],
(−)-2-acetyl-1-(4-chloro-2-methoxyphenyl)-5,6-difluoro-1,2,3,9-tetrahydrospiro[β-carboline-4,1'-cyclopropane],
(+)-2-acetyl-1-(4-chloro-2-methoxyphenyl)-5,6-difluoro-1,2,3,9-tetrahydrospiro[β-carboline-4,1'-cyclopropane],
(+)-2-acetyl-1-(4-chloro-2-methoxyphenyl)-5-methoxy-1,2,3,9-tetrahydrospiro[β-carboline-4,1'-cyclopropane],
(+)-2-acetyl-1-(2-fluoro-6-methoxyphenyl)-5-methoxy-1,2,3,9-tetrahydrospiro[β-carboline-4,1'-cyclopropane],
(+)-2-acetyl-5-fluoro-1-(2-fluoro-6-methoxyphenyl)-1,2,3,9-tetrahydrospiro[β-carboline-4,1'-cyclopropane],
(+)-2-acetyl-1-(4-chloro-2-methoxyphenyl)-6,7-dimethoxy-1,2,3,9-tetrahydrospiro[β-carboline-4,1'-cyclopropane],
2-acetyl-5-chloro-1-(4-fluoro-2-methoxyphenyl)-1,2,3,9-tetrahydrospiro[β-carboline-4,1'-cyclopropane],
2-acetyl-5,6-difluoro-1-(4-fluoro-2-methoxyphenyl)-1,2,3,9-tetrahydrospiro[β-carboline-4,1'-cyclopropane],
2-acetyl-5,6-difluoro-1-(2-methoxy-4-methylphenyl)-1,2,3,9-tetrahydrospiro[β-carboline-4,1'-cyclopropane],
2-acetyl-5-chloro-1-(2-fluoro-6-methoxyphenyl)-1,2,3,9-tetrahydrospiro[β-carboline-4,1'-cyclopropane],
2-acetyl-1-(4-chloro-2-isopropoxyphenyl)-1,2,3,9-tetrahydrospiro[β-carboline-4,1'-cyclopropane],
2-acetyl-1-[4-chloro-2-(cyclopentyloxy)phenyl]-1,2,3,9-tetrahydrospiro[β-carboline-4,1'-cyclopropane],
4-(2-acetyl-1,2,3,9-tetrahydrospiro[β-carboline-4,1'-cyclopropane]-1-yl)-3-methoxybenzonitrile,
2-acetyl-1-(4-chloro-2-methoxyphenyl)-5,7-difluoro-1,2,3,9-tetrahydrospiro[β-carboline-4,1'-cyclopropane],
2-acetyl-1-(4-chloro-2-methoxyphenyl)-8-fluoro-1,2,3,9-tetrahydrospiro[β-carboline-4,1'-cyclopropane],
4-(2-acetyl-5-fluoro-1,2,3,9-tetrahydrospiro[β-carboline-4,1'-cyclopropane]-1-yl)-3-methoxybenzonitrile,
2-acetyl-5,6-dimethoxy-1-(2-methoxy-4-methylphenyl)-1,2,3,9-tetrahydrospiro[β-carboline-4,1'-cyclopropane],
2-acetyl-5-methoxy-1-(2-methoxyphenyl)-1,2,3,9-tetrahydrospiro[β-carboline-4,1'-cyclopropane],
4-(2-acetyl-5-methoxy-1,2,3,9-tetrahydrospiro[β-carboline-4,1'-cyclopropane]-1-yl)benzonitrile,
2-acetyl-1-(2,3-dihydro-1-benzofuran-7-yl)-5-methoxy-1,2,3,9-tetrahydrospiro[β-carboline-4,1'-cyclopropane], 2-acetyl-5-methoxy-1-(2-methoxy-4-methylphenyl)-1,2,3,9-tetrahydrospiro[β-carboline-4,1'-cyclopropane], 2-acetyl-1-(4-chloro-2-methoxyphenyl)-6,8-dimethoxy-1,2,3,9-tetrahydrospiro[β-carboline-4,1'-cyclopropane], 2-acetyl-6-chloro-1-(4-chloro-2-methoxyphenyl)-1,2,3,9-tetrahydrospiro[β-carboline-4,1'-cyclopropane], 2-acetyl-1-(4-chloro-2-methoxyphenyl)-5-fluoro-8-methoxy-1,2,3,9-tetrahydrospiro[β-carboline-4,1'-cyclopropane], 2-acetyl-5-fluoro-1-(4-fluoro-2-methoxyphenyl)-8-methoxy-1,2,3,9-tetrahydrospiro[β-carboline-4,1'-cyclopropane], (+)-2-acetyl-1-(2-fluoro-6-methoxyphenyl)-6-methoxy-1,2,3,9-tetrahydrospiro[β-carboline-4,1'-cyclopropane], (+)-2-acetyl-1-(2-methoxy-4-methylphenyl)-5-methyl-1,2,3,9-tetrahydrospiro[β-carboline-4,1'-cyclopropane], (+)-2-acetyl-1-(4-chloro-2-methoxylphenyl)-6-methoxy-5-methyl-1,2,3,9-tetrahydrospiro[β-carboline-4,1'-cyclopropane], (+)-2-acetyl-5-fluoro-1-(4-fluoro-2-methoxyphenyl)-1,2,3,9-tetrahydrospiro[β-carboline-4,1'-cyclopropane], (+)-2-acetyl-5,6-difluoro-1-(2-methoxy-4-methylphenyl)-1,2,3,9-tetrahydrospiro[β-carboline-4,1'-cyclopropane], (+)-2-acetyl-5-chloro-1-(4-chloro-2-methoxyphenyl)-1,2,3,9-tetrahydrospiro[β-carboline-4,1'-cyclopropane] and the like.

[Isomer]

Unless otherwise specified, all isomers are included in the present invention. For example, alkyl, alkenyl, alkynyl, alkoxy, alkylthio, alkylene, alkenylene, alkynylene group include straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers having optical activity (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention.

According to the present invention, unless otherwise indicated and as is apparent for those skilled in the art, the symbol ⟋ indicates that it is bound to α-configuration, the symbol ⟍ indicates that it is bound to β-configuration, and the ⟋ indicates that it is a mixture of α-configuration and β-configuration which may be mixed by optional ratio.

The optically active compounds of the present invention may not only include 100% pure ones but also the other optical isomers less than 50%.

[Salt, N-Oxide and Solvent]

The salts of the compounds represented by formula (I) include all of pharmaceutically acceptable ones. As pharmaceutically acceptable salts, non-toxic, water-soluble salts are preferred. The suitable salts include for example, salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), pharmaceutical acceptable salts of organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (salts of inorganic acids (e.g., hydrochloride, hydrobromide, hydroiodide, sulfate, phosphate, nitrate etc.), and salts of organic acids (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.).

N-oxide of the compound represented by formula (I) means nitrogen atom of the compound represented by formula (I) is oxidized. The N-oxide of the compound of the present invention may be the above described salts of alkali (earth) metals, ammonium salts, salts of organic amine, acid addition salts and so on.

The suitable solvates of the compound represented by formula (I) include for example, hydrates, solvates of the alcohols (e.g., ethanol etc.), and so on. The solvates are preferably nontoxic and water-soluble. In addition, the solvate of compound of the present invention included the above described salts of alkali (earth) metals, ammonium salts, salts of organic amine, acid addition salts, N-oxide and so on.

The compound of the present invention may be converted into the above described N-oxide, the above described solvates by known methods.

[Prodrug]

The prodrug of the compounds represented by formula (I) means a compound is the compound represented by formula (I) by reaction with enzymes, gastric acids and so on within an organism. The prodrug of the compounds represented by formula (I) include, when the compounds represented by formula (I) have amino, the prodrug is the compounds the amino of which is acylated, alkylated, phosphorylated (e.g., the compounds are that the amino of the compounds represented by formula (I) is eicosanoated, alanylated, pentylaminocarbonylated, (5-methyl-2-oxo-1,3-dioxolan-4-yl)methoxycarbonylated, tetrahydrofuranated, pyrrolidylmethylated, pivaloyloxymethylated, acetoxymethylated, tert-butylated, etc.); when the compounds represented by formula (I) have hydroxyl, the prodrug is the compounds the hydroxyl of which are acylated, alkylated, phosphorylated, borated (e.g., the compounds are that the hydroxyl of the compounds represented by formula (I) are acetylated, palmitoylated, propanoylated, pivaloylated, succinylated, fumarylated, alanylated, dimethylaminomethylcarbonylated etc.); when the compounds represented by formula (I) have carboxyl, the prodrug is the compound the carboxyl of which are esterified, amidated (e.g., the compounds are that the carboxyl of the compounds represented by formula (I) is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated etc.); and so on. These compounds can be prepared by known methods. In addition, the prodrug of the compound represented by formula (I) may be either hydrate or nonhydrate. In addition, the prodrug of the compound represented by formula (I) may be converted into the compound represented by formula (I) under the physiological condition which is described in "the development of medicine" vol. 7 "molecular design" published in 1991 Hirokawa shoten p.p. 163-198. Further, the compound represented by formula (I) may be labeled with isotopes (e.g. $^3H$, $^{14}C$, $^{35}S$, $^{125}I$ etc.) and so on.

[Pharmacological Activity]

As pharmacological test except one described in Example, for example there are the methods as follows.

Determination of Pregnenolone in Rat Adrenocortical Mitochondria:

The steroid productivity of compound of the present invention can be evaluated using rat adrenocortical mitochondria.

After intraperitoneal administration of 20 mg/mL cycloheximide solution (1 mL) to male SD rats, 101 U/mL adrenocorticotropic hormone (ACTH) solution (0.3 mL) is intraperitoneally administered to them in five minutes. 20 minutes after ACTH administration, the rats are sacrificed by cervical dislocation and bilateral adrenal cortexes are removed at once. The removed adrenal cortexes are homogenized in buffer A (composition: 50 mmol/L Tris-HCl; 250 mmol/L sucrose) and then the suspension is centrifuged at 2000 g for 3 minutes at 4 degrees centigrade. The obtained supernatant is centrifuged at 12500 g for 10 minutes at 4 degrees centigrade. The pellet is washed with buffer A twice and suspended in buffer B (composition: 250 mmol/L sucrose; 10 mmol/L potassium phosphate buffer; 15 mmol/L triethanolamine; 20 mmol/L potassium chloride; 5 mmol/L magnesium chloride; 10 μmol/L trilostane; 10 μmol/L SU10603) for experiments. Assay buffer which includes malic acid (150 mmol/L), β-NADP$^+$ (5 mmol/L) and compound of the present invention is incubated for 5 minutes at 37 degrees centigrade. Then, crude mitochondrial membrane fraction derived from rat adrenal cortex is added and further incubated for 10 minutes at 37 degrees centigrade to produce pregnenolone (final concentration of the compound: 1 μmol/L). After incubation, the reaction is terminated by addition of ethanol, extracted by addition of n-hexane and then evaporated to dryness. The residue is dissolved in buffer C (composition: 0.1% gelatin; phosphate buffered salts solution), centrifuged and then the collected supernatant is determined as samples for measurement. [$^3$H] pregnenolone (10000 cpm; 100 μL), anti-pregnenolone antibody (ICN Biomedicals Inc; 100 μL) and sample (100 μL) are mixed and incubated overnight at 4 degrees centigrade. After the reaction, the mixture is added by dextran/charcoal (200 μL), mixed well, kept on ice for 10 minutes and then centrifuged. The radioactivity of the supernatant is measured by liquid scintillation counter. The pregnenolone in the sample is calculated from the standard curve.

Effect of Compound of the Present Invention on Increase in Pregnenolon Content in the Brain by Loading Stressor:

It can be confirmed that MBR antagonist can inhibit steroid production in the brain, as follows.

Male Wistar rats are loaded with psychological stressor (Brain Res., 641, 21-28, 1994). Water is stored up to about 10 cm depth in a container of which the platform is set up at the center. Rats in the non-treated group are loaded without administration and stressor. In contrast, rats in the stressor loaded group are orally administered with the vehicle or the compounds and 30 minutes later the rats are put on the platform to be loaded with stressor. One hour later from starting to load, the rats are irradiated by microwave (output: about: about 6.5 kW, exposure time: 0.96 s) using microwave applicator (Muromachi Kikai Co., Ltd.) and then the bilateral hippocampuses are removed and weighed. The hippocampuses are added by internal standard substance (D$_4$-pregnenolone 20 ng), water (1 mL) and diethylether/n-hexane (9:1, 3 mL) and stirred. The mixture is crushed by ultrasonic waves, stirred again, centrifuged at 3000 rpm for minutes and the organic layer is transferred to new tube with Pasteur pipet. The water phase is extracted with diethylether/n-hexane (9:1, 3 mL) again and the organic layer is mixed to the above described extract. After reduced pressure to dryness, the residue is dissolved with 150 μL water/acetonitrile (1:9) again and measured by liquid chromatography/mass spectrometry (LC-MS). The measurement condition is shown as follows.
LC (Liquid chromatography): Hewlett Packard series 1100,
Column: Inertsil ODS-3, 3 μm, 2, 1$^\psi$×100 mm,
Temperature: room temperature,
Mobile phase: 5 mmol/L CH$_3$CO$_2$NH$_4$/MeCN (10:90),
Flow rate: 0.2 mL/min,
Injection volume: 40 μL,
MS (Micro spectrometry): Quattoro II (Micromass),
Ionization mode: Atmosphere Pressure Chemical Ionization (APCI),
positive; Corona: 3.4 kV,
Sheath gas: N2 (50 L/hr),
Source temperature: 180 degrees centigrade,
Probe temperature: 550 degrees centigrade,
Detection: Pregnenolone: m/z 317.2 (cone: 10V),
D$_4$-pregnenolone: m/z 321.2 (cone: 10V).

[Processes for the Preparation of Compound of the Present Invention]

The compound of the present invention represented by formula (I) can be prepared by combining the known processes, for example, the following processes or the processes shown in Examples, which is the properly improved processes described in "*Comprehensive Organic Transformations: A Guide to Functional Group Preparations,* 2nd Edition", "Richard C. Larock, John Wiley & Sons Inc, 1999". Still, ingredients may be used as salts in the following each processes for the preparation. As these salts, the salts described as the pharmaceutically acceptable ones in the above described formula (I) can be used.

a) Among the compounds represented by formula (I), the compound wherein X is a bond, Y is —C(=O)—, —C(=O)NR$^8$—, —SO$^2$—, —C(=O)O—, —SO$^2$NR$^8$—, that is, the compound represented by formula (IA)

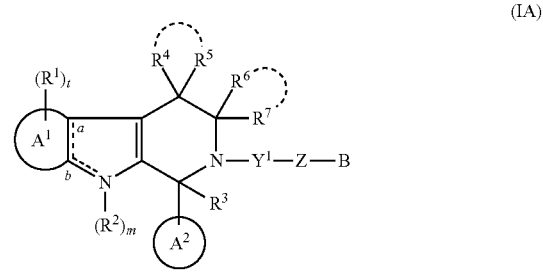

(IA)

(wherein, Y$^1$ is —C(=O)—, —C(=O)NR$^8$—, —SO$_2$—, —C(=O)O— or SO$_2$NR$^8$—, the other symbols have the same meanings as that of the described above) can be prepared by following processes.

The compound represented by formula (IA) can be prepared by the compound represented by formula (II)

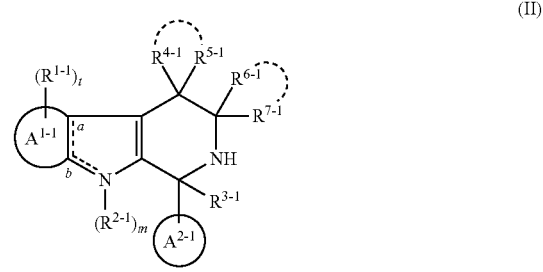

(II)

(wherein, ring A$^{1-1}$, ring A$^{2-1}$, R$^{1-1}$, R$^{2-1}$, R$^{3-1}$, R$^{4-1}$, R$^{5-1}$, R$^{6-1}$ or R$^{7-1}$ has the same meanings as that of ring A$^1$, ring A$^2$, R$^1$, R$^2$, R$^3$, R$^4$, R$^5$, R$^6$ or R$^7$, respectively. But carboxyl, hydroxyl, amino or mercapt included the group represented by ring $A^{1-1}$, ring $A^{2-1}$, $R^{1-1}$, $R^{2-1}$, $R^{3-1}$, $R^{4-1}$, $R^{5-1}$, $R^{6-1}$ or $R^{7-1}$ is protected, if necessary), with the compound represented by formula (III)

 (III)

(wherein, L is a leaving group (e.g. halogen atom, imidazolyl etc.), $B^1$ has the same meanings as that of B. But carboxyl, hydroxyl, amino or mercapt included the group represented by $B^1$ is protected, if necessary. The other symbols have the same meanings as the described above), if necessary, followed by subjecting to a deprotection reaction of protection group.

The reaction with the compound represented by formula (II) and the compound represented by formula (III) is carried out, for example, by reacting the compound represented by formula (II) with the compound represented by formula (III) in an organic solvent (e.g. chloroform, dichloromethane, diethylether, tetrahydrofuran etc.) under the presence of a base (e.g. pyridine, triethylamine, dimethylaniline, dimethylaminopyridine, diisopropylethylamine etc.) at a temperature from −20 degrees centigrade to reflux temperature.

Or, it is carried out by reacting the compound represented by formula (II) with the compound represented by formula (III) in an organic solvent (e.g. dioxane, tetrahydrofuran, diethylether etc.) using alkaline solution (e.g. sodium bicarbonate or sodium hydroxide solution etc.) at the temperature from 0 degrees centigrade to reflux temperature.

The deprotecting reaction of a protective group for carboxyl, hydroxyl, amino, or mercapto is known, and it includes
(1) alkaline hydrosis,
(2) deprotection reaction under acidic conditions,
(3) deprotection reaction by hydrogenolysis,
(4) deprotection reaction of a silyl group,
(5) deprotection reaction using metals,
(6) deprotection reaction using metal complexes, and the like.
These methods are described concretely as follows.

(1) The deprotection reaction by alkaline hydrolysis is, for example, carried out in an organic solvent (e.g., methanol, tetrahydrofuran, or dioxane etc.) using a hydroxide of an alkali metal (e.g., sodium hydroxide, potassium hydroxide, or lithium hydroxide etc.), a hydroxide alkaline earth metal (e.g., barium hydroxide, or calcium hydroxide etc.), or a carbonate (e.g., sodium carbonate or potassium carbonate, etc.), or an aqueous solution thereof, or a mixture thereof at a temperature of 0 to 40° C.

(2) The deprotection reaction under acidic conditions is carried out, for example, in an organic solvent (e.g., dichloromethane, chloroform, dioxane, ethyl acetate, or anisole etc.) in an organic acid (e.g., acetic acid, trifluoroacetic acid, methansulfonic acid, or p-tosylate, etc.), or an inorganic acid (e.g., hydrochloric acid, or sulfuric acid, etc.) or a mixture thereof (e.g., hydrogen bromide/acetic acid, etc.) at a temperature of 0 to 100° C.

(3) The deprotection reaction by hydrogenolysis is carried out, for example, in a solvent (e.g., ethers (e.g., tetrahydrofuran, dioxane, dimethoxyethane (DME), or diethylether, etc.), alcohols (e.g., methanol, or ethanol, etc.), benzenes (e.g., benzene, or toluene etc.), ketones (e.g., acetone, or methylethylketone, etc.), nitriles (e.g., actetonitrile etc.), amides (e.g., DMF etc.), water, ethyl acetate, acetic acid, or a mixed solvent of at least two of these etc.) in the presence of a catalyst (e.g., palladium-carbon, palladium black, palladium hydroxide-carbon, platinum oxide, or Raney nickel, etc.) under the hydrogen atmosphere at normal pressure or under pressurization, or in the presence of ammonium formate at a temperature of 0 to 200° C.

(4) The deprotection reaction of a silyl group is carried out, for example, in a water-miscible organic solvent (e.g., tetrahydrofuran, or acetonitrile, etc.) using tetrabutylammonium fluoride at a temperature of 0 to 40° C.

(5) The deprotection reaction using metals is carried out, for example, in an acidic solvent (e.g., acetic acid, pH4.2-7.2 buffer solution, or a mixture of a solution thereof and an organic solvent of tetrahydrofuran etc.) in the presence of zinc powder, if necessary sonicating, at the temperature of 0 to 40° C.

(6) The deprotection reaction using metal complexes is carried out, for example, in an organic solvent (e.g., dichloromethane, DMF, THF, ethyl acetate, acetonitrile, dioxane, ethanol etc.), water, or a mixture thereof, in the presence of a trap reagent (e.g., tributyltin hydride, triethylsilane, dimedone, morpholine, diethylamine, pyrrolidine, etc.), an organic acid (e.g., acetic acid, formic acid, 2-ethyl hexanoic acid, etc.) and/or salts of organic acid (e.g., sodium 2-ethylhexanoate, potassium 2-ethylhexanoate etc.), in the presence or absence of a phosphine reagent (e.g., triphenylphosphine etc.), using metal complexes (e.g., tetrakistriphenylphosphinepalladium(0), dichlorobis(triphenylphosphine)palladium(II), palladium acetate(II), tris(triphenylphosphine) rhodium(I) chloride etc.) at the temperature of 0 to 40° C.

In addition, the deprotection reaction except the above described processes can be carried out, for example, by the process described in T. W. Greene, *Protective Groups in Organic Synthesis*, Wiley, New York, 1999.

The protection group for carboxyl includes, for example, methyl, ethyl, allyl, t-butyl, trichloroethyl, benzyl (Bn), phenacyl, p-methoxybenzyl, trityl, 2-chlorotrityl or structure thereof binded to solid phase carrier and so on.

The protection group for hydroxyl includes, for example, methyl, trytyl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc), and so on.

The protection group of amino includes benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), 2-(trimethylsilyl)ethoxymethyl (SEM) and so on.

The protection group of mercapto includes, for example, benzyl, methoxybenzyl, methoxymethyl (MOM), 2-tetrahydropyranyl (THP), diphenylmethyl, acetyl (Ac) and so on.

The protective group for carboxyl, hydroxyl, amino or mercapto is not particularly limited to the above described groups, so long as it can be easily and selectively left. For example, those described in T. W. Greene, *Protective Groups in Organic Synthesis*, Wiley, New York, 1999 can be used.

As will be easily understood by those skilled in the art, the intended compounds in the present invention can be easily prepared by choosing these deprotection reactions.

b) Among the compound represented by formula (I), the compound wherein X is a bond, Y is —C(=O)NR$^8$—, —C(=S)NR$^8$—, that is, the compound represented by formula (IB):

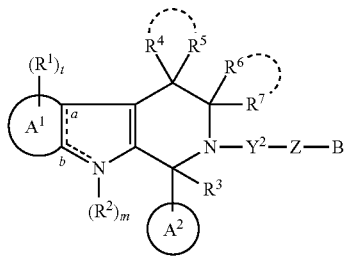

(IB)

(wherein, $Y^2$ is —C(=O)NR$^8$— or —C(=S)NR$^8$—, the other symbols have the same meanings as the described above) can be prepared by following processes.

The compound represented by formula (IB) can be prepared by reacting the compound represented by formula (IV):

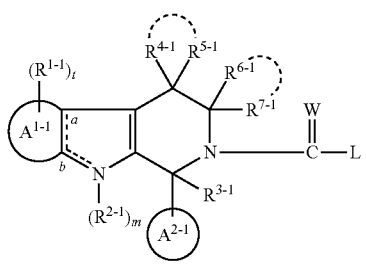

(IV)

(wherein, W is an oxygen atom or a sulfur atom, the other symbols have the same meanings as the described above) with the compound represented by formula (V):

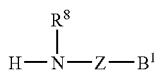

(V)

(wherein, all the symbols have the same meanings as the described above), if necessary, followed by subjecting to a deprotection reaction of protection group.

The reaction with the compound represented by formula (IV) and the compound represented by formula (V) is carried out, for example, by reacting the compound represented by formula (IV) with the compound represented by formula (V) in an organic solvent (e.g. chloroform, dichloromethane, diethylether, tetrahydrofuran etc.) under the presence of a base (e.g. pyridine, triethylamine, dimethylaniline, dimethylaminopyridine, diisopropylethylamine etc.) at a temperature from 0 degrees centigrade to reflux temperature.

Or, it is carried out by reacting the compound represented by formula (IV) with the compound represented by formula (V) in an organic solvent (e.g. dioxane, tetrahydrofuran, diethylether etc.) using alkali aqueous solution (e.g. sodium bicarbonate or sodium hydroxide solution etc.) at the temperature from 0 degrees centigrade to reflux temperature.

The deprotection reaction of the protective group can be carried out by the above described method.

The compound represented by formula (IB) can be prepared by reacting the compound represented by formula (II), the compound represented by formula (V) and the compound represented by formula (VI):

(VI)

(wherein, all the symbols have the same meanings as the described above), if necessary, followed by subjecting to a deprotection reaction of protection group.

The reaction with the compound represented by formula (II), the compound represented by formula (V) and the compound represented by formula (VI) is carried out, for example, by reacting the compound represented by formula (II), the compound represented by formula (V), the compound represented by formula (VI) (for example, phosgene compound (e.g. phosgene, thiophosgene, triphosgene(bis (trichloromethyl)carbonate) etc.), imidazole compound (e.g. CDI (carbonyldiimidazole), TCDI (thiocarbonylimidazole) etc.) in an organic solvent (e.g. ethyl acetate, chloroform, dichloromethane, diethylether, tetrahydrofuran, benzene, toluene etc.) or absence of solvent and under the presence of a base (e.g. pyridine, triethylamine, dimethylaniline, dimethylaminopyridine, diisopropylethylamine etc.) at a temperature from −20 degrees centigrade to reflux temperature.

This reaction is preferably carried out under the anhydrous condition in the presence of inert gases.

The deprotection reaction of the protective group can be carried out by the above described method.

c) Among the compound represented by formula (I), the compound wherein X is a bond, Y is —C(=O)NH—, —C(=S)NH—, that is, the compound represented by formula (IC):

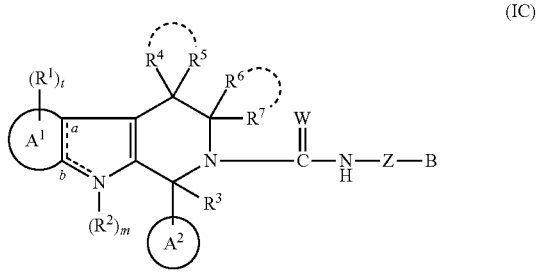

(IC)

(wherein, all the symbols have the same meanings as the described above) can be prepared by reacting the compound represented by formula (II) and the compound represented by formula (VII)

  (VII)

(wherein, all the symbols have the same meanings as the described above), if necessary, followed by subjecting to a deprotection reaction of protection group.

The reaction with the compound represented by formula (II) and the compound represented by formula (VII) is carried out, for example, by reacting the compound represented by formula (II) with the compound represented by formula (VII)

in an organic solvent (e.g. toluene, benzene, xylene, tetrahydrofuran, dichloromethane, diethylether, 1,2-dichloroethane, N,N-dimethylformamide etc.) at a temperature from 0 degrees centigrade to reflux temperature.

This reaction is preferably carried out under the anhydrous condition in the presence of inert gases.

The deprotection reaction of the protective group can be carried out by the above described method.

d) Among the compounds represented by formula (I), the compound wherein A is a heterocyclic ring containing at least one nitrogen atom, X is C1-3 alkylene which may have a substituent(s), C2-3 alkenylene which may have a substituent(s), C2-3 alkynylene which may have a substituent(s), Y is —C(=O)—, —C(=O)NR$^8$—, —SO$_2$—, —C(=O)O—, —SO$_2$NR$^8$—, that is, the compound represented by formula (ID):

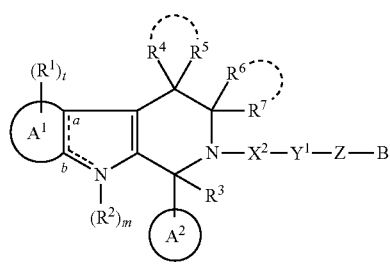

(ID)

(wherein, $X^2$ is C1-3 alkylene which may have a substituent(s), C2-3 alkenylene which may have a substituent(s) or C2-3 alkynylene which may have a substituent(s), the other symbols have the same meanings as the described above) can be prepared by the following process.

The compound represented by formula (ID) can be prepared by reacting the compound represented by formula (II) and the compound represented by formula (VIII):

$$L^1\text{-}X^2\text{—}Y^1\text{—}Z\text{—}B^1 \qquad \text{(VIII)}$$

(wherein, $L^1$ is a halogen atom, the other symbols have the same meanings as the described above), if necessary, followed by subjecting to a deprotection reaction of protection group.

The reaction with the compound represented by formula (II) and the compound represented by formula (VIII) is carried out, for example, in an organic solvent (e.g. tetrahydrofuran, dichloromethane, chloroform, benzene, toluene, xylene, hexane, heptane, cyclohexane, diethylether, dioxane, acetone, ethylmethylketone, acetonitrile, dimethylsulfoxide, N,N-dimethylformamide, dimethylacetamide, ethyl acetate etc.), under the presence of a base (e.g. potassium carbonate, sodium carbonate, cesium carbonate, sodium hydride etc.), and under the presence or the absence of a catalyst (e.g. potassium iodide, sodium iodide, tetrabutyl ammonium iodide etc) at a temperature from 0 degrees centigrade to reflux temperature.

The deprotection reaction of the protective group can be carried out by the above described method.

e) Among the compound represented by formula (I), the compound wherein X is a bond, Y is —C(=O)—, or —C(=S)—, that is, the compound represented by formula (IE):

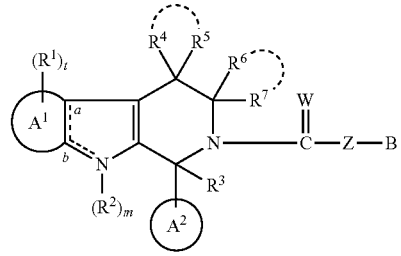

(IE)

(wherein, all the symbols have the same meanings as the described above) can be prepared by the following process.

The compound represented by formula (IE) can be prepared by the compound represented by formula (II) and the compound represented by formula (IX):

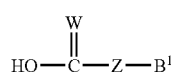

(IX)

(wherein, all the symbols have the same meanings as the described above), if necessary, followed by subjecting to a deprotection reaction of protection group.

The reaction with the compound represented by formula (II) and the compound represented by formula (XI) is carried out, for example, by the method (1) using acid halide, (2) using mixed acid anhydride, (3) using condensing agent etc.

These methods are explained concretely as follows.

(1) The method using acid halide is carried out, for example by reacting the compound represented by formula (XI) in an organic solvent (e.g. chloroform, dichloroform, diethylether, tetrahydrofuran, dimethoxyethane etc.) or the absence of solvent, with acid halide agent (e.g. oxalylchloride, thionylchloride etc.) at the temperature from −20 degrees centigrade to reflux temperature, and reacting the obtained acid halide with the compound represented by formula (II) in a organic solvent (e.g. chloroform, dichloromethane, diethylether, tetrahydrofuran, acetonitrile, ethyl acetate etc.) under the presence of a base (e.g. pyridine, triethylamine, dimethylaniline, dimethylaminopyridine, diisopropylethylamine etc.) at the temperature of from 0 to 40 degrees centigrade. In addition, it is carried out by reacting the obtained halide with the compound represented by formula (II) in an organic solvent (e.g. dioxane, tetrahydrofuran, dichloromethane etc.), under the presence or absence of phase-transfer catalyst (e.g. quaternary ammonium salt etc., for example, tetrabutylammoniumchloride, triethylbenzylammoniumchloride, tri n-octylmethylammoniumchloride, trimethyldecylammoniumchloride, tetramethylammoniumbromide and so on), using alkaline solution (e.g. sodium bicarbonate or sodium hydroxide solution etc.) at the temperature from 0 to 40 degrees centigrade.

(2) The method using mixed acid anhydride is carried out, for example the compound represented by formula (XI) with an acid halide (e.g. pivaloyl chloride, tosyl chloride, mesyl chloride etc.), or an acid derivative (e.g. chloroethyl formate, chloroisobutyl formate etc.) in an organic solvent (e.g. chloroform, dichloromethane, diethylether, tetrahydrofuran etc.) or the absence of solvent, under the presence of a base (e.g. pyridine, triethylamine, dimethylaniline, dimethylaminopyridine, diisopropylethylamine etc.) at the temperature from 0 to 40 degrees centigrade, and by reacting the obtained mixed acid anhydride with the compound represented by formula (II) in an organic solvent (e.g. chloroform, dichloromethane, diethylether, tetrahydrofuran etc.) at the temperature from 0 to 40 degrees centigrade.

(3) The method using condensing agent is carried out, for example by reacting the compound represented by formula (XI) with the compound represented by formula (II) in an organic solvent (e.g. chloroform, dichloromethane, dimethylformamide, diethylether, tetrahydrofuran etc.), or in the absence of solvent, under the presence or the absence of a base (e.g. pyridine, triethylamine, dimethylaniline, dimethylaminopyridine etc.) using the condensing agent (e.g. 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodine, 1-propanephosphonic acid cyclic anhydride (PPA) etc.), using or not using 1-hydroxybenztriazole (HOBt) at the temperature from 0 to 40 degrees centigrade.

These reactions (1), (2) and (3) are all preferably carried out under the anhydrous condition in the presence of inert gases (argon, nitrogen etc.).

The deprotection reaction of the protective group can be carried out by the above described method.

The compounds represented by formula (II), (III), (IV), (V), (VI), (VII), (VIII) and (IX) used as starting materials or reagents can be easily prepared by the known processes, the processes shown in following Examples, or the known processes, for example, processes described in "*Comprehensive Organic Transformations: A Guide to Functional Group Preparations,* 2nd Edition", "Richard C. Larock, John Wiley & Sons Inc, 1999".

In each reaction in the present specification, as will be understood by those skilled in the art, the reaction with heating can be effected using water bath, oil bath, sand bath or microwave.

In each reaction in the present specification, solid-phase supported reagent accordingly supported to macromolecule polymer (e.g. polystyrene, polyacrylamide, polypropylene, polyethyleneglycol etc.) may be used.

In each reaction in the present specification, reaction products may be purified in an ordinary manner, for example, through normal-pressure or reduced-pressure distillation, or through high-performance liquid chromatography with silica gel or magnesium silicate, thin-layer chromatography, or column chromatography, ion-exchange resin, scavenger resin or through washing or recrystallization and so on. The purification may be effected in each reaction or after some reactions

[Toxicity]

Toxicity of the compound represented by formula (I) is very low, and it is safe enough to use as a pharmaceutical agent.

[Application to Pharmaceutical Preparations]

The compound represented by formula (I), a salt thereof, an N-oxide thereof, a solvate thereof or a prodrug thereof (hereinafter, it is abbreviated to the compound of the present invention) is useful for a preventive and/or therapeutic agent for the above described diseases caused by stress in mammals (e.g. human, non-human animal (e.g. monkey, sheep, cow, horse, dog, cat, rabbit, rat, mouse etc.) etc.). The compound of the present invention is useful for a preventive and/or therapeutic agent for, particularly, digestive system disease caused by stress (irritable bowel syndrome, ulcerative colitis, Crohn's disease etc.).

The compounds of the present invention may be administered in combination with other pharmaceutical preparations for the purpose of 1) complement and/or enhancement of preventing and/or treating effect of the compounds of the present invention, 2) improvement of dynamics/absorption and lowering of dose of the compounds of the present invention and/or 3) alleviation of side effect of the compounds of the present invention.

The compounds of the present invention and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compounds of the present invention may be administered before the other pharmaceutical preparations. Alternatively, the other pharmaceutical preparations may be administered before the compounds of the present invention. The method for the administration of these pharmaceutical preparations may be same or different.

The other pharmaceutical preparations may be low-molecular compounds. In addition, they may be macromolecular protein, polypeptide, polynucleotide (DNA, RNA, and gene), antisense, decoy, antibody or vaccine and so on. The dose of the other pharmaceutical preparations can be accordingly selected as a standard of clinical dose. Additionally, the compounding ratio of the compounds of the present invention and the other pharmaceutical preparations can be accordingly selected by the age and body weight of administering object, the administration method, the administration time, the object disease, the symptom, the combination etc. For example, the other pharmaceutical preparations may be used from 0.01 to 100 parts by weight relative to 1 part by weight of the compounds of the present invention. The other pharmaceutical preparations may be administered at appropriate ratio combining one or more arbitrarily selected from the homogeneous groups or heterogeneous groups as follows. The other pharmaceutical preparations do not only include ones which have ever been found but ones which will be found from now based on the above described mechanism.

The other pharmaceutical preparations which may combine the compounds of the present invention include, for example, antianxiety drugs (e.g. benzodiazepine drugs, thienodiazepine drugs, non-benzodiazepine drugs, serotonergic drugs, CRF antagonists, tachykinin $NK_1$ antagonists etc.), antidepressants (e.g. tricyclic antidepressants, tetracyclic antidepressants, monoamine release drugs, monoamine oxidase inhibitors, monoamine reuptake inhibitors (SSRI, SNRI), CRF antagonists, tachykinin $NK_1$ antagonists, neurotensin antagonists etc.), antiparkinson drugs (e.g. anticholinergic drugs, dopamine agonists, monoamine oxidase inhibitors, etc.), schizophrenia drugs (e.g. dopamine antagonists, etc.), antiepileptic drugs (e.g. barbituric acid series, hydantoin series etc.), anti vertigo drugs, asthmatic drugs (e.g. bronchodilators, α receptor agonists, $β_2$ receptor agonists, xanthine series, inhaled steroids, anticholinergic drugs, 5-lipoxygenase inhibitors etc.), peptic ulcer drugs (e.g. offensive factor inhibitors, antipeptic drugs, antacids, histamine-$H_2$ receptor antagonists, anti gastrin drugs, proton pump inhibitors, muscarine receptor inhibitors, anticholinergic drugs, defensive factor enhancers, prostaglandin derivatives, etc.), gastrointestinal tract function regulators (e.g. intestinal remedies, CCK-A antagonists, neurotensin antagonists, opioid agonists, muscarine receptor agonists, $5-HT_4$ agonists, $5-HT_3$ antagonists etc.), gastrointestinal tract prokinetic drugs (e.g. intestinal remedies, CCK-A antagonists, neurotensin antagonists, opioid agonists, muscarine receptor agonists, $5-HT_4$ agonists, $5-HT_3$ antagonists etc.), antidiarrheals (e.g. antidiarrheal drugs, opioid μ receptor stimulators, etc.), evacuants (e.g. bulk laxatives, saline laxatives, stimulant laxatives, affinity polyacrylic resin etc.), antihypertensive drugs (e.g.

calcium antagonists, β receptor blockers, α₁ receptor blockers, angiotensin converting enzyme inhibitors, angiotensin II receptor blockers, etc.), antiarrhythmic drugs (e.g. sodium inhibitors, β receptor blockers, potassium antagonists, calcium antagonists, etc.), cardiac stimulants (e.g. phosphodiesterase inhibitors, cardiac glycosides, β receptor agonists etc.), dysuria remedies (e.g. frequent urination remedies, anticholinergic drugs, muscarine agonists (antagonists), tachykinin $NK_1$ antagonists, $NK_2$ antagonists, etc.) and so on.

The diseases on which the preventive and/or therapeutic effect works with the above described combination drugs are not especially limited. The diseases may be those which compensate for and/or enhance the preventive and/or therapeutic effect of the compounds of the present invention.

The other pharmaceutical preparations to compensate and/or enhance for preventive and/or therapeutic effect on irritable bowel syndrome of the compounds of the present invention include, for example, antianxiety drugs (e.g. benzodiazepine drugs, thienodiazepine drugs, non-benzodiazepine drugs, serotonergic drugs, CRF antagonists etc.), antidepressants (e.g. monoamine release drugs, monoamine oxidase inhibitors, monoamine reuptake inhibitors (SSRI, SNRI), CRF antagonists, neurotensin antagonists, tricyclic antidepressants, tetracyclic antidepressants, etc.), anticholinergic drugs, gastrointestinal tract function regulators (e.g. intestinal remedies, CCK-A antagonists, neurotensin antagonists, opioid agonists, muscarine receptor agonists, $5-HT_4$ agonists, $5-HT_3$ antagonists etc.), gastrointestinal tract prokinetic drugs (e.g. intestinal remedies, CCK-A antagonists, neurotensin antagonists, opioid agonists, muscarine receptor agonists, $5-HT_4$ agonists, $5-HT_3$ antagonists etc.), antidiarrheals (e.g. antidiarrheal drugs, opioid μ receptor stimulators, etc.), evacuants (e.g. bulk laxatives, saline laxatives, stimulant laxatives, affinity polyacrylic resin etc.), mucosal paralytic drugs, autonomic nerve modulators, calcium antagonists, phosphodiesterase inhibitors, serotonin antagonists (e.g. $5-HT_3$ antagonists, $5-HT_4$ antagonists etc.), darifenacyn, polycarbophil calcium and so on.

The other pharmaceutical preparations to compensate and/or enhance for preventive and/or therapeutic effect on gastric ulcer and duodenal ulcer of the compounds of the present invention include, for example, peptic ulcer drugs (e.g. offensive factor inhibitors, antipeptic drugs, antacids, histamine-$H_2$ receptor antagonists, anti gastrin drugs, proton pump inhibitors, muscarine receptor inhibitors, anticholinergic drugs, defensive factor enhancers, prostaglandin derivatives, mesalazine, salazosulfapyridine, etc.), anticholinergic drugs, gastric mucosal paralytic drugs, antianxiety drugs (e.g. benzodiazepine drugs, thienodiazepine drugs, non-benzodiazepine drugs, serotonergic drugs, CRF antagonists, etc.), dopamine antagonists and so on.

The other pharmaceutical preparations to compensate and/or enhance for preventive and/or therapeutic effect on ulcerative colitis of the compounds of the present invention include, for example, mesalazine, salazosulfapyridine, peptic ulcer drugs (e.g. offensive factor inhibitors, antipeptic drugs, antacids, histamine-$H_2$ receptor antagonists, anti gastrin drugs, proton pump inhibitors, muscarine receptor inhibitors, anticholinergic drugs, defensive factor enhancers, prostaglandin derivatives, etc.), anticholinergic drugs, steroids, 5-lipoxygenase inhibitors, antioxidant drugs, $LTB_4$ antagonists, local anesthetics, immunosuppressive drugs, defensive factor enhancers, metalloprotease inhibitors and so on.

The other pharmaceutical preparations to compensate and/or enhance for preventive and/or therapeutic effect on biliary tract dyskinesia of the compounds of the present invention include, for example, ceruleins, antispasmodic drugs, COMT (catechol-O-methyltransferase) inhibitors, cholinergic agonists, anticholinergic drugs, antianxiety drugs, cholagogues, antidepressants, CCK-A antagonists and so on.

The other pharmaceutical preparations to compensate and/or enhance for preventive and/or therapeutic effect on aerophagy of the compounds of the present invention include, for example, intestinal remedies, antianxiety drugs, autonomic nerve modulators, fiber formulations, digestive enzymes, gas absorbent drugs, intestinal tract prokinetic drugs and so on.

The other pharmaceutical preparations to compensate and/or enhance for preventive and/or therapeutic effect on chronic hepatitis of the compounds of the present invention include, for example, liver hydrolysate formulations, polyenephosphatidylcholine, glycyrrhizin formulations, protoporphyrin sodium, ursodeoxycholic acid, steroids, anticholinergic drugs, antacids, propagermanium, lipid peroxidase inhibitors and so on.

The other pharmaceutical preparations to compensate and/or enhance for preventive and/or therapeutic effect on chronic pancreatitis of the compounds of the present invention include, for example, protease inhibitors, gastric acid inhibitors, antispasmodic drugs (e.g. COMT inhibitors, anti serotonin drugs etc.), nonsteroidal anti-inflammatory drugs, central analgesics, sedatives, digestive enzymes, antacids, histamine $H_2$ receptor inhibitors, antidepressants, gastric mucosa local anesthetics, gastrointestinal tract function regulators (CCK-A antagonists) and so on.

The other pharmaceutical preparations to compensate and/or enhance for preventive and/or therapeutic effect on esophageal spasm of the compounds of the present invention include, for example, esophageal prokinetic drugs, antidepressants, autonomic nerve modulators and so on.

The other pharmaceutical preparations to compensate and/or enhance for preventive and/or therapeutic effect on gastric atony of the compounds of the present invention include, for example, gastrointestinal tract prokinetic drugs, digestive enzymes, tranquilizers and so on.

The other pharmaceutical preparations to compensate and/or enhance for preventive and/or therapeutic effect on functional dyspepsia of the compounds of the present invention include, for example, antacids, histamine $H_2$ receptor inhibitors, gastrointestinal tract function regulators, gastrointestinal tract prokinetic drugs, antidepressants, tranquilizers, digestive enzymes, proton pump inhibitors, muscarine receptor inhibitors, anticholinergic drugs, defensive factor enhancers, dopamine antagonists and so on.

Antianxiety drugs include, for example, diazepam, oxazolam, flunitrazepam, alprazolam, etizolam, flutazolam, lorazepam, ethyl loflazepate, tofisopaam, clotiazepaam, γoryzanol and so on.

Tricyclic antidepressants include, for example, amitriptyline, imipramine, clomipramine, nortriptyline, desipramine, amoxapine and so on.

Tetracyclic antidepressants include, for example, mianserin, maprotiline and so on.

Monoamine oxidase inhibitors include, for example, trazodone, fluvoxamine and so on.

Antiparkinson drugs include, for example, levodopa, amantadine, selegiline, bromocriptine, pramipexole, anticholinergic drug and so on.

Anticholinergic drugs include, for example, trihexyphenidyl, biperiden, ipratropium bromide, mepenzolate bromide and so on.

Antiepileptic drugs include, for example, phenobarbital, phenyloin, carbamazepine, valproic acid, clonazepam and so on.

Anti vertigo drugs include, for example, difenidol, βhistine and so on.

Asthmatic drugs include, for example, ephedrine, orciprenaline, salbutamol, procaterol, theophylline, aminophylline, disodium cromoglycate, anticholinergic drug, inhaled steroid and so on.

Inhaled steroids include, for example, beclomethasone, prednisolone and so on.

Antipeptic drugs include, for example, sucralfate and so on.

Antacids include, for example, sodium bicarbonate, magnesium oxide, dry aluminum hydroxide gel, aluminum silicate and so on.

Histamine $H_2$ receptor antagonists include, for example, famotidine, ranitidine, cimetidine, roxatidine and so on.

Anti gastrin drugs include, for example, proglumide and so on.

Proton pump inhibitors include, for example, omeprazole, lansoprazole and so on.

Muscarine receptor inhibitors include, for example, pirenzepine and so on.

Defensive factor enhancers include, for example, gefamate, teprenone, sucralfate, aldioxa, cetraxate hydrochloride, ornoprostil and so on.

Prostaglandin derivatives include, for example, ornoprostil, misoprostol and so on.

Gastrointestinal tract function regulators include, for example, cisapride, domperidone, sulpiride, metoclopramide, alosetron, trimebutine maleate and so on.

Gastrointestinal tract prokinetic drugs include, for example, cisapride, tegaserod, bethanechol hydrochloride and so on.

Antidiarrheals include, for example, loperamide and so on.

Bulk laxatives include, for example, methylcellulose, carmellose, lactulose and so on.

Saline laxatives include, for example, magnesium sulfate, magnesium oxide and so on.

Stimulant laxatives include, for example, picosulfate, lactulose, castor oil, senna, rhubarb and so on.

Antihypertensive drugs include, for example, nicardipine, nifedipine, nilvadipine, atenolol, allotynol, carteolol, propranolol, metoprolol, prazosin, captopril, enalapril, candesartan cilexetil, losartan potassium and so on.

Antiarrhythmic drugs include, for example, quinidine, procainamide, disopyramide, lidocaine, mexiletine, propranolol, amiodarone, verapamil and so on.

Cardiac stimulants include, for example, digitoxin, digoxin, dopamine, dobutamine, aminophylline, mirnoline and so on.

Dysuria remedies include, for example, oxybutynin, tamsulosin, propiverine and so on.

Local anesthetics include, for example, lidocaine, oxethazaine, procaine hydrochloride, dibucaine hydrochloride, cocaine hydrochloride, tetracaine hydrochloride and so on.

Immunosuppressive drugs include, for example, cyclosporine, tacrolimus, azathiopurine, FTY720 and so on.

Autonomice nerve modulators include, for example, γorizanol and so on.

Cholagogues include, for example, ursodeoxycholic acid and so on.

Tachykinin $NK_1$ antagonists include, for example, aprepitant, TAK-637, Z-501 and so on.

Serotonin antagonists include, for example, YM060, tegaserod, alosetron and so on.

In order to use the compounds of the present invention, or the compounds of the present invention in combination with the other pharmaceutical preparations by the above described purpose, these compounds are normally administered to the entire of human body or topically, and orally or parenterally.

The dose of the compounds of the present invention depends on age, body weight, symptom, therapeutic effect, the administration method, the treatment time and so on. In practice, however, these compounds are administered orally once or several times per day each in an amount of from 100 μg to 1000 mg per adult, parentally once or several times per day each in an amount of from 50 μg to 500 mg per adult or continuously administered into vein for 1 hour to 24 hours per day.

It goes without saying that the dose of these compounds may be less than the above described dose or may need to exceed the above described range because the dose varies under various conditions as described above.

When the compounds of the present invention, or the compounds of the present invention are administered in combination with the other pharmaceutical preparations, they are used in the form of solid or liquid agent for oral administration, injection, agent for external application, suppository, eye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch etc.), binder (e.g., hydroxypropyl cellulose, polyvinyl pyrrolidone, magnesium metasilicoaluminate etc.), disintegrant (e.g., calcium fibrinoglycolate etc.), glidant (e.g., magnesium stearate etc.), stabilizer, dissolution aid (e.g., glutamic acid, aspartic acid etc.) or the like. The solid agent may be coated with a coating agent (e.g., white sugar, gelatin, hydroxypropyl cellulose, hydroxypropyl methyl cellulose phthalate etc.) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof etc.). Furthermore, such a liquid agent may comprise a wetting agent, a suspending agent, an emulsifier, a sweetening agent, a flavor, a fragrance, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester etc.), wax (e.g., beeswax, whale wax, ceresin etc.), surface active agent (e.g., polyoxyethylenealkylether phosphoric acid ester etc.), higher alcohol (e.g., cetanol, stearyl alcohol, setostearyl alcohol etc.), silicon oil (e.g., dimethyl polysiloxane etc.), hydrocarbon (e.g., hydrophilic petrolatum, white petrolatum, purified lanolin, liquid paraffin etc.), glycol (e.g., ethylene glycol, diethylene glycol, propylene glycol, polyethylene glycol, macrogol etc.), vegetable oil (e.g., castor oil, olive oil, sesame oil, turpentine oil), animal oil (mink oil, vitelline oil, squalane, squalene), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol etc.), gelling agent (e.g., carboxymethyl cellulose, hydroxyethyl cellulose, hydroxypropyl cellulose, ethyl cellulose etc.), neutralizing agent (e.g., triethanolamine, diisopropanolamine etc.), surface active agent (e.g., polyethylene glycol monostearate etc.), gums, water, absorption accelerator, and rash preventive are used singly or in admixture of two or more thereof. The gel base may further comprise a preservative, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol etc.), higher alcohol (e.g., 2-hexyl decanol, cetanol etc.), emulsifier (e.g., polyoxyethylene alkyl ethers, aliphatic acid esters etc.), water, absorption accelerator, and rash preventive are used singly or in admixture of two or more thereof. The cream base may further comprise a preservative, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose etc.), wetting agent (e.g., urea, glycerin, propylene glycol etc.), filler (e.g., kaolin, zinc oxide, talc, calcium, magnesium etc.), water, dissolution aid, tackifier, and rash preventive may be used singly or in admixture of two or more thereof. The wet compress base may further comprise a preservative, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a preservative, an antioxidant, a perfume, etc.

The liniment is prepared by any known or commonly used formulation. For example, one or more active materials are dissolved, suspended or emulsified in water, alcohol (e.g., ethanol, polyethylene glycol etc.), higher aliphatic acid, glycerin, soap, emulsifier, suspending agent, etc., singly or in combination of two or more thereof, to prepare such a liniment. The liniment may further comprise a preservative, an antioxidant, a perfume, etc.

The nebula, inhalant, spray and aerozol each may comprise a commonly used diluent, additionally, a stabilizer such as sodium hydrogen sulfite and a buffer capable of providing isotonicity such as isotonic agent (e.g., sodium chloride, sodium citrate, or citric acid etc.). For the process for the preparation of spray, reference can be made to U.S. Pat. Nos. 2,868,691 and 3,095,355.

The injection for parenteral administration consists of solid injection used to be dissolved or suspended in the form of solution, suspension, emulsion and a solvent to be dissolved before use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination thereof. The injection may further comprise a stabilizer, a dissolution aid (e.g., glutamic acid, aspartic acid, Polysolvate 80 (trade name) etc.), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in aseptic distilled water for injection or other solvents before use.

The eye drops for parenteral administration consist of eye drop, suspension eye drop, emulsion eye drop, eye drop to be dissolved before use and ointment and so on.

These eye drops are prepared by a known method. For example, it is prepared by dissolving, suspending or emulsifying one or more active materials in a solvent. As such a solvent for eye drops there may be used distilled water, physiological saline, the other aqueous solvent or nonaqueous solvent for injection (e.g. vegetable oil etc.), etc., singly or in combination thereof. The eye drops may comprise, if necessary, of materials properly selected from tonisity agent (e.g. sodium chloride, concentrated glycerin etc.), buffer agents (e.g. sodium phosphate, sodium acetate etc.), surfactants (e.g. polysorbate 80 (trade name), polyoxyl 40 stearate, polyoxyethylene hydrogenated castor oil etc.), stabilizer (e.g. sodium citrate, sodium edentate etc.), antiseptic agent (e.g. benzalkonium chloride, paraben etc.) These are sterilized at the final step or prepared by an aseptic process. Alternatively, an aseptic solid agent such as freeze-dried product which has previously been prepared may be rendered aseptic or dissolved in aseptic distilled water for injection or other solvents before use.

The inhalant for parenteral administration may be in the form of aerosol, powder for inhalation or liquid for inhalation. The liquid for inhalation may be dissolved or suspended in water or other proper medium in use.

These inhalants are prepared by a known method.

For example, the liquid for inhalation is prepared from materials properly selected from preservatives (e.g., benzalconium chloride, Paraben etc.), colorants, buffering agents (e.g., sodium phosphate, sodium acetate etc.), isotonic agents (e.g., sodium chloride, concentrated glycerin etc.), thickening agents (e.g., carboxyvinyl polymer etc.), absorption accelerators, etc. as necessary.

The powder for inhalation is prepared from materials properly selected from glidants (e.g., stearic acid and salt thereof etc.), binders (e.g., starch, dextrin etc.), vehicles (e.g., lactose, cellulose etc.), colorants, preservatives (e.g., benzalconium chloride, Paraben etc.), absorption accelerators, etc., if necessary.

In order to administer the liquid for inhalation, a sprayer (e.g., atomizer, nebulizer etc.) is normally used. In order to administer the powder for inhalation, a powder inhaler is normally used.

Other examples of the composition for parenteral administration include suppository for rectal administration and pessary for vaginal administration prepared by an ordinary formulation comprising one or more active materials.

Effect of the Invention

The compound of the present invention represented by formula (I) has an affinity to MBR and further anti stress action. Among the compound of the present invention represented by formula (I), since the compound of which ring $A^2$ has two substituents, that is, the compound of the present invention represented by formula (I-B-1-2) has a strong affinity to MBR, shows strong anti stress action and superior to oral absorption, it is useful as a preventive and/or therapeutic agent for diseases caused by stress, especially, digestive system diseases caused by stress.

BEST MODE OF THE CARRYING OUT THE INVENTION

Figure 1:
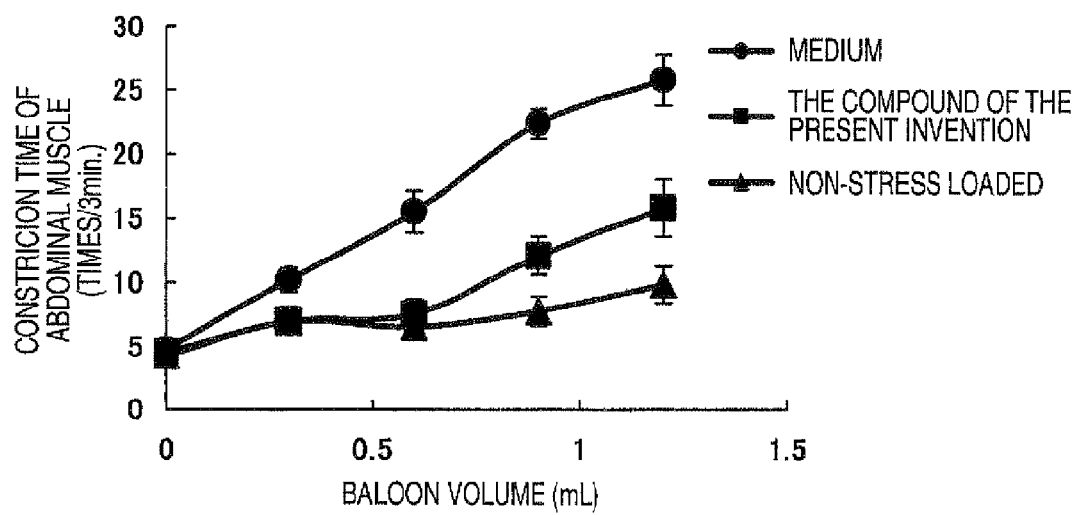
FIG. 1 is a graph which shows a suppressive action for abdominal pain of the compound of the present invention in RCS loaded model.

The present invention is explained below in detail base on Examples, however, the present invention is not limited thereto. The solvents in parentheses at chromatographic separations section and TLC section show the developing or eluting solvents and the ratios of the solvents used are indicated by volume. The solvents in parentheses indicated in NMR section show solvents used in determination.

All compounds described in the specification are named by using of ACD/Name (Trade mark, Advanced Chemistry Development Inc.) or ACD/Name batch (Trade mark, Advanced Chemistry Development Inc.) which is the computer program to name according to IUPAC rule, or according to IUPAC organic chemistry nomenclature.

Example 1

1-(1H-indole-3-yl)cyclopropanecarbonitrile 1H-indole-3-ylacetonitrile (18.7 g) was dissolved in tetrahydrofuran (240 mL) and, after cooling to −30° C., lithium diisopropylamide (2.0M heptane/tetrahydrofuran/ethylbenzene solution, 240 mL) was added dropwise, followed by stirring at −5° C. for 30 minutes. The reaction mixture was cooled to −30° C. and 1-bromo-2-chloroethane (11.0 mL) was added dropwise, followed by stirring for 2 hours while heating to 0° C. The reaction mixture was poured into ice/hydrochloric acid (2N, 360 mL) and extracted with ethyl acetate. The organic layer was washed in turn with water, an aqueous saturated sodium hydrogen carbonate solution and saturated saline, dried over anhydrous magnesium sulfate and then concentrated. The residue was purified by silica gel column chromatography (hexane:ethyl acetate=3:1) to obtain a compound and the compound was recrystallized from (hexane:ethyl acetate=1:1) to obtain the titled compound having the following physical properties (8.67 g).

TLC: Rf 0.43 (hexane:ethyl acetate=2:1);
$^1$H NMR (CDCl$_3$): δ 1.30-1.43 (m, 2H), 1.60-1.75 (m, 2H), 7.11 (d, J=2.74 Hz, 1H), 7.16-7.32 (m, 2H), 7.33-7.45 (m, 1H), 7.72-7.90 (m, 1H), 8.11 (s, 1H).

Example 2

[1-(1H-indole-3-yl)cyclopropyl]methylamine

To an anhydrous tetrahydrofuran (35 mL) suspension of lithium aluminum hydride (1.07 g), an anhydrous tetrahydrofuran (12 mL) solution of a compound (1.71 g) prepared by Example 1 was added dropwise at 80° C., followed by stirring at 80° C. until materials disappear. The reaction mixture was air-cooled to room temperature and water (1 mL), an aqueous 5N sodium hydroxide solution (1 mL) and water (3 mL) were sequentially added under ice cooling, followed by stirring at room temperature. The reaction mixture was filtered with Celite (trade name) and the filtrate was concentrated to obtain the titled compound having the following physical properties (2.0 g). The compound was used for the following reaction without being purified.

TLC: Rf 0.51 (dichloromethane:methanol:28% ammonia water=9:1:0.1);
$^1$H NMR (CDCl$_3$): δ 0.70-0.78 (m, 2H), 0.79-0.88 (m, 2H), 2.80 (s, 2H), 7.07 (d, J=2.38 Hz, 1H), 7.09-7.16 (m, 1H), 7.17-7.24 (m, 1H), 7.32-7.38 (m, 1H), 7.71-7.80 (m, 1H).

Example 3

1-(1,3-benzodioxol-5-yl)-1,2,3,9-tetrahydrospiro[β-carboline-4,1'-cyclopropane]

To an acetic acid (2 mL) solution of the compound (220 mg) prepared in Example 2, 1,3-benzodioxol-5-carboaldehyde (186 mg) was added at room temperature, followed by stirring at 70 to 100° C. until materials disappear. The reaction mixture was concentrated. The residue was dissolved in ethyl acetate and the solution was washed in turn with an aqueous saturated sodium hydrogen carbonate solution and saturated saline, dried over anhydrous sodium sulfate and then concentrated. The residue was purified by silica gel column chromatography (hexane:ethyl acetate=1:2) to obtain the titled compound having the following physical properties (308 mg).

TLC: Rf 0.1 (hexane:ethyl acetate=1:2);
$^1$H NMR (CDCl$_3$): δ 0.70-0.80 (m, 1H), 0.81-0.91 (m, 1H), 1.37-1.50 (m, 1H), 1.54-1.70 (m, 1H), 2.78 (d, J=13.17 Hz, 1H), 3.19 (d, J=13.17 Hz, 1H), 5.16 (s, 1H), 5.95 (s, 2H), 6.75-6.87 (m, 3H), 6.98-7.06 (m, 1H), 7.06-7.15 (m, 1H), 7.20-7.29 (m, 1H), 7.34 (d, J=7.68 Hz, 1H), 7.52 (s, 1H).

Example 4

2-acetyl-1-(1,3-benzodioxol-5-yl)-1,2,3,9-tetrahydrospiro[β-carboline-4,1'-cyclopropane]

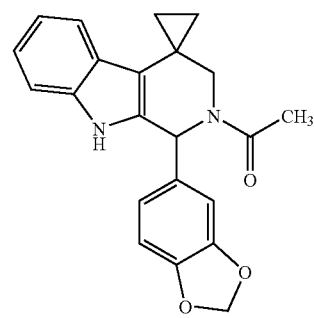

To a pyridine (1 mL) solution of the compound (103 mg) prepared in Example 3, acetic anhydride (98 μL) was added, followed by stirring at room temperature until materials disappear. The reaction mixture was diluted with ethyl acetate, washed in turn with 1N hydrochloric acid and an aqueous saturated sodium hydrogen carbonate solution, dried over anhydrous sodium sulfate and then concentrated. The residue was washed with tert-butyl methyl ether and then collected by filtration to obtain the titled compound having the following physical properties (83 mg).

TLC: Rf 0.10 (hexane:ethyl acetate=2:1);
$^1$H NMR (DMSO-$d_6$): δ 0.73-0.86 (m, 1H), 1.03-1.14 (m, 2H), 1.54-1.67 (m, 1H), 2.09 (s, 3 H), 3.23 (d, J=14.64 Hz, 1H), 3.58 (d, J=14.64 Hz, 1H), 5.98 (d, J=0.73 Hz, 1H), 5.99 (d, J=0.73 Hz, 1H), 6.62 (dd, J=8.05, 1.65 Hz, 1H), 6.76 (d, J=1.65 Hz, 1H), 6.81 (s, 1H), 6.86 (d, J=7.87, 1H), 6.91 (m, 1H), 7.03 (m, 1H), 7.23 (d, J=7.87 Hz, 1H), 7.28 (d, J=8.05 Hz, 1H), 11.03 (s, 1H).

Example 5

1-(1,3-benzodioxol-5-yl)-N-(3,5-dimethylphenyl)-1, 9-dihydrospiro[β-carboline-4,1'-cyclopropane]-2 (3H)-carboxamide

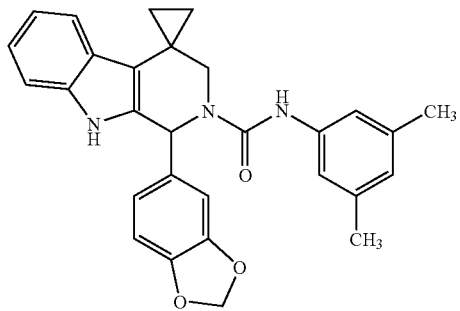

To an anhydrous tetrahydrofuran (3 mL) solution of the compound (92 mg) prepared in Example 3, 1-isocyanato-3, 5-dimethylbenzene (45 μL) was added, followed by stirring at room temperature until materials disappear. Hexane was added to the reaction mixture and the precipitate was collected by filtration. The resulting product obtained by filtration was dissolved in methanol and then concentrated to obtain the titled compound having the following physical properties (100 mg).

TLC: Rf 0.50 (hexane:ethyl acetate=2:1);
$^1$H NMR (DMSO-$d_6$): δ 0.66-0.82 (m, 1H), 0.97-1.23 (m, 2H), 1.50-1.71 (m, 1H), 2.20 (s, 6 H), 3.44 (d, J=14.64 Hz, 1H), 3.59 (d, J=14.64 Hz, 1H), 5.98 (d, J=0.91 Hz, 1H), 5.99 (d, J=0.91 Hz, 1H), 6.60 (s, 1H), 6.65 (dd, J=8.14, 1.56 Hz, 1H), 6.68 (s, 1H), 6.78 (d, J=1.46 Hz, 1 H), 6.84-6.96 (m, 2H), 6.99-7.06 (m, 1H), 7.10 (s, 2H), 7.23 (d, J=7.68 Hz, 1H), 7.29 (d, J=7.87 Hz, 1H), 8.43 (s, 1H), 11.04 (s, 1H).

Example 6 (1) to Example 6 (21)

Using 1H-indole-3-ylacetonitrile or alternatively a corresponding nitrile derivative thereof, a corresponding aldehyde derivative in place of 1,3-benzodioxol-5-carboaldehyde, and acetic anhydride or alternatively a corresponding acid halide, the operation having the same purpose as that in Example 1→Example 2→Example 3→Example 4 was conducted to obtain the following compound.

Example 6 (1)

2-acetyl-1-(2,6-difluorophenyl)-1,2,3,9-tetrahydrospiro[β-carboline-4,1'-cyclopropane]

TLC: Rf 0.16 (hexane:ethyl acetate=2:1);
$^1$H NMR (DMSO-$d_6$): δ 0.79-0.93 (m, 1H), 0.97-1.17 (m, 2H), 1.60-1.72 (m, 1H), 2.09 (s, 3H), 3.38 (d, J=14.27 Hz, 1H), 3.98 (d, J=14.27 Hz, 1H), 6.86-6.93 (m, 1H), 6.95 (s, 1H), 6.97-7.03 (m, 1H), 7.07 (t, J=8.60 Hz, 1H), 7.20-7.29 (m, 2H), 7.33-7.48 (m, 1H), 10.88 (s, 1H).

Example 6 (2)

2-acetyl-1-(3,5-difluorophenyl)-1,2,3,9-tetrahydrospiro[β-carboline-4,1'-cyclopropane]

TLC: Rf 0.35 (hexane:ethyl acetate=2:1);
$^1$H NMR (DMSO-$d_6$): δ 0.74-0.89 (m, 1H), 1.06-1.17 (m, 2H), 1.53-1.67 (m, 1H), 2.14 (s, 3 H), 3.29-3.39 (m, 1H), 3.57 (d, J=14.64 Hz, 1H), 6.84 (s, 1H), 6.86-6.99 (m, 3H), 7.02-7.10 (m, 1H), 7.16-7.29 (m, 2H), 7.33 (d, J=8.05 Hz, 1H), 11.10 (s, 1H).

Example 6 (3)

2-acetyl-1-(2,4-difluorophenyl)-1,2,3,9-tetrahydrospiro[β-carboline-4,1'-cyclopropane]

TLC: Rf 0.27 (hexane:ethyl acetate=2:1);
$^1$H NMR (DMSO-$d_6$): δ 0.75-0.88 (m, 1H), 1.03-1.21 (m, 2H), 1.49-1.69 (m, 1H), 2.09 (s, 3 H), 3.25-3.37 (m, 1H), 3.60 (d, J=14.45 Hz, 1H), 6.86-7.09 (m, 4H), 7.11 (s, 1H), 7.19-7.46 (m, 3H), 10.96 (s, 1H).

Example 6 (4)

2-acetyl-1-(2,3-difluorophenyl)-1,2,3,9-tetrahydrospiro[β-carboline-4,1'-cyclopropane]

TLC: Rf 0.24 (hexane:ethyl acetate=2:1);
$^1$H NMR (DMSO-$d_6$): δ 0.72-0.92 (m, 1H), 1.02-1.21 (m, 2H), 1.53-1.70 (m, 1H), 2.10 (s, 3 H), 3.25-3.39 (m, 1H), 3.65 (d, J=14.82 Hz, 1H), 6.74-6.84 (m, 1H), 6.88-6.97 (m, 1H), 7.00-7.09 (m, 1H), 7.09-7.20 (m, 2H), 7.22-7.31 (m, 2H), 7.34-7.47 (m, 1H), 10.97 (s, 1H).

Example 6 (5)

2-acetyl-1-(2,5-difluorophenyl)-1,2,3,9-tetrahydrospiro[β-carboline-4,1'-cyclopropane]

TLC: Rf 0.47 (hexane:ethyl acetate=1:1);
$^1$H NMR (DMSO-$d_6$): δ 0.76-0.95 (m, 1H), 0.98-1.20 (m, 2H), 1.55-1.68 (m, 1H), 2.10 (s, 3 H), 3.24-3.41 (m, 1H), 3.66 (d, J=14.64 Hz, 1H), 6.62-6.74 (m, 1H), 6.88-6.98 (m, 1H), 6.99-7.08 (m, 1H), 7.09 (s, 1H), 7.17-7.48 (m, 4H), 10.96 (s, 1H).

Example 6 (6)

2-acetyl-1-(3,4-difluorophenyl)-1,2,3,9-tetrahydrospiro[β-carboline-4,1'-cyclopropane]

TLC: Rf 0.75 (hexane:ethyl acetate=1:2);
$^1$H NMR (DMSO-d$_6$): δ 0.75-0.88 (m, 1H), 1.04-1.18 (m, 2H), 1.54-1.67 (m, 1H), 2.12 (s, 3 H), 3.24-3.40 (m, 1H), 3.55 (d, J=14.45 Hz, 1H), 6.84 (s, 1H), 6.88-6.98 (m, 1H), 6.99-7.11 (m, 2H), 7.14-7.28 (m, 2H), 7.30 (d, J=7.87 Hz, 1H), 7.35-7.52 (m, 1H), 11.07 (s, 1H).

Example 6 (7)

2-acetyl-6-chloro-1-(3-fluorophenyl)-1,2,3,9-tetrahydrospiro[β-carboline-4,1'-cyclopropane]

TLC: Rf 0.50 (hexane:ethyl acetate=1:1);
$^1$H NMR (DMSO-d$_6$): δ 0.75-0.90 (m, 1H), 1.04-1.19 (m, 2H), 1.51-1.62 (m, 1H), 2.12 (s, 3H), 3.23-3.41 (m, 1H), 3.54 (d, J=14.45 Hz, 1H), 6.88 (s, 1H), 6.93-7.01 (m, 1H), 7.01-7.10 (m, 2H), 7.10-7.21 (m, 1H), 7.22 (d, J=1.83 Hz, 1H), 7.33 (d, J=8.60 Hz, 1H), 7.35-7.47 (m, 1H), 11.33 (s, 1H).

Example 6 (8)

2-acetyl-1-(3-fluorophenyl)-6-methoxy-1,2,3,9-tetrahydrospiro[β-carboline-4,1'-cyclopropane]

TLC: Rf 0.26 (hexane:ethyl acetate=2:1);
$^1$H NMR (DMSO-d$_6$): δ 0.71-0.86 (m, 1H), 1.00-1.22 (m, 2H), 1.53-1.70 (m, 1H), 2.12 (s, 3H), 3.22-3.35 (m, 1H), 3.53 (d, J=13.91 Hz, 1H), 3.66-3.76 (m, 3H), 6.67 (d, J=2.20 Hz, 1 H), 6.71 (dd, J=8.60, 2.20 Hz, 1H), 6.86 (s, 1H), 6.93-7.01 (m, 1H), 7.05 (d, J=7.87 Hz, 1H), 7.10-7.24 (m, 2H), 7.34-7.47 (m, 1H), 10.92 (s, 1H).

Example 6 (9)

1-(3-fluorophenyl)-2-isobutyryl-1,2,3,9-tetrahydrospiro[β-carboline-4,1'-cyclopropane]

TLC: Rf 0.66 (hexane:ethyl acetate=2:1);
$^1$H NMR (DMSO-d$_6$): δ 0.76-0.90 (m, 1H), 0.94-1.19 (m, 8H), 1.52-1.63 (m, 1H), 2.92-3.05 (m, 1H), 3.42 (d, J=14.82 Hz, 1H), 3.52 (d, J=14.82 Hz, 1H), 6.88-6.99 (m, 3H), 6.99-7.10 (m, 2H), 7.10-7.20 (m, 1H), 7.24 (d, J=7.87 Hz, 1H), 7.31 (d, J=8.05 Hz, 1H), 7.35-7.49 (m, 1H), 11.10 (s, 1H).

Example 6 (10)

2-(cyclopropylcarbonyl)-1-(3-fluorophenyl)-1,2,3,9-tetrahydrospiro[β-carboline-4,1'-cyclopropane]

TLC: Rf 0.44 (hexane:ethyl acetate=2:1);
$^1$H NMR (DMSO-d$_6$): δ 0.68-0.90 (m, 5H), 1.02-1.19 (m, 2H), 1.56-1.67 (m, 1H), 2.04-2.17 (m, 1H), 3.57 (d, J=14.63 Hz, 1H), 3.69 (d, J=14.63 Hz, 1H), 6.87-6.99 (m, 3H), 7.00-7.09 (m, 2H), 7.11-7.21 (m, 1H), 7.25 (d, J=8.05 Hz, 1H), 7.31 (d, J=8.05 Hz, 1H), 7.36-7.46 (m, 1H), 11.09 (s, 1H).

Example 6 (11)

2-benzoyl-1-(3-fluorophenyl)-1,2,3,9-tetrahydrospiro[β-carboline-4,1'-cyclopropane]

TLC: Rf 0.42 (hexane:ethyl acetate=2:1);
$^1$H NMR (DMSO-d$_6$): δ 0.41-0.59 (m, 1H), 0.57-0.75 (m, 1H), 1.03-1.30 (m, 1H), 1.40-1.64 (m, 1H), 2.89 (d, J=13.72 Hz, 1H), 3.60 (d, J=13.72 Hz, 1H), 6.94 (t, J=7.50 Hz, 1H), 6.99-7.29 (m, 6H), 7.29-7.56 (m, 7H), 11.18 (s, 1H).

Example 6 (12)

1-(3-fluorophenyl)-N,N-dimethyl-1,9-dihydrospiro[β-carboline-4,1'-cyclopropane]-2(3H)-carboxamide TLC: Rf 0.17 (hexane:ethyl acetate=2:1);
$^1$H NMR (CDCl$_3$): δ 0.74-0.92 (m, 2H), 1.38-1.48 (m, 1H), 1.56-1.67 (m, 1H), 2.87 (s, 6H), 3.07 (d, J=13.72 Hz, 1H), 3.44 (d, J=13.72 Hz, 1H), 6.18 (s, 1H), 6.90-7.06 (m, 3H), 7.07-7.16 (m, 2H), 7.21-7.35 (m, 3H), 7.86 (s, 1H).

Example 6 (13)

methyl 1-(3-fluorophenyl)-1,9-dihydrospiro[β-carboline-4,1'-cyclopropane]-2(3H)-carboxylate TLC: Rf 0.53 (hexane:ethyl acetate=2:1);
$^1$H NMR (DMSO-d$_6$): δ 0.72-1.00 (m, 2H), 1.00-1.14 (m, 1H), 1.49-1.69 (m, 1H), 3.37 (s, 2 H), 3.68 (s, 3H), 6.44 (s, 1H), 6.88-6.97 (m, 1H), 6.97-7.13 (m, 3H), 7.14-7.22 (m, 1H), 7.26 (d, J=8.05 Hz, 1H), 7.31 (d, J=7.87 Hz, 1H), 7.37-7.50 (m, 1H), 11.04 (s, 1H).

Example 6 (14)

2-acetyl-1-(2,3-dihydro-1H-inden-5-yl)-1,2,3,9-tetrahydrospiro[β-carboline-4,1'-cyclopropane]

TLC: Rf 0.70 (hexane:ethyl acetate=1:2);
$^1$H NMR (DMSO-d$_6$): δ 0.73-0.89 (m, 1H), 1.01-1.16 (m, 2H), 1.52-1.66 (m, 1H), 1.90-2.04 (m, 2H), 2.09 (s, 3H), 2.69-2.91 (m, 4H), 3.22 (d, J=14.45 Hz, 1H), 3.59 (d, J=14.45 Hz, 1H), 6.87 (s, 1H), 6.88-6.95 (m, 1H), 6.95-7.09 (m, 3H), 7.18 (d, J=7.68 Hz, 1H), 7.23 (d, J=7.87 Hz, 1H), 7.27 (d, J=8.05 Hz, 1H), 11.01 (s, 1H).

Example 6 (15)

2-acetyl-6-fluoro-1-(3-fluorophenyl)-1,2,3,9-tetrahydrospiro[β-carboline-4,1'-cyclopropane]

TLC: Rf 0.55 (hexane:ethyl acetate=1:1);
$^1$H NMR (DMSO-d$_6$): δ 0.74-0.90 (m, 1H), 1.03-1.28 (m, 2H), 1.52-1.63 (m, 1H), 2.12 (s, 3 H), 3.22-3.34 (m, 1H), 3.54 (d, J=14.27 Hz, 1H), 6.83-6.94 (m, 2H), 6.94-7.08 (m, 3H), 7.09-7.20 (m, 1H), 7.29 (dd, J=8.78, 4.57 Hz, 1H), 7.34-7.46 (m, 1H), 11.20 (s, 1H).

Example 6 (16)

2-acetyl-1-(2,4-difluorophenyl)-6-fluoro-1,2,3,9-tetrahydrospiro[β-carboline-4,1'-cyclopropane]

TLC: Rf 0.53 (hexane:ethyl acetate=1:1);
$^1$H NMR (DMSO-d$_6$): δ 0.71-0.89 (m, 1H), 1.02-1.25 (m, 2H), 1.50-1.65 (m, 1H), 2.09 (s, 3 H), 3.20-3.35 (m, 1H), 3.60 (d, J=15.00 Hz, 1H), 6.79-7.07 (m, 4H), 7.10 (s, 1H), 7.20-7.34 (m, 2H), 11.07 (s, 1H).

Example 6 (17)

2-acetyl-1-(3,4-difluorophenyl)-6-fluoro-1,2,3,9-tetrahydrospiro[β-carboline-4,1'-cyclopropane]

TLC: Rf 0.58 (hexane:ethyl acetate=1:1);
$^1$H NMR (DMSO-d$_6$): δ 0.73-0.92 (m, 1H), 1.01-1.30 (m, 2H), 1.49-1.66 (m, 1H), 2.11 (s, 3 H), 3.24-3.32 (m, 1H), 3.54 (d, J=14.64 Hz, 1H), 6.84 (s, 1H), 6.85-6.95 (m, 1H), 6.95-7.09 (m, 2H), 7.13-7.24 (m, 1H), 7.29 (dd, J=8.87, 4.67 Hz, 1H), 7.34-7.49 (m, 1H), 11.18 (s, 1H).

Example 6 (18)

2-acetyl-1-(3-fluorophenyl)-7-methoxy-1,2,3,9-tetrahydrospiro[β-carboline-4,1'-cyclopropane]

TLC: Rf 0.44 (hexane:ethyl acetate=1:1);
$^1$H NMR (DMSO-d$_6$): δ 0.72-0.91 (m, 1H), 0.98-1.32 (m, 2H), 1.45-1.59 (m, 1H), 2.11 (s, 3 H), 3.20-3.36 (m, 1H), 3.52 (d, J=14.64 Hz, 1H), 3.73 (s, 3H), 6.57 (dd, J=8.78, 2.20 Hz, 1H), 6.80 (d, J=2.20 Hz, 1H), 6.83 (s, 1H), 6.97 (d, J=10.06 Hz, 1H), 7.01-7.24 (m, 3H), 7.33-7.46 (m, 1H), 10.88 (s, 1H).

Example 6 (19)

2-acetyl-7-fluoro-1-(3-fluorophenyl)-1,2,3,9-tetrahydrospiro[β-carboline-4,1'-cyclopropane]

TLC: Rf 0.52 (hexane:ethyl acetate=1:1);
$^1$H NMR (DMSO-d$_6$): δ 0.74-0.90 (m, 1H), 1.00-1.20 (m, 2H), 1.51-1.63 (m, 1H), 2.11 (s, 3 H), 3.19-3.39 (m, 1H), 3.54 (d, J=15.55 Hz, 1H), 6.73-6.84 (m, 1H), 6.86 (s, 1H), 6.94-7.02 (m, 1H), 7.02-7.20 (m, 3H), 7.23 (dd, J=8.97, 5.31 Hz, 1H), 7.32-7.48 (m, 1H), 11.20 (s, 1H).

Example 6 (20)

2-acetyl-1-(3-fluorophenyl)-5-methoxy-1,2,3,9-tetrahydrospiro[β-carboline-4,1'-cyclopropane]

TLC: Rf 0.63 (hexane:ethyl acetate=1:1);
$^1$H NMR (DMSO-d$_6$): δ 0.56-0.70 (m, 1H), 0.85-1.07 (m, 2H), 1.61-1.75 (m, 1H), 2.11 (s, 3 H), 3.19 (d, J=14.64 Hz, 1H), 3.53 (d, J=14.64 Hz, 1H), 3.80 (s, 3H), 6.48 (d, J=7.50 Hz, 1H), 6.83 (s, 1H), 6.90 (dd, J=8.05, 0.73 Hz, 1H), 6.93-7.03 (m, 2H), 7.05 (d, J=7.68 Hz, 1H), 7.09-7.22 (m, 1H), 7.34-7.46 (m, 1H), 11.15 (s, 1H).

Example 6 (21)

2-acetyl-1-(3-fluorophenyl)-1,2,3,9-tetrahydrospiro[β-carboline-4,1'-cyclopropane]

TLC: Rf 0.50 (hexane:ethyl acetate=1:1);
$^1$H NMR (DMSO-d$_6$): δ 0.74-0.87 (m, 1H), 1.07-1.18 (m, 2H), 1.52-1.68 (m, 1H), 2.12 (s, 3 H), 3.29 (d, J=14.65 Hz, 1H), 3.55 (d, J=14.65 Hz, 1H), 6.89 (s, 1H), 6.90-6.96 (m, 1H), 6.99 (dd, J=10.34, 1.92 Hz, 1H), 7.02-7.10 (m, 2H), 7.10-7.20 (m, 1H), 7.25 (d, J=8.06 Hz, 1H), 7.31 (d, J=8.06 Hz, 1H), 7.35-7.47 (m, 1H), 11.09 (s, 1H).

Example 7 (1) to Example 7 (21)

Using 1H-indole-3-ylacetonitrile or alternatively a corresponding nitrile derivative thereof and a corresponding aldehyde derivative in place of 1,3-benzodioxol-5-carboaldehyde, the operation having the same purpose as that in Example 1→Example 2→Example 3→Example 5 was conducted to obtain the following compound.

Example 7 (1)

1-(2,6-difluorophenyl)-N-(3,5-dimethylphenyl)-1,9-dihydrospiro[β-carboline-4,1'-cyclopropane]-2(3H)-carboxamide TLC: Rf 0.39 (hexane:ethyl acetate=2:1);
$^1$H NMR (DMSO-d$_6$): δ 0.72-0.86 (m, 1H), 0.91-1.12 (m, 2H), 1.56-1.68 (m, 1H), 2.18 (s, 6 H), 3.63 (d, J=14.64 Hz, 1H), 3.77 (d, J=14.64 Hz, 1H), 6.58 (s, 1H), 6.85-6.93 (m, 1H), 6.96-7.15 (m, 6H), 7.19-7.28 (m, 2H), 7.34-7.51 (m, 1H), 8.56 (s, 1H), 10.93 (s, 1H).

Example 7 (2)

1-(3,5-difluorophenyl)-N-(3,5-dimethylphenyl)-1,9-dihydrospiro[β-carboline-4,1'-cyclopropane]-2(3H)-carboxamide TLC: Rf 0.60 (hexane:ethyl acetate=2:1);
$^1$H NMR (DMSO-d$_6$): δ 0.68-0.83 (m, 1H), 0.98-1.23 (m, 2H), 1.50-1.65 (m, 1H), 2.20 (s, 6 H), 3.44 (d, J=14.82 Hz, 1H), 3.67 (d, J=14.82 Hz, 1H), 6.61 (s, 1H), 6.73 (s, 1H), 6.85-6.99 (m, 3H), 7.00-7.15 (m, 3H), 7.15-7.29 (m, 2H), 7.33 (d, J=7.87 Hz, 1H), 8.52 (s, 1H), 11.13 (s, 1H).

Example 7 (3)

1-(2,4-difluorophenyl)-N-(3,5-dimethylphenyl)-1,9-dihydrospiro[β-carboline-4,1'-cyclopropane]-2(3H)-carboxamide TLC: Rf 0.53 (hexane:ethyl acetate=2:1);
$^1$H NMR (DMSO-d$_6$): δ 0.63-0.84 (m, 1H), 0.91-1.15 (m, 2H), 1.45-1.68 (m, 1H), 2.19 (s, 6 H), 3.44 (d, J=15.00 Hz, 1H), 3.57 (d, J=15.00 Hz, 1H), 6.58 (s, 1H), 6.84-6.97 (m, 2H), 6.97-7.12 (m, 5H), 7.23 (d, J=7.87 Hz, 1H), 7.26-7.37 (m, 2H), 8.57 (s, 1H), 11.00 (s, 1H).

Example 7 (4)

1-(2,3-difluorophenyl)-N-(3,5-dimethylphenyl)-1,9-dihydrospiro[β-carboline-4,1'-cyclopropane]-2(3H)-carboxamide TLC: Rf 0.59 (hexane:ethyl acetate=2:1);
$^1$H NMR (DMSO-d$_6$): δ 0.68-0.83 (m, 1H), 0.94-1.17 (m, 2H), 1.49-1.66 (m, 1H), 2.19 (s, 6 H), 3.48 (d, J=15.01 Hz, 1H), 3.59 (d, J=15.01 Hz, 1H), 6.59 (s, 1H), 6.74 (t, J=6.86 Hz, 1H), 6.86-6.97 (m, 1H), 6.98-7.20 (m, 5H), 7.24 (d, J=7.87 Hz, 1H), 7.29 (d, J=8.05 Hz, 1H), 7.34-7.50 (m, 1H), 8.59 (s, 1H), 11.00 (s, 1H).

Example 7 (5)

1-(2,5-difluorophenyl)-N-(3,5-dimethylphenyl)-1,9-dihydrospiro[β-carboline-4,1'-cyclopropane]-2(3H)-carboxamide TLC: Rf 0.50 (hexane:ethyl acetate=3:1);
$^1$H NMR (DMSO-d$_6$): δ 0.70-0.84 (m, 1H), 0.95-1.17 (m, 2H), 1.53-1.66 (m, 1H), 2.19 (s, 6 H), 3.49 (d, J=15.01 Hz, 1H), 3.59 (d, J=15.01 Hz, 1H), 6.53-6.64 (m, 2H), 6.88-6.98 (m, 1 H), 7.00 (s, 1H), 7.02-7.14 (m, 3H), 7.18-7.40 (m, 4H), 8.59 (s, 1H), 11.01 (s, 1H).

Example 7 (6)

1-(3,4-difluorophenyl)-N-(3,5-dimethylphenyl)-1,9-dihydrospiro[β-carboline-4,1'-cyclopropane]-2(3H)-carboxamide TLC: Rf 0.47 (hexane:ethyl acetate=3:1);
$^1$H NMR (DMSO-d$_6$): δ 0.69-0.83 (m, 1H), 1.00-1.21 (m, 2H), 1.53-1.65 (m, 1H), 2.20 (s, 6H), 3.41 (d, J=14.82 Hz, 1H), 3.63 (d, J=14.82 Hz, 1H), 6.61 (s, 1H), 6.73 (s, 1H), 6.88-6.97 (m, 1H), 7.00-7.14 (m, 4H), 7.17-7.28 (m, 2H), 7.31 (d, J=8.05 Hz, 1H), 7.36-7.49 (m, 1H), 8.48 (s, 1H), 11.10 (s, 1H).

Example 7 (7)

6-chloro-N-(3,5-dimethylphenyl)-1-(3-fluorophenyl)-1,9-dihydrospiro[β-carboline-4,1'-cyclopropane]-2(3H)-carboxamide TLC: Rf 0.40 (hexane:ethyl acetate=3:1);
$^1$H NMR (DMSO-d$_6$): δ 0.69-0.88 (m, 1H), 0.99-1.29 (m, 2H), 1.49-1.63 (m, 1H), 2.20 (s, 6H), 3.41 (d, J=14.45 Hz, 1H), 3.64 (d, J=14.45 Hz, 1H), 6.61 (s, 1H), 6.77 (s, 1H), 6.96-7.03 (m, 1H), 7.03-7.12 (m, 4H), 7.12-7.21 (m, 1H), 7.22 (d, J=1.83 Hz, 1H), 7.34 (d, J=8.60 Hz, 1H), 7.37-7.49 (m, 1H), 8.50 (s, 1H), 11.37 (s, 1H).

Example 7 (8)

N-(3,5-dimethylphenyl)-1-(3-fluorophenyl)-6-methoxy-1,9-dihydrospiro[β-carboline-4,1'-cyclopropane]-2(3H)-carboxamide TLC: Rf 0.24 (hexane:ethyl acetate=3:1);
$^1$H NMR (DMSO-d$_6$): δ 0.67-0.78 (m, 1H), 1.05-1.17 (m, 2H), 1.53-1.67 (m, 1H), 2.21 (s, 6H), 3.40 (d, J=14.64 Hz, 1H), 3.62 (d, J=14.64 Hz, 1H), 3.72 (s, 3H), 6.61 (s, 1H), 6.67 (d, J=2.20 Hz, 1H), 6.69-6.77 (m, 2H), 6.96-7.04 (m, 1H), 7.06-7.19 (m, 4H), 7.21 (d, J=8.78 Hz, 1H), 7.35-7.49 (m, 1H), 8.48 (s, 1H), 10.95 (s, 1H).

Example 7 (9)

1-(2,3-dihydro-1H-inden-5-yl)-N-(3,5-dimethylphenyl)-1,9-dihydrospiro[β-carboline-4,1'-cyclopropane]-2(3H)-carboxamide TLC: Rf 0.48 (hexane:ethyl acetate=3:1);
$^1$H NMR (DMSO-d$_6$): δ 0.68-0.79 (m, 1H), 1.00-1.16 (m, 2H), 1.52-1.65 (m, 1H), 1.91-2.05 (m, 2H), 2.20 (s, 6H), 2.75-2.86 (m, 4H), 3.45 (d, J=14.45 Hz, 1H), 3.58 (d, J=14.45 Hz, 1 H), 6.59 (s, 1H), 6.74 (s, 1H), 6.87-6.95 (m, 1H), 6.97-7.06 (m, 2H), 7.08 (s, 1H), 7.10 (s, 2H), 7.16-7.31 (m, 3H), 8.41 (s, 1H), 11.02 (s, 1H).

Example 7 (10)

2-acetyl-1-(3-fluorophenyl)-6,7-dimethoxy-1,2,3,9-tetrahydrospiro[β-carboline-4,1'-cyclopropane]

TLC: Rf 0.21 (hexane:ethyl acetate=1:1);
$^1$H NMR (DMSO-d$_6$): δ 0.65-0.87 (m, 1H), 0.96-1.20 (m, 2H), 1.50-1.68 (m, 1H), 2.11 (s, 3H), 3.18-3.29 (m, 1H), 3.50 (d, J=14.27 Hz, 1H), 3.71 (s, 3H), 3.73 (s, 3H), 6.66 (s, 1H), 6.79-6.90 (m, 2H), 6.91-6.99 (m, 1H), 7.00-7.09 (m, 1H), 7.08-7.22 (m, 1H), 7.31-7.48 (m, 1 H), 10.76 (s, 1H).

Example 7 (11)

2-acetyl-1-(2,4-difluorophenyl)-6,7-dimethoxy-1,2,3,9-tetrahydrospiro[β-carboline-4,1'-cyclopropane]

TLC: Rf 0.21 (hexane:ethyl acetate=1:1);
$^1$H NMR (DMSO-d$_6$): δ 0.65-0.93 (m, 1H), 0.98-1.27 (m, 2H), 1.50-1.64 (m, 1H), 2.08 (s, 3H), 3.25 (d, J=14.45 Hz, 1H), 3.55 (d, J=14.45 Hz, 1H), 3.71 (s, 3H), 3.72 (s, 3H), 6.66 (s, 1 H), 6.75-7.10 (m, 4H), 7.18-7.31 (m, 1H), 10.62 (s, 1H).

Example 7 (12)

2-acetyl-1-(2,4-difluorophenyl)-7-fluoro-1,2,3,9-tetrahydrospiro[β-carboline-4,1'-cyclopropane]

TLC: Rf 0.56 (hexane:ethyl acetate=1:1);
$^1$H NMR (DMSO-d$_6$): δ 0.75-0.89 (m, 1H), 1.13 (m, 2H), 1.51-1.63 (m, 1H), 2.08 (s, 3H), 3.19-3.37 (m, 1H), 3.59 (d, J=14.82 Hz, 1H), 6.71-6.83 (m, 1H), 6.89-7.15 (m, 4H), 7.17-7.35 (m, 2H), 11.06 (s, 1H).

Example 7 (13)

2-acetyl-1-(3,4-difluorophenyl)-7-fluoro-1,2,3,9-tetrahydrospiro[β-carboline-4,1'-cyclopropane]

TLC: Rf 0.56 (hexane:ethyl acetate=1:1);
$^1$H NMR (DMSO-d$_6$): δ 0.75-0.90 (m, 1H), 1.00-1.20 (m, 2H), 1.50-1.65 (m, 1H), 2.11 (s, 3H), 3.22-3.38 (m, 1H), 3.54 (d, J=14.27 Hz, 1H), 6.72-6.87 (m, 2H), 6.98-7.06 (m, 1H), 7.09 (dd, J=10.06, 2.38 Hz, 1H), 7.15-7.29 (m, 2H), 7.34-7.49 (m, 1H), 11.17 (s, 1H).

Example 7 (14)

2-acetyl-5-fluoro-1-(3-fluorophenyl)-1,2,3,9-tetrahydrospiro[β-carboline-4,1'-cyclopropane]

TLC: Rf 0.58 (hexane:ethyl acetate=1:1);
$^1$H NMR (DMSO-d$_6$): δ 0.71-0.84 (m, 1H), 0.84-0.96 (m, 1H), 1.07-1.19 (m, 1H), 1.34-1.46 (m, 1H), 2.12 (s, 3H), 3.25-3.36 (m, 1H), 3.56 (dd, J=14.73, 1.19 Hz, 1H), 6.67-6.80 (m, 1 H), 6.88 (s, 1H), 6.95-7.10 (m, 3H), 7.11-7.23 (m, 2H), 7.35-7.49 (m, 1H), 11.50 (s, 1H).

Example 7 (15)

2-acetyl-1-(2,4-difluorophenyl)-5-fluoro-1,2,3,9-tetrahydrospiro[β-carboline-4,1'-cyclopropane]

TLC: Rf 0.58 (hexane:ethyl acetate=1:1);
$^1$H NMR (DMSO-d$_6$): δ 0.72-0.85 (m, 1H), 0.86-0.98 (m, 1H), 1.05-1.17 (m, 1H), 1.32-1.45 (m, 1H), 2.09 (s, 3H), 3.24-3.38 (m, 1H), 3.62 (d, J=15.00 Hz, 1H), 6.67-6.79 (m, 1H), 6.91-7.09 (m, 3H), 7.09-7.19 (m, 2H), 7.24-7.36 (m, 1H), 11.38 (s, 1H).

Example 7 (16)

2-acetyl-1-(3,4-difluorophenyl)-5-fluoro-1,2,3,9-tetrahydrospiro[β-carboline-4,1'-cyclopropane]

TLC: Rf 0.58 (hexane:ethyl acetate=1:1);
$^1$H NMR (DMSO-d$_6$): δ 0.71-0.84 (m, 1H), 0.84-0.97 (m, 1H), 1.06-1.19 (m, 1H), 1.34-1.48 (m, 1H), 2.12 (s, 3H), 3.22-3.36 (m, 1H), 3.56 (d, J=14.64 Hz, 1H), 6.67-6.80 (m, 1H), 6.85 (s, 1H), 7.00-7.11 (m, 2H), 7.16 (d, J=8.05 Hz, 1H), 7.18-7.28 (m, 1H), 7.36-7.51 (m, 1H), 11.47 (s, 1H).

Example 7 (17)

2-acetyl-1-(3-fluorophenyl)-8-methoxy-1,2,3,9-tetrahydrospiro[β-carboline-4,1'-cyclopropane]

TLC: Rf 0.48 (hexane:ethyl acetate=1:1);
$^1$H NMR (DMSO-d$_6$): δ 0.70-0.85 (m, 1H), 1.00-1.16 (m, 2H), 1.47-1.61 (m, 1H), 2.12 (s, 3H), 3.20-3.36 (m, 1H), 3.50 (d, J=14.46 Hz, 1H), 3.86 (s, 3H), 6.63 (dd, J=6.68, 1.74 Hz, 1H), 6.76-6.90 (m, 3H), 6.93 (d, J=10.06 Hz, 1H), 7.00 (d, J=7.68 Hz, 1H), 7.07-7.19 (m, 1H), 7.31-7.43 (m, 1H), 11.14 (s, 1H).

Example 7 (18)

2-acetyl-1-(2,4-difluorophenyl)-8-methoxy-1,2,3,9-tetrahydrospiro[β-carboline-4,1'-cyclopropane]

TLC: Rf 0.45 (hexane:ethyl acetate=1:1);
$^1$H NMR (DMSO-d$_6$): δ 0.72-0.86 (m, 1H), 1.00-1.19 (m, 2H), 1.48-1.62 (m, 1H), 2.08 (s, 3H), 3.17-3.37 (m, 1H), 3.53 (d, J=14.82 Hz, 1H), 3.84 (s, 3H), 6.62 (dd, J=6.95, 1.46 Hz, 1H), 6.76-6.92 (m, 3H), 6.93-7.04 (m, 1H), 7.14 (s, 1H), 7.18-7.30 (m, 1H), 11.02 (s, 1H).

Example 7 (19)

2-acetyl-1-(3,4-difluorophenyl)-8-methoxy-1,2,3,9-tetrahydrospiro[β-carboline-4,1'-cyclopropane]

TLC: Rf 0.45 (hexane:ethyl acetate=1:1);
$^1$H NMR (DMSO-d$_6$): δ 0.72-0.85 (m, 1H), 1.00-1.15 (m, 2H), 1.48-1.63 (m, 1H), 2.11 (s, 3H), 3.18-3.36 (m, 1H), 3.50 (d, J=14.27 Hz, 1H), 3.86 (s, 3H), 6.63 (dd, J=6.77, 1.83 Hz, 1H), 6.78-6.91 (m, 3H), 6.93-7.03 (m, 1H), 7.08-7.20 (m, 1H), 7.31-7.46 (m, 1H), 11.12 (s, 1H).

Example 7 (20)

2-acetyl-1-(3-fluorophenyl)-6,8-dimethoxy-1,2,3,9-tetrahydrospiro[β-carboline-4,1'-cyclopropane]

TLC: Rf 0.68 (hexane:ethyl acetate=1:1);
$^1$H NMR (DMSO-d$_6$): δ 0.68-0.81 (m, 1H), 1.01-1.19 (m, 2H), 1.51-1.64 (m, 1H), 2.11 (s, 3H), 3.17-3.37 (m, 1H), 3.43-3.54 (m, 1H), 3.71 (s, 3H), 3.84 (s, 3H), 6.25 (d, J=1.83 Hz, 1H), 6.31 (d, J=1.83 Hz, 1H), 6.84 (s, 1H), 6.92 (d, J=10.06 Hz, 1H), 7.00 (d, J=7.87 Hz, 1H), 7.07-7.18 (m, 1H), 7.31-7.44 (m, 1H), 10.97 (s, 1H).

Example 7 (21)

2-acetyl-1-(3,4-difluorophenyl)-6,8-dimethoxy-1,2,3,9-tetrahydrospiro[β-carboline-4,1'-cyclopropane]

TLC: Rf 0.61 (hexane:ethyl acetate=1:1);
$^1$H NMR (DMSO-d$_6$): δ 0.68-0.82 (m, 1H), 0.99-1.17 (m, 2H), 1.50-1.64 (m, 1H), 2.11 (s, 3 H), 3.25 (d, J=15.00 Hz, 1H), 3.48 (d, J=15.00 Hz, 1H), 3.71 (s, 3H), 3.84 (s, 3H), 6.25 (d, J=2.01 Hz, 1H), 6.32 (d, J=2.01 Hz, 1H), 6.81 (s, 1H), 6.94-7.03 (m, 1H), 7.08-7.20 (m, 1H), 7.33-7.46 (m, 1H), 10.97 (s, 1H).

Example 8

3-methoxy-N-[2-(1H-pyrrolo[2,3-b]pyridin-3-yl)ethyl]benzamide

To a mixed solution of [2-(1H-pyrrolo[2,3-b]pyridin-3-yl)ethyl]amine (580 mg) and 3-methoxybenzoic acid (658 mg) in tetrahydrofuran (5 mL) and N,N-dimethylformamide (3 mL), 1-hydroxy-7-azabenzotriazole (HOAt) (588 mg) and 1-ethyl-3-(3-dimethylaminopropyl)carbodiimide (EDC) hydrochloride (826 mg) were added, followed by stirring at room temperature until materials disappear. To the reaction mixture, ice water and an aqueous saturated sodium hydrogen carbonate solution were sequentially added and then extracted with ethyl acetate. The organic layer was washed with saturated saline, dried over anhydrous sodium sulfate and then concentrated. The residue was purified by silica gel column chromatography (ethyl acetate:hexane=2:8) to obtain the titled compound having the following physical properties (612 mg).

TLC: Rf 0.30 (hexane:ethyl acetate=1:4);
$^1$H NMR (CDCl$_3$): δ 3.09 (t, J=6.77 Hz, 2H), 3.71-3.87 (m, 5H), 6.20 (s, 1H), 6.98-7.04 (m, 1 H), 7.09 (dd, J=7.87, 4.76 Hz, 1H), 7.12-7.17 (m, 1H), 7.17-7.21 (m, 1H), 7.24-7.32 (m, 2 H), 7.97 (dd, J=7.87, 1.46 Hz, 1H), 8.32 (dd, J=4.76, 1.46 Hz, 1H), 8.98 (s, 1H).

Example 9

8-(3-methoxyphenyl)-6,9-dihydro-5H-pyrido[4',3':4,5]pyrrolo[2,3-b]pyridine

To an anhydrous acetonitrile (8.2 mL) suspension of the compound (605 mg) prepared in Example 8, N,N-diethylaniline (3 μL) was added, followed by stirring at 85° C. until materials are dissolved. Then phosphorus oxychloride (1.57 g) was added, followed by stirring at 75 to 85° C. overnight. The reaction mixture was air-cooled to room temperature, and then the solvent and excess phosphorus oxychloride were distilled off. To the residue, acetonitrile, ethyl acetate and an aqueous saturated sodium hydrogen carbonate solution were sequentially added, followed by separation. The aqueous layer was extracted with ethyl acetate. The combined organic layer was washed with saturated saline, dried over anhydrous sodium sulfate and then concentrated. The residue was purified by silica gel column chromatography (hexane:ethyl acetate=33:67) to obtain the titled compound having the following physical properties (260 mg).

TLC: Rf 0.24 (hexane:ethyl acetate=1:2);
$^1$H NMR (CDCl$_3$): δ 2.91-2.99 (m, 2H), 3.83 (s, 3H), 4.02-4.11 (m, 2H), 6.97-7.04 (m, 1H), 7.05-7.13 (m, 1H), 7.34-7.42 (m, 3H), 7.61-7.69 (m, 1H), 7.94 (dd, J=7.87, 1.10 Hz, 1H), 10.84 (s, 1H).

Example 10

8-(3-methoxyphenyl)-6,7,8,9-tetrahydro-5H-pyrido[4',3':4,5]pyrrolo[2,3-b]pyridine To a methanol (5 mL) suspension of the compound (250 mg) prepared in Example 9, sodium borohydride (102 mg) was added at room temperature, followed by stirring until materials disappear. The reaction mixture was concentrated. To the residue, ethyl acetate and an aqueous saturated sodium hydrogen carbonate solution were added, followed by separation. The organic layer was washed with saturated saline, dried over anhydrous sodium sulfate and then concentrated. The residue was by purified by silica gel column chromatography (hexane:ethyl acetate=1:4→ethyl acetate:methanol=8:2) to obtain the titled compound having the following physical properties (210 mg).

TLC: Rf 0.19 (dichloromethane:methanol=19:1);

$^1$H NMR (CDCl$_3$): δ 2.69-2.83 (m, 1H), 2.83-2.97 (m, 1H), 3.09-3.22 (m, 1H), 3.35-3.47 (m, 1H), 3.77 (s, 3H), 5.19 (s, 1H), 6.83-6.95 (m, 3H), 6.99 (dd, J=7.78, 4.76 Hz, 1H), 7.24-7.32 (m, 1H), 7.80 (dd, J=7.78, 1.28 Hz, 1H), 7.95 (dd, J=4.76, 1.28 Hz, 1H), 8.99 (s, 1H).

Example 11

N-(3,5-dimethylphenyl)-8-(3-methoxyphenyl)-5,6,8,9-tetrahydro-7H-pyrido[4',3':4,5]pyrrolo[2,3-b]pyridine-7-carboxamide

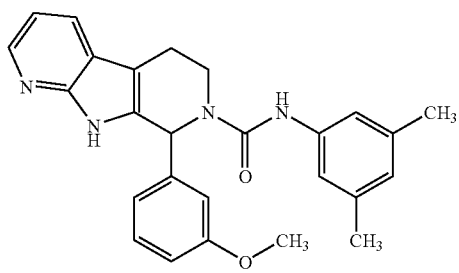

Under an argon atmosphere, to an anhydrous tetrahydrofuran (2 mL) solution of the compound (95 mg) prepared in Example 10, 1-isocyanato-3,5-dimethylbenzene (40 µL) was added, followed by stirring at room temperature until materials disappear. The reaction mixture was concentrated and the resulting residue was washed with tert-butyl methyl ether and then collected by filtration to obtain the titled compound having the following physical properties (126 mg).

TLC: Rf 0.25 (methylene chloride:methanol=19:1);

$^1$H NMR (DMSO-d$_6$): δ 2.20 (s, 6H), 2.66-2.98 (m, 2H), 3.03-3.23 (m, 1H), 3.69 (s, 3H), 4.26 (dd, J=14.18, 4.30 Hz, 1H), 6.60 (s, 1H), 6.65 (s, 1H), 6.76-6.83 (m, 2H), 6.84-6.91 (m, 1H), 7.04 (dd, J=7.87, 4.76 Hz, 1H), 7.11 (s, 2H), 7.26 (t, J=8.14 Hz, 1H), 7.88 (dd, J=7.78, 1.19 Hz, 1H), 8.16 (dd, J=4.76, 1.65 Hz, 1H), 8.59 (s, 1H), 11.52 (s, 1H).

Example 12

7-acetyl-8-(3-methoxyphenyl)-6,7,8,9-tetrahydro-5H-pyrido[4',3':4,5]pyrrolo[2,3-b]pyridine

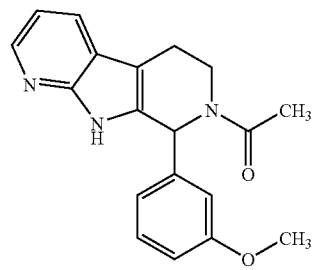

To a pyridine (3 mL) solution of the compound (105 mg) prepared in Example 10, acetic anhydride (39 µL) was added, followed by stirring at room temperature until materials disappear. The reaction mixture was concentrated. The resulting residue was dissolved in ethyl acetate, washed in turn with an aqueous saturated sodium hydrogen carbonate solution and saturated saline, dried over anhydrous sodium sulfate and then concentrated. The residue was washed with tert-butyl methyl ether and then collected by filtration to obtain the titled compound having the following physical properties (126 mg).

TLC: Rf 0.20 (methylene chloride:methanol=19:1);

$^1$H NMR (CDCl$_3$): δ 2.21 (s, 3H), 2.75-3.03 (m, 1H), 3.40-3.56 (m, 1H), 3.75 (s, 2H), 3.92 (dd, J=14.27, 4.39 Hz, 1H), 6.81-6.89 (m, 1H), 6.89-6.97 (m, 1H), 7.02 (dd, J=7.78, 4.85 Hz, 1H), 7.06 (s, 1H), 7.22 (t, J=7.87 Hz, 1H), 7.80 (dd, J=7.87, 1.46 Hz, 1H), 7.98 (dd, J=4.76, 1.46 Hz, 1H), 9.96 (s, 1H).

Example 13 (1) to Example 13 (10)

Using a corresponding carboxylic acid derivative in place of 3-methoxybenzoic acid and 1-isocyanato-3,5-dimethylbenzene or alternatively a corresponding isocyanate derivative, the operation having the same purpose as that in Example 8→Example 9→Example 10→Example 11 was conducted to obtain the following compound.

Example 13 (1)

N-(3,5-dimethylphenyl)-8-(2-fluorophenyl)-5,6,8,9-tetrahydro-7H-pyrido[4',3':4,5]pyrrolo[2,3-b]pyridine-7-carboxamide TLC: Rf 0.74 (ethyl acetate);

$^1$H NMR (DMSO-d$_6$): δ 2.19 (s, 6H), 2.67-2.94 (m, 2H), 3.05-3.24 (m, 1H), 4.25 (dd, J=14.45, 4.57 Hz, 1H), 6.59 (s, 1H), 6.78-6.90 (m, 1H), 6.98 (s, 1H), 7.01-7.17 (m, 4H), 7.18-7.31 (m, 1H), 7.32-7.44 (m, 1H), 7.88 (dd, J=7.78, 1.19 Hz, 1H), 8.16 (dd, J=4.76, 1.65 Hz, 1H), 8.65 (s, 1H), 11.42 (s, 1H).

Example 13 (2)

8-(3-fluorophenyl)-N-[2-(trifluoromethyl)phenyl]-5,6,8,9-tetrahydro-7H-pyrido[4',3':4,5]pyrrolo[2,3-b]pyridine-7-carboxamide TLC: Rf 0.55 (methylene chloride:methanol=19:1);
$^1$H NMR (DMSO-$d_6$): δ 2.73-3.00 (m, 2H), 3.07-3.23 (m, 1H), 4.24 (dd, J=14.18, 3.93 Hz, 1H), 6.62 (s, 1H), 6.98-7.11 (m, 3H), 7.11-7.22 (m, 1H), 7.33-7.51 (m, 3H), 7.58-7.77 (m, 2H), 7.92 (dd, J=7.78, 1.46 Hz, 1H), 8.18 (dd, J=4.76, 1.46 Hz, 1H), 8.57 (s, 1H), 11.55 (s, 1H).

Example 13 (3)

8-(3-fluorophenyl)-N-(3-methoxyphenyl)-5,6,8,9-tetrahydro-7H-pyrido[4',3':4,5]pyrrolo[2,3-b]pyridine-7-carboxamide TLC: Rf 0.22 (hexane:ethyl acetate=1:1);
$^1$H NMR (DMSO-$d_6$): δ 2.73-2.97 (m, 2H), 3.07-3.22 (m, 1H), 3.70 (s, 3H), 4.30 (dd, J=14.27, 4.94 Hz, 1H), 6.50-6.59 (m, 1H), 6.69 (s, 1H), 6.98-7.22 (m, 7H), 7.34-7.47 (m, 1H), 7.90 (dd, J=7.68, 1.65 Hz, 1H), 8.18 (dd, J=4.76, 1.65 Hz, 1H), 8.74 (s, 1H), 11.55 (s, 1H).

Example 13 (4)

N-(3-chlorophenyl)-8-(3-fluorophenyl)-5,6,8,9-tetrahydro-7H-pyrido[4',3':4,5]pyrrolo[2,3-b]pyridine-7-carboxamide TLC: Rf 0.51 (hexane:ethyl acetate=1:1);
$^1$H NMR (DMSO-$d_6$): δ 2.74-2.98 (m, 2H), 3.08-3.22 (m, 1H), 4.29 (dd, J=14.27, 4.03 Hz, 1H), 6.68 (s, 1H), 6.96-7.21 (m, 5H), 7.27 (t, J=8.05 Hz, 1H), 7.36-7.49 (m, 2H), 7.67 (t, J=2.01 Hz, 1H), 7.90 (dd, J=7.87, 1.46 Hz, 1H), 8.18 (dd, J=4.76, 1.46 Hz, 1H), 8.94 (s, 1H), 11.56 (s, 1H).

Example 13 (5)

8-(1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide TLC: Rf 0.70 (hexane:ethyl acetate=1:2);
$^1$H NMR (DMSO-$d_6$): δ 2.20 (s, 6H), 2.62-2.98 (m, 2H), 3.04-3.25 (m, 1H), 4.13-4.34 (m, 1H), 5.98 (d, J=0.73 Hz, 1H), 5.99 (d, J=0.73 Hz, 1H), 6.60 (s, 2H), 6.63 (dd, J=8.05, 1.65 Hz, 1H), 6.80 (d, J=1.65 Hz, 1H), 6.86 (d, J=8.05 Hz, 1H), 7.04 (dd, J=7.78, 4.76 Hz, 1H), 7.11 (s, 2H), 7.88 (dd, J=7.78, 1.65 Hz, 1H), 8.16 (dd, J=4.76, 1.65 Hz, 1H), 8.55 (s, 1H), 11.48 (s, 1H).

Example 13 (6)

8-(3,5-difluorophenyl)-N-(3,5-dimethylphenyl)-5,6,8,9-tetrahydro-7H-pyrido[4',3':4,5]pyrrolo[2,3-b]pyridine-7-carboxamide TLC: Rf 0.79 (hexane:ethyl acetate=1:2);
$^1$H NMR (DMSO-$d_6$): δ 2.21 (s, 6H), 2.68-2.95 (m, 2H), 3.09-3.24 (m, 1H), 4.24-4.35 (m, 1H), 6.61 (s, 1H), 6.63 (s, 1H), 6.87-7.00 (m, 2H), 7.06 (dd, J=7.78, 4.76 Hz, 1H), 7.11 (s, 2H), 7.16-7.28 (m, 1H), 7.91 (dd, J=7.78, 1.46 Hz, 1H), 8.19 (dd, J=4.76, 1.46 Hz, 1H), 8.65 (s, 1H), 11.57 (s, 1H).

Example 13 (7)

8-(2,2-difluoro-1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide TLC: Rf 0.50 (hexane:ethyl acetate=1:1);
$^1$H NMR (DMSO-$d_6$): δ 2.20 (s, 6H), 2.68-2.97 (m, 2H), 3.08-3.23 (m, 1H), 4.26 (dd, J=14.36, 4.67 Hz, 1H), 6.60 (s, 1H), 6.66 (s, 1H), 7.01-7.09 (m, 2H), 7.11 (s, 2H), 7.26 (d, J=1.46 Hz, 1H), 7.37 (d, J=8.23 Hz, 1H), 7.90 (dd, J=7.78, 1.55 Hz, 1H), 8.17 (dd, J=4.67, 1.55 Hz, 1H), 8.59 (s, 1H), 11.48 (s, 1H).

Example 13 (8)

N-(adamantane-1-yl)-8-(3-fluorophenyl)-5,6,8,9-tetrahydro-7H-pyrido[4',3':4,5]pyrrolo[2,3-b]pyridine-7-carboxamide TLC: Rf 0.57 (hexane:ethyl acetate=1:1);
$^1$H NMR (DMSO-$d_6$): δ 1.60 (s, 6H), 1.95 (s, 6H), 1.99 (s, 3H), 2.59-2.86 (m, 2H), 2.89-3.04 (m, 1H), 4.07 (dd, J=13.91, 4.03 Hz, 1H), 5.92 (s, 1H), 6.56 (s, 1H), 6.93-7.01 (m, 1H), 7.00-7.07 (m, 2H), 7.07-7.17 (m, 1H), 7.29-7.45 (m, 1H), 7.86 (dd, J=7.68, 1.56 Hz, 1H), 8.16 (dd, J=4.67, 1.56 Hz, 1H), 11.49 (s, 1H).

Example 13 (9)

8-(2,3-dihydro-1H-inden-5-yl)-N-(3,5-dimethylphenyl)-5,6,8,9-tetrahydro-7H-pyrido[4',3':4,5]pyrrolo[2,3-b]pyridine-7-carboxamide TLC: Rf 0.50 (hexane:ethyl acetate=1:1);
$^1$H NMR (DMSO-$d_6$): δ 1.90-2.04 (m, 2H), 2.20 (s, 6H), 2.69-2.89 (m, 6H), 3.06-3.21 (m, 1H), 4.23 (dd, J=13.81, 4.85 Hz, 1H), 6.59 (s, 1H), 6.67 (s, 1H), 6.98 (dd, J=7.87, 1.19 Hz, 1H), 7.04 (dd, J=7.68, 4.76 Hz, 1H), 7.08 (s, 1H), 7.11 (s, 2H), 7.18 (d, J=7.87 Hz, 1H), 7.87 (dd, J=7.68, 1.56 Hz, 1H), 8.15 (dd, J=4.76, 1.56 Hz, 1H), 8.53 (s, 1H), 11.47 (s, 1H).

Example 13 (10)

N-(3,5-dimethylphenyl)-8-(3-fluorophenyl)-5,6,8,9-tetrahydro-7H-pyrido[4',3':4,5]pyrrolo[2,3-b]pyridine-7-carboxamide TLC: Rf 0.15 (hexane:ethyl acetate=2:1);
$^1$H NMR (DMSO-$d_6$): δ 2.21 (s, 6H), 2.69-2.96 (m, 2H), 3.06-3.20 (m, 1H), 4.28 (dd, J=14.01, 4.30 Hz, 1H), 6.61 (s, 1H), 6.67 (s, 1H), 6.99-7.20 (m, 6H), 7.36-7.46 (m, 1H), 7.90 (dd, J=7.51, 1.46 Hz, 1H), 8.18 (dd, J=4.67, 1.56 Hz, 1H), 8.61 (s, 1H), 11.55 (s, 1H).

Example 14 (1) to Example 14 (5)

Using a corresponding carboxylic acid derivative in place of 3-methoxybenzoic acid, the operation having the same purpose as that in Example 8→Example 9→Example 10→Example 12 was conducted to obtain the following compound.

Example 14 (1)

7-acetyl-8-(2-fluorophenyl)-6,7,8,9-tetrahydro-5H-pyrido[4',3':4,5]pyrrolo[2,3-b]pyridine TLC: Rf 0.64 (ethyl acetate);
$^1$H NMR (DMSO-d$_6$): δ 2.16 (s, 3H), 2.75-3.00 (m, 2H), 3.29 (s, 1H), 4.16 (s, 1H), 6.80-7.07 (m, 3H), 7.07-7.14 (m, 1H), 7.14-7.24 (m, 1H), 7.30-7.43 (m, 1H), 7.86 (d, J=7.78, 1.65 Hz, 1H), 8.16 (dd, J=4.76, 1.65 Hz, 1H), 11.05 (s, 1H).

Example 14 (2)

7-acetyl-8-(1,3-benzodioxol-5-yl)-6,7,8,9-tetrahydro-5H-pyrido[4',3':4,5]pyrrolo[2,3-b]pyridine TLC: Rf 0.32 (hexane:ethyl acetate=1:2);
$^1$H NMR (DMSO-d$_6$): δ 2.13 (s, 3H), 2.68-2.97 (m, 2H), 3.10-3.26 (m, 1H), 3.87-3.99 (m, 1H), 5.98 (d, J=0.91 Hz, 1H), 5.99 (d, J=0.91 Hz, 1H), 6.58 (dd, J=7.87, 1.37 Hz, 1H), 6.71-6.77 (m, 2H), 6.84 (d, J=7.87 Hz, 1H), 7.04 (dd, J=7.87, 4.76 Hz, 1H), 7.87 (dd, J=7.87, 1.10 Hz, 1H), 8.15 (dd, J=4.76, 1.46 Hz, 1H), 11.45 (s, 1H).

Example 14 (3)

7-acetyl-8-(3,5-difluorophenyl)-6,7,8,9-tetrahydro-5H-pyrido[4',3':4,5]pyrrolo[2,3-b]pyridine TLC: Rf 0.44 (hexane:ethyl acetate=1:2);
$^1$H NMR (DMSO-d$_6$): δ 2.17 (s, 3H), 2.75-2.92 (m, 2H), 3.14-3.30 (m, 1H), 3.96-4.09 (m, 1H), 6.77 (s, 1H), 6.83-6.94 (m, 2H), 7.06 (dd, J=7.78, 4.67 Hz, 1H), 7.15-7.30 (m, 1H), 7.90 (dd, J=7.78, 1.56 Hz, 1H), 8.19 (dd, J=4.67, 1.56 Hz, 1H), 11.52 (s, 1H).

Example 14 (4)

7-acetyl-8-(2,2-difluoro-1,3-benzodioxol-5-yl)-6,7,8,9-tetrahydro-5H-pyrido[4',3':4,5]pyrrolo[2,3-b]pyridine TLC: Rf 0.50 (hexane:ethyl acetate=1:2);
$^1$H NMR (DMSO-d$_6$): δ 2.15 (s, 3H), 2.73-2.97 (m, 2H), 3.22-3.40 (m, 1H), 3.91-4.06 (m, 1H), 6.80 (s, 1H), 6.98-7.10 (m, 2H), 7.19 (d, J=1.46 Hz, 1H), 7.36 (d, J=8.42 Hz, 1H), 7.89 (dd, J=7.78, 1.55 Hz, 1H), 8.17 (dd, J=4.67, 1.55 Hz, 1H), 11.45 (s, 1H).

Example 14 (5)

7-acetyl-8-(2,3-dihydro-1H-inden-5-yl)-6,7,8,9-tetrahydro-5H-pyrido[4',3':4,5]pyrrolo[2,3-b]pyridine TLC: Rf 0.50 (ethyl acetate);
$^1$H NMR (DMSO-d$_6$): δ 1.88-2.04 (m, 2H), 2.12 (s, 3H), 2.71-2.91 (m, 6H), 3.16-3.27 (m, 1H), 3.87-3.98 (m, 1H), 6.82 (s, 1H), 6.93 (d, J=7.68 Hz, 1H), 7.00-7.08 (m, 2H), 7.16 (d, J=7.68 Hz, 1H), 7.87 (dd, J=7.69, 1.46 Hz, 1H), 8.15 (dd, J=4.76, 1.46 Hz, 1H), 11.44 (s, 1H).

Example 15

N-(3,5-dimethylphenyl)-8'-(3-fluorophenyl)-1',8'-dihydrospiro[cyclopropane-1,5'-pyrido[4',3':4,5]pyrrolo[2,3-b]pyridine]-7'(6'H)-carboxamide Using 1H-pyrrolo[2,3-b]pyridin-3-ylacetonitrile in place of 1H-indole-3-ylacetonitrile and 3-fluorobenzoic acid in place of 3-methoxybenzoic acid, the operation having the same purpose as that in Example 1→Example 2→Example 8→Example 9→Example 10→Example 5 to obtain a compound having the following physical properties.

TLC: Rf 0.31 (hexane:ethyl acetate=2:1);
$^1$H NMR (CDCl$_3$): δ 0.82-0.95 (m, 1H), 1.05-1.16 (m, 1H), 1.25-1.39 (m, 1H), 1.48-1.71 (m, 1H), 2.28 (s, 6H), 3.11 (d, J=14.64 Hz, 1H), 3.82 (d, J=14.64 Hz, 1H), 6.35 (s, 1H), 6.70 (s, 1H), 6.84 (s, 1H), 6.92-7.08 (m, 4H), 7.11-7.20 (m, 1H), 7.22-7.28 (m, 1H), 7.28-7.37 (m, 1H), 7.61 (dd, J=8.05, 1.46 Hz, 1H), 7.99 (dd, J=4.76, 1.46 Hz, 1H), 9.98 (s, 1H).

Example 16

7'-acetyl-8'-(3-fluorophenyl)-1',6',7',8'-tetrahydrospiro[cyclopropane-1,5'-pyrido[4',3':4,5]pyrrolo[2,3-b]pyridine]

Using 1H-pyrrolo[2,3-b]pyridin-3-ylacetonitrile in place of 1H-indole-3-ylacetonitrile and 3-fluorobenzoic acid in place of 3-methoxybenzoic acid, the operation having the same purpose as that in Example 1→Example 2→Example 8→Example 9→Example 10→Example 4 was conducted to obtain a compound having the following properties.

TLC: Rf 0.42 (hexane:ethyl acetate=1:2);
$^1$H NMR (CDCl$_3$): δ 0.79-0.92 (m, 1H), 0.98-1.10 (m, 1H), 1.18-1.31 (m, 1H), 1.51-1.72 (m, 1H), 2.19 (s, 3H), 3.08 (d, J=14.27 Hz, 1H), 3.83 (d, J=14.27 Hz, 1H), 6.91-7.05 (m, 2H), 7.08-7.18 (m, 2H), 7.21 (d, J=1H), 7.24-7.37 (m, 1H), 7.61 (dd, J=7.87, 1.28 Hz, 1H), 7.89 (d, J=4.94 Hz, 1H), 10.43 (s, 1H).

Example 17

1-(1-methyl-1H-indol-3-yl)cyclopropanecarbonitrile 1-(1H-indol-3-yl)cyclopropanecarbonitrile (183 mg) was dissolved in N,N-dimethylformamide (2 mL) and sodium hydride (60% in oil, 45 mg) was added under ice cooling, followed by stirring for 5 minutes. To the reaction solution, methyl iodide (0.07 mL) was added, followed by stirring at room temperature for one hour. To the reaction solution, water was added, followed by extraction with ethyl acetate. The organic layer was washed with saturated saline, dried over anhydrous magnesium sulfate and then concentrated. The residue was purified by silica gel column chromatography (parallel separation purification system) to obtain the titled compound having the following physical properties (196 mg).

TLC: Rf 0.30 (hexane:ethyl acetate=4:1);
$^1$H NMR (CDCl$_3$): δ 1.30-1.39 (m, 2H), 1.57-1.70 (m, 2H), 3.75 (s, 3H), 6.98 (s, 1H), 7.15-7.23 (m, 1H), 7.24-7.37 (m, 2H), 7.74-7.85 (m, 1H).

Example 18 (1) to Example 18 (2)

Using the compound prepared in Example 11 in place of the compound prepared in Example 1, 3-fluorobenzaldehyde in place of 1,3-benzodioxol-5-carboaldehyde, and acetic anhydride or alternatively methyl chloride carbonate, the operation having the same purpose as that in Example 2→Example 3→Example 4 was conducted to obtain the following compound.

Example 18 (1)

2-acetyl-1-(3-fluorophenyl)-9-methyl-1,2,3,9-tetrahydrospiro[β-carboline-4,1'-cyclopropane]

TLC: Rf 0.33 (hexane:ethyl acetate=2:1);
$^1$H NMR (DMSO-d$_6$): δ 0.75-0.92 (m, 1H), 1.03-1.22 (m, 2H), 1.53-1.77 (m, 1H), 2.11 (s, 3H), 3.21-3.32 (m, 1H), 3.39 (s, 3H), 3.52 (d, J=14.27 Hz, 1H), 6.90-7.09 (m, 4H), 7.09-7.25 (m, 2H), 7.25-7.34 (m, 1H), 7.35-7.50 (m, 2H).

Example 18 (2)

methyl 1-(3-fluorophenyl)-9-methyl-1,9-dihydrospiro[β-carboline-4,1'-cyclopropane]-2(3H)-carboxylate TLC: Rf 0.60 (hexane:ethyl acetate=2:1);
$^1$H NMR (DMSO-d$_6$): δ 0.77-1.01 (m, 2H), 1.01-1.14 (m, 1H), 1.60-1.71 (m, 1H), 3.32-3.42 (m, 5H), 3.67 (s, 3H), 6.59 (s, 1H), 6.94-7.07 (m, 3H), 7.09-7.16 (m, 1H), 7.16-7.25 (m, 1H), 7.31 (d, J=8.05 Hz, 1H), 7.37-7.48 (m, 2H).

Example 19

8-(3-fluorophenyl)-9-methyl-6,9-dihydro-5H-pyrido[4',3':4,5]pyrrolo[2,3-b]pyridine (compound A) and 8-(3-fluorophenyl)-1-methyl-5,6-dihydro-1H-pyrido[4',3':4,5]pyrrolo[2,3-b]pyridine (compound B)

Compound A
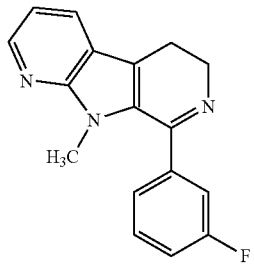

Compound B
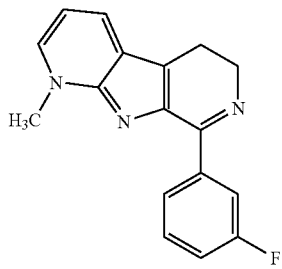

8-(3-fluorophenyl)-5,6-dihydro-1H-pyrido[4',3':4,5]pyrrolo[2,3-b]pyridine (209 mg) was dissolved in N,N-dimethylformamide (8 mL) and sodium hydride (60% in oil, 42 mg) was added under ice cooling, followed by stirring for five minutes. To the reaction solution, methyl iodide (0.06 mL) was added, followed by stirring at 0° C. for 30 minutes. To the reaction solution, water was added, followed by extraction with ethyl acetate. The organic layer was washed with saturated saline, dried over anhydrous sodium sulfate and then concentrated. The residue was purified by silica gel column chromatography (hexane:ethyl acetate=3:2→methylene chloride:methanol=85:15) to obtain the titled compound A (173 mg) and the titled compound B (45 mg), each having the following physical properties.

Compound A:
TLC: Rf 0.33 (hexane:ethyl acetate=1:1);
$^1$H NMR (CDCl$_3$): δ 2.84-2.96 (m, 2H), 3.47 (s, 3H), 3.91-4.04 (m, 2H), 7.09-7.23 (m, 2H), 7.29-7.39 (m, 2H), 7.39-7.49 (m, 1H), 7.96 (dd, J=7.87, 1.55 Hz, 1H), 8.44 (dd, J=4.67, 1.55 Hz, 1H).

Compound B:
TLC: Rf 0.29 (methylene chloride:methanol=9:1);
$^1$H NMR (CDCl$_3$): δ 2.92-3.06 (m, 2H), 3.97-4.16 (m, 2H), 4.34 (s, 3H), 6.91 (dd, J=7.59, 6.00 Hz, 1H), 7.05-7.19 (m, 1H), 7.32-7.48 (m, 1H), 7.69 (d, J=6.04 Hz, 1H), 8.02-8.21 (m, 3H).

Example 20 (1) to Example 20 (2)

Using the compound A or the compound B prepared in Example 19 in place of the compound prepared in Example 9, the operation having the same purpose as that in Example 10 Example 11 was conducted to obtain the following compound.

Example 20 (1)

N-(3,5-dimethylphenyl)-8-(3-fluorophenyl)-9-methyl-5,6,8,9-tetrahydro-7H-pyrido[4',3':4,5]pyrrolo[2,3-b]pyridine-7-carboxamide TLC: Rf 0.34 (hexane:ethyl acetate=2:1);
$^1$H NMR (DMSO-d$_6$): δ 2.21 (s, 6H), 2.75-2.97 (m, 2H), 3.00-3.20 (m, 1H), 3.43 (s, 3H), 4.13-4.40 (m, 1H), 6.62 (s, 1H), 6.80 (s, 1H), 6.96-7.26 (m, 6H), 7.32-7.49 (m, 1H), 7.96 (dd, J=7.68, 1.46 Hz, 1H), 8.25 (dd, J=4.76, 1.46 Hz, 1H), 8.65 (s, 1H).

Example 20 (2)

N-(3,5-dimethylphenyl)-8-(3-fluorophenyl)-1-methyl-1,5,6,8-tetrahydro-7H-pyrido[4',3':4,5]pyrrolo[2,3-b]pyridine-7-carboxamide TLC: Rf 0.41 (methylene chloride:methanol=9:1);
$^1$H NMR (DMSO-d$_6$): δ 2.20 (s, 6H), 2.73-2.84 (m, 1H), 2.85-3.01 (m, 1H), 3.02-3.18 (m, 1H), 4.18 (s, 3H), 4.29-4.48 (m, 1H), 6.58 (s, 1H), 6.62 (s, 1H), 6.91 (dd, J=7.32, 6.04 Hz, 1H), 7.01-7.12 (m, 1H), 7.13 (s, 2H), 7.17-7.29 (m, 2H), 7.29-7.43 (m, 1H), 8.02 (d, J=6.04 Hz, 1H), 8.06 (d, J=7.32 Hz, 1H), 8.58 (s, 1H).

Example 21

7-acetyl-8-(3-fluorophenyl)-9-methyl-6,7,8,9-tetrahydro-5H-pyrido[4',3':4,5]pyrrolo[2,3-b]pyridine Using the compound A prepared in Example 19 in place of the compound prepared in Example 9, the operation having the same purpose as that in Example 10→Example 12 was conducted to obtain the following compound having the following physical properties.

TLC: Rf 0.33 (hexane:ethyl acetate=1:1);
$^1$H NMR (DMSO-d$_6$): δ 2.15 (s, 3H), 2.69-2.99 (m, 2H), 3.15-3.30 (m, 1H), 3.40 (s, 3H), 3.88-4.10 (m, 1H), 6.92-7.29 (m, 5H), 7.33-7.49 (m, 1H), 7.89-8.01 (m, 1H), 8.24 (dd, J=4.76, 1.46 Hz, 1H).

Example 22

N-(4,6-dimethylpyridin-2-yl)-8-(3-fluorophenyl)-5,6,8,9-tetrahydro-7H-pyrido[4',3':4,5]pyrrolo[2,3-b]pyridine-7-carboxamide To a tetrahydrofuran (1 mL) solution of phenyl chloroformate (157 mg), a tetrahydrofuran (1 mL) solution of 6-amino-2,4-lutidine (122 mg) and triethylamine (0.14 mL) were added under ice cooling, followed by stirring for one hour. The resulting mixture was added to a tetrahydrofuran (0.5 mL) solution of 8-(3-fluorophenyl)-5,6,7,8-tetrahydro-1H-pyrido[4',3':4,5]pyrrolo[2,3-b]pyridine (prepared by conducting the operation having the same purpose as that in Example 8 Example 9 Example 10 using 3-fluorobenzoic acid in place of 3-methoxybenzoic acid) (60 mg) and triethylamine (31 µL), followed by stirring at 70° C. for 2 hours. To the reaction mixture, an aqueous saturated sodium hydrogen carbonate solution was added, followed by extraction with ethyl acetate. The organic layer was washed with an aqueous saturated sodium hydrogen carbonate solution and saturated saline, dried over anhydrous sodium sulfate and then concentrated. The residue was purified by silica gel column chromatography (parallel separation purification system) and recrystallized from a mixed solvent of ethyl acetate and hexane to obtain the titled compound having the following physical properties (38.7 mg).

TLC: Rf 0.40 (ethyl acetate:hexane=2:1);
$^1$H NMR (DMSO-$d_6$): δ 2.22 (s, 3H), 2.33 (s, 3H), 2.68-2.81 (m, 1H), 2.82-3.00 (m, 1H), 3.06-3.22 (m, 1H), 4.37 (dd, J=14.00, 4.50 Hz, 1H), 6.70 (s, 2H), 7.00-7.22 (m, 4H), 7.36-7.45 (m, 1H), 7.46 (s, 1H), 7.89 (dd, J=8.00, 1.50 Hz, 1H), 8.17 (dd, J=4.50, 1.50 Hz, 1H), 9.28 (s, 1H), 11.53 (s, 1H).

Example 22 (1)

N-(2,2-difluoro-1,3-benzodioxol-5-yl)-8-(3-fluorophenyl)-5,6,8,9-tetrahydro-7H-pyrido[4',3':4,5]pyrrolo[2,3-b]pyridine-7-carboxamide Using (2,2-difluoro-1,3-benzodioxol-5-yl)amine in place of 6-amino-2,4-lutidine, the operation having the same purpose as that in Example 22 was conducted to obtain the titled compound having the following physical properties.

TLC: Rf 0.66 (hexane:ethyl acetate=1:2);
$^1$H NMR (DMSO-$d_6$): δ 2.69-3.00 (m, 2H), 3.03-3.25 (m, 1H), 4.28 (dd, J=14.18, 4.48 Hz, 1H), 6.67 (s, 1H), 6.99-7.24 (m, 5H), 7.29 (d, J=8.78 Hz, 1H), 7.35-7.47 (m, 1H), 7.61 (d, J=1.83 Hz, 1H), 7.90 (dd, J=7.96, 1.56 Hz, 1H), 8.18 (dd, J=4.67, 1.56 Hz, 1H), 8.96 (s, 1H), 11.55 (s, 1H).

Example 23

3-fluoro-N-{2-[2-(trimethylsilyl)-1H-pyrrolo[3,2-c]pyridin-3-yl]ethyl}benzamide

A suspension of 3-iodo-4-pyridineamine (594 mg), 3-fluoro-N-[4-(trimethylsilyl)-3-butynyl]benzamide (710 mg), palladium acetate (61 mg), triphenylphosphine (142 mg), sodium acetate (443 mg) and lithium chloride (115 mg) in N,N-dimethylformamide (6 mL) and acetonitrile (3 mL) was irradiated with microwave (100 W) for 30 minutes, poured into water and then extracted with ethyl acetate. The organic layer was washed in turn with an aqueous saturated sodium hydrogen carbonate solution and saturated saline, dried over anhydrous sodium sulfate and then concentrated. The residue was purified by silica gel column chromatography (parallel separation purification system) to obtain the titled compound having the following physical properties (404.8 mg).

TLC: Rf 0.51 (methanol: dichloromethane=1:4);
$^1$H NMR (CDCl$_3$): δ 0.41 (s, 9H), 3.23 (t, J=7.2 Hz, 2H), 3.67-3.84 (m, 2H), 6.85-6.98 (m, 1H), 7.06-7.20 (m, 1H), 7.27-7.39 (m, 2H), 7.43-7.55 (m, 2H), 8.20 (d, J=5.9 Hz, 1H), 8.79 (s, 1H), 9.08 (s, 1H).

Example 24

3-fluoro-N-[2-(1H-pyrrolo[3,2-c]pyridin-3-yl)ethyl]benzamide

To a dichloromethane (10 mL) solution of the compound (400 mg) prepared in Example 23, aluminum chloride (1.51 g) was added under ice cooling, followed by stirring at room temperature overnight. The reaction mixture was poured into a cold aqueous saturated sodium hydrogen carbonate solution, followed by extraction with a mixed solvent of ethyl acetate and tetrahydrofuran. The organic layer was washed in turn with an aqueous saturated sodium hydrogen carbonate solution and saturated saline, dried over anhydrous sodium sulfate and then concentrated. The residue was purified by silica gel column chromatography (parallel separation purification system) to obtain the titled compound having the following physical properties (137.9 mg).

TLC: Rf 0.36 (methanol: dichloromethane=1:4);
$^1$H NMR (CD$_3$OD): δ 3.13 (t, J=7.0 Hz, 2H), 3.69 (t, J=7.0 Hz, 2H), 7.19-7.31 (m, 2H), 7.39 (dd, J=6.0, 1.0 Hz, 1H), 7.41-7.52 (m, 2H), 7.54-7.62 (m, 1H), 8.11 (d, J=6.0 Hz, 1H), 8.85 (d, J=1.0 Hz, 1H).

Example 25

N-(3,5-dimethylphenyl)-6-(3-fluorophenyl)-5,6,8,9-tetrahydro-7H-pyrido[3',4':4,5]pyrrolo[2,3-c]pyridine-7-carboxamide Using the compound prepared in Example 24 in place of the compound prepared in Example 8, the operation having the same purpose as that in Example 9→Example 10→Example 11 was conducted to obtain the titled compound having the following physical properties.

TLC: Rf 0.28 (methylene chloride:methanol=9:1);
$^1$H NMR (CDCl$_3$): δ 2.28 (s, 6H), 2.81-2.93 (m, 1H), 2.94-3.10 (m, 1H), 3.31-3.49 (m, 1H), 3.94 (dd, J=14.36, 5.03 Hz, 1H), 6.73 (s, 1H), 6.75 (s, 1H), 6.93-7.04 (m, 4H), 7.08 (d, J=7.68 Hz, 1H), 7.15-7.20 (m, 1H), 7.21-7.31 (m, 1H), 8.22 (dd, J=5.67, 1.10 Hz, 1H), 8.73 (s, 1H).

Example 26

7-acetyl-6-(3-fluorophenyl)-6,7,8,9-tetrahydro-5H-pyrido[3',4':4,5]pyrrolo[2,3-c]pyridine Using the compound prepared in Example 24 in place of the compound prepared in Example 8, the operation having the same purpose as that in Example 9 Example 10 Example 12 was conducted to obtain the titled compound having the following physical properties.

TLC: Rf 0.20 (methylene chloride:methanol=9:1);
$^1$H NMR (CDCl$_3$): δ 2.23 (s, 3H), 2.93-3.07 (m, 2H), 3.35-3.51 (m, 1H), 3.88-4.01 (m, 1H), 6.93-7.12 (m, 4H), 7.18-7.41 (m, 2H), 8.25 (d, J=5.49 Hz, 1H), 8.78 (s, 1H).

Example 27

(+)-2-acetyl-1-(3-fluorophenyl)-1,2,3,9-tetrahydrospiro[β-carboline-4,1'-cyclopropane] and (−)-2-acetyl-1-(3-fluorophenyl)-1,2,3,9-tetrahydrospiro[β-carboline-4,1'-cyclopropane]

The compound prepared in Example 6 (21) was optically resolved using HPLC (column used: CHIRALPAK AD manufactured by Daicel Chemical Industries, Ltd.; development solvent: 2-propanol: hexane=1:1) to obtain (−) isomer and (+) isomer, each having the following physical properties.
(−) isomer:
HPLC retention time (min)=10.0;
$[α]_D$=−138.9 (MeOH, c=0.21).
(+) isomer:
HPLC retention time (min)=12.9;
$[α]_D$=+144.1 (MeOH, c=0.26).

Example 27 (1)

(+)-N-(3,5-dimethylphenyl)-8-(3-fluorophenyl)-5,6,8,9-tetrahydro-7H-pyrido[4',3':4,5]pyrrolo[2,3-b]pyridine-7-carboxamide and (−)-N-(3,5-dimethylphenyl)-8-(3-fluorophenyl)-5,6,8,9-tetrahydro-7H-pyrido[4',3':4,5]pyrrolo[2,3-b]pyridine-7-carboxamide Using the compound prepared in Example 13 (10) in place of the compound prepared in Example 6 (21), the operation having the same purpose as that in Example 27 was conducted to obtain the titled compound having the following physical properties.
(−) isomer:
$[α]_D$=−205.2 (MeOH, c=0.355).
(+) isomer:
$[α]_D$=+206.5 (MeOH, c=0.206).

Example 28

(−)-2-ethanethioyl-1-(3-fluorophenyl)-1,2,3,9-tetrahydrospiro[β-carboline-4,1'-cyclopropane]

The (−) isomer (40 mg) prepared in Example 27 was suspended in toluene (1.2 mL) and 2,4-bis(4-methoxyphenyl)-1,3-dithia-2,4-diphosphetane-2,4-disulfide (Lawesson' reagent, 49 mg) was added, followed by refluxing for one hour. The reaction solution was air-cooled and filtered, and then the filtrate was concentrated. The residue was purified by silica gel column chromatography (hexane:ethyl acetate=4:1) to obtain the titled compound having the following physical properties (29 mg).
TLC: Rf 0.44 (hexane:ethyl acetate=4:1);
$^1$H NMR (CDCl$_3$): δ 0.75-0.95 (m, 1H), 1.00-1.14 (m, 1H), 1.34-1.48 (m, 1H), 1.69-1.88 (m, 1H), 2.76 (s, 3H), 3.47 (dd, J=14.00, 1.56 Hz, 1H), 3.95 (dd, J=14.00, 1.56 Hz, 1H), 6.97-7.13 (m, 2H), 7.15-7.23 (m, 1H), 7.24-7.43 (m, 5H), 7.90 (s, 1H), 8.46 (s, 1H);
$[α]_D$=−379.3 (MeOH, c=0.20).

Example 28 (1)

(+)-2-ethanethioyl-1-(3-fluorophenyl)-1,2,3,9-tetrahydrospiro[β-carboline-4,1'-cyclopropane]

Using the (+) isomer prepared in Example 27 in place of the (−) isomer prepared in Example 27, the operation having the same purpose as that in Example 28 was conducted to obtain the titled compound having the following physical properties.
TLC: Rf 0.45 (hexane:ethyl acetate=4:1);
$^1$H NMR (CDCl$_3$): δ 0.74-0.92 (m, 1H), 0.99-1.16 (m, 1H), 1.34-1.48 (m, 1H), 1.70-1.88 (m, 1H), 2.76 (s, 3H), 3.47 (dd, J=14.00, 1.37 Hz, 1H), 3.94 (dd, J=14.00, 1.37 Hz, 1H), 6.96-7.12 (m, 2H), 7.14-7.24 (m, 1H), 7.24-7.44 (m, 5H), 7.88 (s, 1H), 8.46 (s, 1H).
$[α]_D$=+358.5 (MeOH, c=0.22).

Example 29

N-(3,5-dimethylphenyl)-8'-(3-fluorophenyl)-1'-methyl-1',8'-dihydrospiro[cyclopropane-1,5'-pyrido[4',3':4,5]pyrrolo[2,3-b]pyridine]-7'(6'H)-carboxamide The compound (188 mg) prepared in Example 15 was suspended in toluene (8 mL) and methyl p-toluenesulfonate (0.32 mL) was added, followed by refluxing for 2 hours. After the reaction solution was air-cooled, an aqueous saturated sodium carbonate solution was added, followed by extraction with ethyl acetate. The organic layer was washed with saturated saline, dried over anhydrous sodium sulfate and then concentrated. The residue was purified by silica gel column chromatography (hexane:ethyl acetate=1:2→methylene chloride:methanol=85:15) to obtain the titled compound having the following physical properties (122 mg).
TLC: Rf 0.37 (methylene chloride:methanol=9:1);
$^1$H NMR (DMSO-d$_6$): δ 0.71-0.87 (m, 1H), 0.88-1.02 (m, 1H), 1.06-1.20 (m, 1H), 1.37-1.55 (m, 1H), 2.20 (s, 6H), 3.40 (d, J=14.64 Hz, 1H), 3.71 (d, J=14.64 Hz, 1H), 4.17 (s, 3H), 6.59 (s, 1H), 6.73 (s, 1H), 6.84 (dd, J=7.32, 6.04 Hz, 1H), 7.00-7.30 (m, 5H), 7.32-7.44 (m, 1H), 7.84 (d, J=7.32 Hz, 1H), 8.00 (d, J=6.04 Hz, 1H), 8.51 (s, 1H).

Example 29 (1) to Example 29 (6)

Using the (−) isomer and the (+) isomer prepared in Example 27 (1) as well as the compounds prepared in Examples 16, 11, 13 (1) or 13 (7) in place of the compound prepared in Example 15, the operation having the same purpose as that in Example 29 was conducted to obtain the following compound.

Example 29 (1)

(+)-N-(3,5-dimethylphenyl)-8-(3-fluorophenyl)-1-methyl-1,5,6,8-tetrahydro-7H-pyrido[4',3':4,5]pyrrolo[2,3-b]pyridine-7-carboxamide TLC: Rf 0.33 (methylene chloride:methanol=9:1);
$^1$H NMR (DMSO-d$_6$): δ 2.20 (s, 6H), 2.69-2.83 (m, 1H), 2.85-3.02 (m, 1H), 3.02-3.21 (m, 1H), 4.18 (s, 3H), 4.28-4.48 (m, 1H), 6.58 (s, 1H), 6.62 (s, 1H), 6.84-6.98 (m, 1H), 7.01-7.29 (m, 5H), 7.30-7.42 (m, 1H), 7.91-8.22 (m, 2H), 8.58 (s, 1H);
$[α]_D$=+126.9 (MeOH, c=0.22).

Example 29 (2)

(−)-N-(3,5-dimethylphenyl)-8-(3-fluorophenyl)-1-methyl-1,5,6,8-tetrahydro-7H-pyrido[4',3':4,5]pyrrolo[2,3-b]pyridine-7-carboxamide TLC: Rf 0.46 (methylene chloride:methanol=9:1);
$^1$H NMR (DMSO-d$_6$): δ 2.20 (s, 6H), 2.69-2.85 (m, 1H), 2.84-3.02 (m, 1H), 3.02-3.20 (m, 1H), 4.18 (s, 3H), 4.26-4.47

(m, 1H), 6.58 (s, 1H), 6.62 (s, 1H), 6.84-7.00 (m, 1H), 7.02-7.30 (m, 5H), 7.31-7.44 (m, 1H), 7.89-8.16 (m, 2H), 8.58 (s, 1H);

[α]$_D$=−119.7 (MeOH, c=0.20).

Example 29 (3)

7'-acetyl-8'-(3-fluorophenyl)-1'-methyl-1',6',7',8'-tetrahydrospiro[cyclopropane-1,5'-pyrido[4',3':4,5]pyrrolo[2,3-b]pyridine]

TLC: Rf 0.34 (methylene chloride:methanol=9:1);

$^1$H NMR (CDCl$_3$): δ 1.60-1.96 (m, 4H), 2.02-2.19 (m, 1H), 2.23-2.38 (m, 1H), 2.42-2.63 (m, 2H), 3.56-3.70 (m, 1H), 3.71-4.02 (m, 6H), 6.77 (d, J=8.97 Hz, 1H), 7.72-7.93 (m, 4H), 8.06 (dd, J=8.97, 2.20 Hz, 1H), 8.24 (d, J=2.20 Hz, 1H).

Example 29 (4)

N-(3,5-dimethylphenyl)-8-(3-methoxyphenyl)-1-methyl-1,5,6,8-tetrahydro-7H-pyrido[4',3':4,5]pyrrolo[2,3-b]pyridine-7-carboxamide TLC: Rf 0.30 (methylene chloride:methanol=9:1);

$^1$H NMR (DMSO-d$_6$): δ 2.19 (s, 6H), 2.67-2.83 (m, 1H), 2.84-3.00 (m, 1H), 3.03-3.22 (m, 1 H), 3.68 (s, 3H), 4.16 (s, 3H), 4.26-4.45 (m, 1H), 6.57 (s, 1H), 6.60 (s, 1H), 6.81 (dd, J=7.96, 2.47 Hz, 1H), 6.85-6.97 (m, 2H), 7.01 (s, 1H), 7.14 (s, 2H), 7.21 (t, J=7.96 Hz, 1H), 8.00 (d, J=6.22 Hz, 1H), 8.02-8.09 (m, 1H), 8.55 (s, 1H).

Example 29 (5)

N-(3,5-dimethylphenyl)-8-(2-fluorophenyl)-1-methyl-1,5,6,8-tetrahydro-7H-pyrido[4',3':4,5]pyrrolo[2,3-b]pyridine-7-carboxamide TLC: Rf 0.34 (methylene chloride:methanol=9:1);

$^1$H NMR (DMSO-d$_6$): δ 2.18 (s, 6H), 2.67-2.99 (m, 2H), 3.09-3.27 (m, 1H), 4.10 (s, 3H), 4.20-4.37 (m, 1H), 6.55 (s, 1H), 6.75-6.95 (m, 3H), 6.97-7.07 (m, 1H), 7.09 (s, 2H), 7.12-7.22 (m, 1H), 7.24-7.38 (m, 1H), 7.98 (d, J=6.04 Hz, 1H), 8.04 (d, J=6.77 Hz, 1H), 8.54 (s, 1H).

Example 29 (6)

8-(2,2-difluoro-1,3-benzodioxol-5-yl)-N-(3,5-dimethylphenyl)-1-methyl-1,5,6,8-tetrahydro-7H-pyrido[4',3':4,5]pyrrolo[2,3-b]pyridine-7-carboxamide TLC: Rf 0.36 (methylene chloride:methanol=9:1);

$^1$H NMR (DMSO-d$_6$): δ 2.20 (s, 6H), 2.66-2.85 (m, 1H), 2.86-3.02 (m, 1H), 3.03-3.22 (m, 1 H), 4.16 (s, 3H), 4.26-4.48 (m, 1H), 6.58 (s, 1H), 6.61 (s, 1H), 6.83-6.98 (m, 1H), 7.12 (s, 2 H), 7.20 (dd, J=8.23, 0.91 Hz, 1H), 7.32 (d, J=8.23 Hz, 1H), 7.37 (d, J=0.91 Hz, 1H), 8.01 (d, J=6.22 Hz, 1H), 8.05 (d, J=6.95 Hz, 1H), 8.55 (s, 1H).

Example 30 tert-butyl 6-(3-fluorophenyl)-2-methoxy-5,6,8,9-tetrahydro-7H-pyrido[4',3':4,5]pyrrolo[3,2-b]pyridine-7-carboxylate (compound A) and tert-butyl 2-chloro-6-(3-fluorophenyl)-5,6,8,9-tetrahydro-7H-pyrido[4',3':4,5]pyrrolo[3,2-b]pyridine-7-carboxylate (compound B)

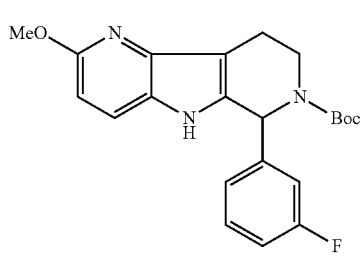

Compound (A)

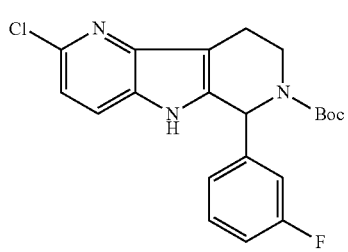

Compound (B)

An ethanol (20 mL) suspension of 5-methoxy-3-(2-nitroethyl)-1H-pyrrolo[3,2-b]pyridine (1.11 g) and palladium hydroxide/carbon (550 mg) was heated to 80° C. and an ethanol (2 mL) solution of hydrazine monohydrate (628 mg) was added dropwise, followed by stirring at 80° C. for one hour. The reaction mixture was air-cooled to room temperature, filtered with Celite (trade name), and then filtrate was concentrated to obtain [2-(5-methoxy-1H-pyrrolo[3,2-b]pyridin-3-yl)ethyl]amine. The resulting product was dissolved in N,N-dimethylformamide (15 mL) and 3-fluorobenzoic acid (802 mg), HOAt (751 mg) and EDC hydrochloride (1.06 g) were sequentially added, followed by stirring at room temperature until materials disappear. To the reaction mixture, a cold aqueous saturated sodium hydrogen carbonate solution was added, followed by extraction with ethyl acetate. The organic layer was washed with saturated saline, dried over anhydrous sodium sulfate and then concentrated. The residue was dissolved in methanol (15 mL) and an aqueous 1N sodium hydroxide solution (3 mL) was added, followed by stirring for fifteen minutes. The reaction mixture was diluted with water and then extracted with ethyl acetate. The organic layer was washed with saturated saline, dried over anhydrous sodium sulfate and then concentrated. The residue was purified by silica gel column chromatography (hexane:ethyl acetate=1:1) to obtain 3-fluoro-N-[2-(5-methoxy-1H-pyrrolo[3,2-b]pyridin-3-yl)ethyl]benzamide. The resulting product was dissolved in anhydrous acetonitrile (76 mL) and N,N-diethylaniline (two drops) was added, followed by deaeration with ultrasonic wave, argon substitution and further addition of phosphorus oxychloride (2.33 mL), followed by stirring at 80 to 85° C. overnight. The reaction mixture was air-cooled to room temperature and then concentrated. After the residue was dissolved in a mixed solvent of tetrahydrofuran and ethyl acetate, the solution was washed with an aqueous saturated sodium hydrogen carbonate solution and saturated saline, dried over anhydrous sodium sulfate and then concentrated to obtain a mixture of 6-(3-fluorophenyl)-2-methoxy-8,9-dihydro-5H-pyrido[4',3':4,5]pyrrolo[3,2-b]pyridine and 2-chloro-6-(3-fluorophenyl)-8,9-dihydro-5H-pyrido[4',3':4,5]pyrrolo[3,2-b]pyridine. The mixture was dissolved in methanol (14 mL) and sodium borohydride (469 mg) was added at room temperature, followed by stirring until materials disappear. To the reaction mixture, an aqueous saturated sodium hydrogen carbonate solution was added, followed by extraction with ethyl acetate. The organic layer was washed with saturated saline, dried over anhydrous sodium sulfate and then concentrated to obtain a mixture of 6-(3-fluorophenyl)-2-methoxy-6,7,8,9-tetrahydro-5H-pyrido[4',3':4,5]pyrrolo[3,2-b]pyridine and 2-chloro-6-(3-fluorophenyl)-6,7,8,9-tetrahydro-5H-pyrido[4',3':4,5]pyrrolo[3,2-b]pyridine. The mixture was dissolved in tetrahydrofuran (13 mL) and di-tert-butyl dicarbonate (960 mg) was added at room temperature, followed by stirring until materials disappear. The reaction mixture was concentrated. The residue was purified by silica gel column chromatography (hexane:ethyl acetate=5:1) to obtain the titled compound A (444 mg) and the titled compound B (650 mg), each having the following physical properties.

Compound A

TLC: Rf 0.41 (hexane:ethyl acetate=3:1);

$^1$H NMR (CDCl$_3$): δ 1.50 (s, 9H), 2.79-3.21 (m, 3H), 4.00 (s, 3H), 4.29 (s, 1H), 6.44 (s, 1H), 6.58 (d, J=8.60 Hz, 1H), 6.91-7.04 (m, 2H), 7.07 (d, J=7.68 Hz, 1H), 7.17-7.36 (m, 1H), 7.46 (d, J=8.60 Hz, 1H), 7.65 (s, 1H).

Compound B

TLC: Rf 0.28 (hexane:ethyl acetate=3:1);

$^1$H NMR (CDCl$_3$): δ 1.50 (s, 9H), 2.79-3.17 (m, 3H), 4.29 (s, 1H), 6.46 (s, 1H), 6.92-7.08 (m, 3H), 7.11 (d, J=8.42 Hz, 1H), 7.19-7.39 (m, 1H), 7.52 (d, J=8.42 Hz, 1H), 7.97 (s, 1H).

Example 31

N-(3,5-dimethylphenyl)-6-(3-fluorophenyl)-2-methoxy-5,6,8,9-tetrahydro-7H-pyrido[4',3':4,5]pyrrolo[3,2-b]pyridine-7-carboxamide

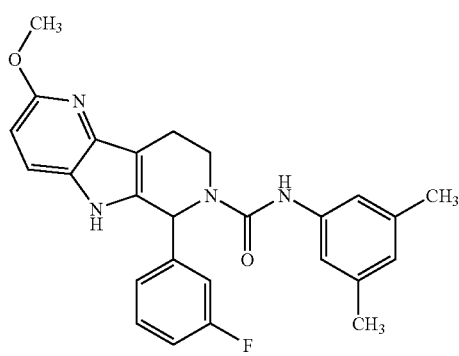

Step A:

Under an argon atmosphere, trifluoroacetic acid (1 mL) was added to the compound A (135 mg) prepared in Example 30 at room temperature, followed by stirring until materials disappear. The reaction mixture was concentrated to obtain 6-(3-fluorophenyl)-2-methoxy-6,7,8,9-tetrahydro-5H-pyrido[4',3':4,5]pyrrolo[3,2-b]pyridine.

Step B:

To the compound obtained in the step A, anhydrous tetrahydrofuran (1 mL) and triethylamine (142 μL) were sequentially added and 1-isocyanato-3,5-dimethylbenzene (50 μL) was added, followed by stirring until materials disappear. To the reaction mixture, water was added, followed by extraction with ethyl acetate. The organic layer was purified by silica gel column chromatography (hexane:ethyl acetate=2:1) to obtain the titled compound having the following physical properties (147 mg).

TLC: Rf 0.24 (hexane:ethyl acetate=2:1);

$^1$H NMR (DMSO-d$_6$): δ 2.21 (s, 6H), 2.74-2.93 (m, 2H), 3.02-3.20 (m, 1H), 3.86 (s, 3H), 4.19-4.36 (m, 1H), 6.53 (d, J=8.60 Hz, 1H), 6.60 (s, 1H), 6.66 (s, 1H), 6.96-7.04 (m, 1H), 7.05-7.20 (m, 4H), 7.33-7.46 (m, 1H), 7.61 (d, J=8.60 Hz, 1H), 8.59 (s, 1H), 11.08 (s, 1H).

Example 32 tert-butyl 6-(3-fluorophenyl)-5,6,8,9-tetrahydro-7H-pyrido[4',3':4,5]pyrrolo[3,2-b]pyridine-7-carboxylate The compound B (320 mg) prepared in Example 30 and 10% palladium/carbon (33 mg) were suspended in methanol (3 mL), followed by hydrogen substitution and further stirring at room temperature until materials disappear. The reaction mixture was filtered with Celite (trade name) after argon substitution. The filtrate was concentrated to obtain the titled compound. The resulting compound was used for the following reaction without being purified.

Example 33 (1) to Example 33 (2)

Using the compound B prepared in Example 30 or the compound prepared in Example 32 in place of the compound A prepared in Example 30, the operation having the same purpose as that in Example 31 was conducted to obtain the following compound.

Example 33 (1)

2-chloro-N-(3,5-dimethylphenyl)-6-(3-fluorophenyl)-5,6,8,9-tetrahydro-7H-pyrido[4',3':4,5]pyrrolo[3,2-b]pyridine-7-carboxamide TLC: Rf 0.35 (hexane:ethyl acetate=2:1);

$^1$H NMR (DMSO-d$_6$): δ 2.21 (s, 6H), 2.75-2.97 (m, 2H), 3.03-3.25 (m, 1H), 4.22-4.37 (m, 1 H), 6.60 (s, 1H), 6.71 (s, 1H), 6.96-7.23 (m, 6H), 7.33-7.48 (m, 1H), 7.75 (d, J=8.42 Hz, 1H), 8.62 (s, 1H), 11.54 (s, 1H).

Example 33 (2)

N-(3,5-dimethylphenyl)-6-(3-fluorophenyl)-5,6,8,9-tetrahydro-7H-pyrido[4',3':4,5]pyrrolo[3,2-b]pyridine-7-carboxamide TLC: Rf 0.40 (hexane:ethyl acetate=2:1);

$^1$H NMR (DMSO-d$_6$), 2.21 (s, 6H), 2.81-2.95 (m, 2H), 3.07-3.22 (m, 1H), 4.30 (dd, J=13.54, 2.56 Hz, 1H), 6.61 (s, 1H), 6.71 (s, 1H), 6.99-7.22 (m, 6H), 7.36-7.47 (m, 1H), 7.68 (dd, J=8.23, 1.46 Hz, 1H), 8.29 (dd, J=4.67, 1.37 Hz, 1H), 8.62 (s, 1H), 11.26 (s, 1H).

Example 34 (1) to Example 34 (3)

Using the compound A prepared in Example 30 or alternatively the compound B prepared in Example 30 or the compound prepared in Example 32, the operation having the same purpose as that in step A of Example 31→Example 4 was conducted to obtain the following compound.

Example 34 (1)

7-acetyl-6-(3-fluorophenyl)-2-methoxy-6,7,8,9-tetrahydro-5H-pyrido[4',3':4,5]pyrrolo[3,2-b]pyridine TLC: Rf 0.66 (ethyl acetate);
$^1$H NMR (DMSO-$d_6$): δ 2.16 (s, 3H), 2.74-2.91 (m, 2H), 3.11-3.28 (m, 1H), 3.86 (s, 3H), 3.91-4.04 (m, 1H), 6.52 (d, J=8.60 Hz, 1H), 6.81 (s, 1H), 6.91-7.00 (m, 1H), 7.03 (d, J=7.68 Hz, 1H), 7.07-7.21 (m, 1H), 7.31-7.44 (m, 1H), 7.61 (d, J=8.60 Hz, 1H), 11.06 (s, 1H).

Example 34 (2)

7-acetyl-2-chloro-6-(3-fluorophenyl)-6,7,8,9-tetrahydro-5H-pyrido[4',3':4,5]pyrrolo[3,2-b]pyridine TLC: Rf 0.68 (ethyl acetate);
$^1$H NMR (DMSO-$d_6$): δ 2.16 (s, 3H), 2.76-2.98 (m, 2H), 3.11-3.28 (m, 1H), 3.94-4.08 (m, 1H), 6.85 (s, 1H), 6.92-7.07 (m, 2H), 7.08-7.23 (m, 2H), 7.33-7.48 (m, 1H), 7.75 (d, J=8.42 Hz, 1H), 11.50 (s, 1H).

Example 34 (3)

7-acetyl-6-(3-fluorophenyl)-6,7,8,9-tetrahydro-5H-pyrido[4',3':4,5]pyrrolo[3,2-b]pyridine TLC: Rf 0.23 (ethyl acetate);
$^1$H NMR (DMSO-$d_6$): δ 2.18 (s, 3H), 2.89-3.00 (m, 2H), 3.17-3.47 (m, 1H), 4.00-4.12 (m, 1H), 6.94 (s, 1H), 6.97-7.04 (m, 1H), 7.06 (d, J=7.68 Hz, 1H), 7.12-7.24 (m, 1H), 7.28-7.49 (m, 2H), 8.06 (d, J=7.68 Hz, 1H), 8.45 (d, J=4.94 Hz, 1H), 11.93 (s, 1H).

Example 35

2-ethyl-1-(3-fluorophenyl)-1,2,3,9-tetrahydrospiro[β-carboline-4,1'-cyclopropane]

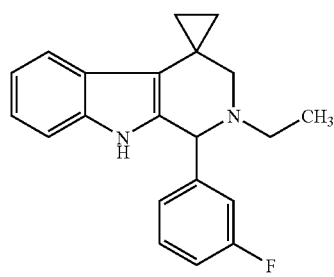

Under ice cooling, a borane-tetrahydrofuran complex (0.98M, 0.24 mL) and the compound (26 mg) prepared in Example 6 (21) were sequentially added to tetrahydrofuran (0.75 mL), followed by refluxing for one hour. Under ice cooling, 2N hydrochloric acid (0.5 mL) was added to the reaction mixture, followed by refluxing for 30 minutes. After air cooling, an aqueous 2N sodium hydroxide solution (0.5 mL) was added to the reaction mixture, followed by extraction with ethyl acetate. The organic layer was washed in turn with an aqueous saturated sodium hydrogen carbonate solution and saturated saline, dried over anhydrous sodium sulfate and then concentrated to obtain the titled compound having the following physical properties (25 mg).

TLC: Rf 0.28 (hexane:ethyl acetate=4:1);
$^1$H NMR (DMSO-$d_6$): δ 0.61-0.73 (m, 1H), 0.76-0.88 (m, 1H), 1.06 (t, J=7.04 Hz, 3H), 1.19-1.42 (m, 2H), 2.42 (d, J=12.99 Hz, 1H), 2.52-2.70 (m, 2H), 2.82 (d, J=12.99 Hz, 1H), 4.84 (s, 1H), 6.81-6.91 (m, 1H), 6.92-7.01 (m, 1H), 7.01-7.13 (m, 3H), 7.15-7.26 (m, 2H), 7.29-7.42 (m, 1H), 10.52 (s, 1H).

Example 36 (1) to Example 36 (7)

Using a corresponding amine derivative in place of [2-(1H-pyrrolo[2,3-b]pyridin-3-yl)ethyl]amine and a corresponding carboxylic acid derivative in place of 3-methoxybenzoic acid, the operation having the same purpose as that in Example 8 Example 9 Example 10 Example 12 was conducted to obtain the following compound.

Example 36 (1)

2-acetyl-1-(4-chloro-2-methoxyphenyl)-1,2,3,9-tetrahydrospiro[β-carboline-4,1'-cyclopropane]

TLC: Rf 0.58 (hexane:ethyl acetate=1:2);
$^1$H NMR (DMSO-$d_6$): δ 0.68-1.23 (m, 3H), 1.48-1.64 (m, 1H), 2.07 and 2.29 (s, 3H), 3.03-3.28 (m, 1H), 3.53-3.98 (m, 4H), 6.32-7.33 (m, 8H), 10.79-10.83 (m, 1H);
Description: solid.

Example 36 (2)

2-acetyl-1-(4-chloro-2-methoxyphenyl)-5-fluoro-1,2,3,9-tetrahydrospiro[β-carboline-4,1'-cyclopropane]

TLC: Rf 0.50 (hexane:ethyl acetate=1:1);
$^1$H NMR (DMSO-$d_6$): δ 0.66-1.12 (m, 3H), 1.29-1.41 (m, 1H), 2.07 and 2.30 (s, 3H), 3.07-3.28 (m, 1H), 3.58-3.80 (m, 1H), 3.81 and 3.95 (s, 3H), 6.36-7.25 (m, 7H), 11.22 and 11.24 (s, 1H);
Description: solid.

Example 36 (3)

2-acetyl-1-(4-chloro-2-methoxyphenyl)-5,6-difluoro-1,2,3,9-tetrahydrospiro[β-carboline-4,1'-cyclopropane]

TLC: Rf 0.31 (hexane:ethyl acetate=1:1);
$^1$H NMR (DMSO-$d_6$): δ 0.71-1.36 (m, 4H), 2.07 and 2.30 (s, 3H), 3.10 and 3.23 (d, J=14.8 Hz, 1H), 3.61 and 3.78 (d, J=14.8 Hz, 1H), 3.80 and 3.95 (m, 3H), 6.36-7.24 (m, 6H), 11.22-11.39 (m, 1H);
Description: solid.

Example 36 (4)

2-acetyl-1-(4-chloro-2-methoxyphenyl)-6-fluoro-1,2,3,9-tetrahydrospiro[β-carboline-4,1'-cyclopropane]

TLC: Rf 0.31 (hexane:ethyl acetate=1:2);
$^1$H NMR (DMSO-$d_6$): δ 0.60-1.20 (m, 3H), 1.48-1.58 (m, 1H), 2.07 and 2.29 (s, 3H), 3.04-3.28 (m, 1H), 3.55-3.97 (m, 4H), 6.37-7.30 (m, 7H), 10.93 (s, 1H);
Description: solid.

Example 36 (5)

2-acetyl-1-(4-chloro-2-methoxyphenyl)-5-methoxy-1,2,3,9-tetrahydrospiro[β-carboline-4,1'-cyclopropane]

TLC: Rf 0.23 (ethyl acetate:hexane=1:1);
$^1$H NMR (DMSO-$d_6$): δ 0.52-1.03 (m, 3H), 1.57-1.68 (m, 1H), 2.06 and 2.28 (d, 3H), 3.03-3.18 (m, 1H), 3.54-3.70 (m, 1H), 3.77-3.95 (m, 6H), 6.32 and 7.05 (s, 1H), 6.46 (d, J=7.9 Hz, 1H), 6.66-6.76 (m, 1H), 6.81-6.88 (m, 1H), 6.89-7.01 (m, 2H), 7.11 and 7.20 (d, J=2 Hz, 1H), 10.84-10.93 (m, 1H);
Description: solid.

Example 36 (6)

2-acetyl-5-chloro-1-(4-chloro-2-methoxyphenyl)-1,2,3,9-tetrahydrospiro[β-carboline-4,1'-cyclopropane]

TLC: Rf 0.39 (hexane:ethyl acetate=1:1);
$^1$H NMR (DMSO-$d_6$): δ 0.67-1.21 (m, 3H), 1.66-1.77 (m, 1H), 2.08 and 2.30 (s, 3H), 3.07-3.21 (m, 1H), 3.58-3.70 (m, 1H), 3.80 and 3.95 (s, 3H), 6.40 and 7.10 (s, 1H), 6.70-6.77 (m, 1H), 6.94-6.99 (m, 1H), 7.00-7.05 (m, 2H), 7.13 and 7.23 (d, J=1.8 Hz, 1H), 7.25-7.30 (m, 1 H), 11.41 and 11.42 (s, 1H);
Description: solid.

Example 36 (7)

2-acetyl-5-chloro-1-(2-methoxy-4-methylphenyl)-1,2,3,9-tetrahydrospiro[β-carboline-4,1'-cyclopropane]

TLC: Rf 0.32 (hexane:ethyl acetate=1:1);
$^1$H NMR (DMSO-$d_6$): δ 0.61-1.79 (m, 4H), 2.06-2.33 (m, 6H), 3.08-3.20 (m, 1H), 3.58-3.71 (m, 1H), 3.75 and 3.90 (s, 3H), 6.56-6.63 (m, 1H), 6.64-6.72 (m, 1H), 6.88 and 6.96 (s, 1H), 6.99-7.04 (m, 2H), 6.39 and 7.11 (s, 1H), 7.21-7.28 (m, 1H), 11.34-11.43 (m, 1H);
Description: solid.

Example 37 (1) to Example 37 (21)

Using 1H-indole-3-ylacetonitrile or alternatively a corresponding nitrile derivative and a corresponding aldehyde derivative in place of 1,3-benzodioxol-5-carboaldehyde, the operation having the same purpose as that in Example 1→Example 2→Example 3→Example 4 was conducted to obtain the following compound.

Example 37 (1)

2-acetyl-5-fluoro-1-(2-fluoro-6-methoxyphenyl)-1,2,3,9-tetrahydrospiro[β-carboline-4,1'-cyclopropane]

TLC: Rf 0.22 (hexane:ethyl acetate=1:1);
$^1$H NMR (DMSO-$d_6$): δ 0.72-1.52 (m, 4H), 2.06 and 2.17 (s, 3H), 3.31-3.52 (m, 1H), 3.73 and 3.88 (s, 3H), 3.96-4.11 (m, 1H), 6.53-7.12 (m, 6H), 7.27-7.47 (m, 1H), 11.03 and 11.07 (s, 1H);
Description: solid.

Example 37 (2)

2-acetyl-6-fluoro-1-(4-fluoro-2-methoxyphenyl)-1,2,3,9-tetrahydrospiro[β-carboline-4,1'-cyclopropane]

TLC: Rf 0.36 (hexane:ethyl acetate=1:2);
$^1$H NMR (DMSO-$d_6$): δ 0.67-1.59 (m, 4H), 2.06 and 2.29 (s, 3H), 3.09 and 3.23 (d, J=14.6 Hz, 1H), 3.60 and 3.78 (d, J=14.6 Hz, 1H), 3.79 and 3.93 (s, 3H), 6.60-6.79 (m, 2H), 6.80-7.08 (m, 4H), 6.38 and 7.11 (s, 1H), 7.16-7.31 (m, 1H), 10.93 and 10.94 (s, 1H);
Description: solid.

Example 37 (3)

2-acetyl-5-fluoro-1-(4-fluoro-2-methoxyphenyl)-1,2,3,9-tetrahydrospiro[β-carboline-4,1'-cyclopropane]

TLC: Rf 0.35 (hexane:ethyl acetate=1:2);
$^1$H NMR (DMSO-$d_6$): δ 0.66-0.99 (m, 2H), 1.01-1.14 (m, 1H), 1.28-1.42 (m, 1H), 2.07 and 2.30 (s, 3H), 3.08-3.26 (m, 1H), 3.59-3.79 (m, 1H), 3.79 and 3.94 (s, 3H), 6.37-7.13 (m, 7H), 11.23 and 11.25 (m, 1H);
Description: solid.

Example 37 (4)

2-acetyl-1-(5-fluoro-2-methoxyphenyl)-5-methoxy-1,2,3,9-tetrahydrospiro[β-carboline-4,1'-cyclopropane]

TLC: Rf 0.47 (hexane:ethyl acetate=1:2);
$^1$H NMR (DMSO-$d_6$): δ 0.53-0.72 (m, 1H), 0.76-1.09 (m, 2H), 1.47-1.84 (m, 1H), 2.07 and 2.29 (m, 3H), 3.02-3.23 (m, 1H), 3.53-3.97 (m, 7H), 6.23-7.41 (m, 7H), 10.87-10.94 (m, 1 H);
Description: solid.

Example 37 (5)

2-acetyl-1-(4-fluoro-2-methoxyphenyl)-5-methoxy-1,2,3,9-tetrahydrospiro[β-carboline-4,1'-cyclopropane]

TLC: Rf 0.36 (hexane:ethyl acetate=1:1);
$^1$H NMR (DMSO-$d_6$, 100° C.): δ 0.54-0.68 (m, 1H), 0.81-1.08 (m, 2H), 1.63-1.73 (m, 1H), 2.17 (s, 3H), 3.45 (s, 2H), 3.83 (s, 3H), 3.88 (s, 3H), 6.48-6.52 (dd, J=7.7, 1.0 Hz, 1H), 6.61-7.00 (m, 6H), 10.54 (s, 1H);
Description: solid.

Example 37 (6)

2-acetyl-1-(2,4-dimethoxyphenyl)-5-methoxy-1,2,3,9-tetrahydrospiro[β-carboline-4,1'-cyclopropane]

TLC: Rf 0.39 (hexane:ethyl acetate=1:2);
$^1$H NMR (DMSO-$d_6$) δ 0.45-0.68 (m, 1H), 0.76-1.06 (m, 2H), 1.49-1.72 (m, 1H), 2.05 and 2.28 (m, 3H), 3.05-3.15 (m, 1H), 3.57-3.69 (m, 1H), 3.69-3.94 (m, 9H), 6.19-7.13 (m, 7H), 10.86-10.90 (m, 1H);
Description: solid.

Example 37 (7)

2-acetyl-1-(2-fluoro-6-methoxyphenyl)-5-methoxy-1,2,3,9-tetrahydrospiro[β-carboline-4,1'-cyclopropane]

TLC: Rf 0.27 (hexane:ethyl acetate=1:1);
$^1$H NMR (DMSO-$d_6$): δ 0.56-0.74 (m, 1H), 0.75-1.05 (m, 2H), 1.68-1.87 (m, 1H), 2.05 and 2.14 (s, 3H), 3.16-3.59 (m, 1H), 3.67-4.17 (m, 7H), 6.43 (d, J=7.3 Hz, 1H), 6.47-7.05 (m, 5 H), 7.22-7.48 (m, 1H), 10.63 and 10.69 (s, 1H);
Description: solid.

Example 37 (8)

2-acetyl-1-(4-chloro-2-methoxyphenyl)-6,7-dimethoxy-1,2,3,9-tetrahydrospiro[β-carboline-4,1'-cyclopropane]

TLC: Rf 0.29 (hexane:ethyl acetate=1:2);
$^1$H NMR (DMSO-d$_6$): δ 0.64-1.24 (m, 3H), 1.46-1.66 (m, 1H), 2.06 and 2.27 (s, 3H), 3.04 and 3.21 (d, J=15 Hz, 1H), 3.56 and 3.75 (d, J=15 Hz, 1H), 3.71 (s, 3H), 3.72 (s, 3H), 3.81 and 3.94 (s, 3H), 6.63-6.65 (m, 1H), 6.66-6.73 (m, 1H), 6.80 and 6.81 (s, 1H), 6.87-6.99 (m, 1H), 6.31 and 7.03 (s, 1H), 7.10 and 7.19 (d, J=2.0 Hz, 1H), 10.45 (s, 1H);
Description: solid.

Example 37 (9)

2-acetyl-1-(2-methoxy-4-methylphenyl)-1,2,3,9-tetrahydrospiro[β-carboline-4,1'-cyclopropane]

TLC: Rf 0.32 (hexane:ethyl acetate=1:1);
$^1$H NMR (DMSO-d$_6$): δ 0.67-1.26 (m, 3H), 1.49-1.63 (m, 1H), 2.05-2.30 (m, 6H), 3.14 and 3.20 (d, J=15 Hz, 1H), 3.64 and 3.77 (d, J=15 Hz, 1H), 3.77 and 3.90 (s, 3H), 6.56-6.73 (m, 2 H), 6.83-7.06 (m, 3H), 6.37 and 7.12 (s, 1H), 7.17-7.29 (m, 2H), 10.78 (s, 1H);
Description: solid.

Example 37 (10)

2-acetyl-5-fluoro-1-(2-methoxy-4-methylphenyl)-1,2,3,9-tetrahydrospiro[β-carboline-4,1'-cyclopropane]

TLC: Rf 0.31 (hexane:ethyl acetate=1:1);
$^1$H NMR (DMSO-d$_6$, 100° C.): δ 0.66-0.81 (m, 1H), 0.86-1.07 (m, 2H), 1.36-1.47 (m, 1H), 2.07-2.33 (m, 6H), 3.27-3.75 (m, 2H), 3.86 (s, 3H), 6.58-7.06 (m, 6H), 7.09-7.14 (m, 1H), 10.87 (s, 1H);
Description: solid.

Example 37 (11)

2-acetyl-1-(4-chloro-2-methoxyphenyl)-6-methoxy-1,2,3,9-tetrahydrospiro[β-carboline-4,1'-cyclopropane]

TLC: Rf 0.27 (hexane:ethyl acetate=1:1);
$^1$H NMR (DMSO-d$_6$): δ 0.66-1.24 (m, 3H), 1.50-1.66 (m, 1H), 2.07 and 2.28 (s, 3H), 3.07 and 3.22 (d, J=14.6 Hz, 1H), 3.54-3.97 (m, 7H), 6.62-6.75 (m, 3H), 6.89-6.94 (m, 1H), 6.34 and 7.07 (s, 1H), 7.11 and 7.20 (d, J=2.0 Hz, 1H), 7.12-7.18 (m, 1H), 10.62 (s, 1H);
Description: solid.

Example 37 (12)

2-acetyl-1-(4-fluoro-2-methoxyphenyl)-6-methoxy-1,2,3,9-tetrahydrospiro[β-carboline-4,1'-cyclopropane]

TLC: Rf 0.30 (hexane:ethyl acetate=1:1);
$^1$H NMR (DMSO-d$_6$): δ 0.66-1.24 (m, 3H), 1.49-1.66 (m, 1H), 2.06 and 2.29 (s, 3H), 3.08 and 3.21 (d, J=14.6 Hz, 1H), 3.55-3.94 (m, 7H), 6.60-6.77 (m, 4H), 6.91-7.06 (m, 1H), 6.34 and 7.08 (s, 1H), 7.12-7.18 (m, 1H), 10.63 (s, 1H);
Description: solid.

Example 37 (13)

2-acetyl-6-methoxy-1-(2-methoxy-4-methylphenyl)-1,2,3,9-tetrahydrospiro[β-carboline-4,1'-cyclopropane]

TLC: Rf 0.40 (hexane:ethyl acetate=1:1);
$^1$H NMR (DMSO-d$_6$): δ 0.64-1.25 (m, 3H), 1.50-1.64 (m, 1H), 2.05-2.30 (m, 6H), 3.12 and 3.18 (d, J=13.2 Hz, 1H), 3.59-3.90 (m, 7H), 6.57-6.70 (m, 4H), 6.85 and 6.93 (s, 1H), 6.33 and 7.08 (s, 1H), 7.11-7.16 (m, 1H), 10.58-10.61 (m, 1H);
Description: solid.

Example 37 (14)

2-acetyl-1-(2-fluoro-6-methoxyphenyl)-6-methoxy-1,2,3,9-tetrahydrospiro[β-carboline-4,1'-cyclopropane]

TLC: Rf 0.27 (hexane:ethyl acetate=1:1);
$^1$H NMR (DMSO-d$_6$): δ 0.74-1.11 (m, 3H), 1.57-1.75 (m, 1H), 2.05 and 2.12 (s, 3H), 3.29 and 3.52 (d, J=13.8 Hz, 1H), 3.69-4.13 (m, 7H), 6.58-6.69 (m, 2H), 6.69-6.82 (m, 1H), 6.87 and 6.98 (d, J=8.1 Hz, 1H), 6.52 and 6.94 (s, 1H), 7.10 (d, J=8.6 Hz, 1H), 7.25-7.45 (m, 1H), 10.38 and 10.43 (s, 1H);
Description: solid.

Example 37 (15)

2-acetyl-6,7-dimethoxy-1-(2-methoxy-4-methylphenyl)-1,2,3,9-tetrahydrospiro[β-carboline-4,1'-cyclopropane]

TLC: Rf 0.32 (hexane:ethyl acetate=1:2);
$^1$H NMR (DMSO-d$_6$): δ 0.62-1.30 (m, 3H), 1.47-1.61 (m, 1H), 2.04-2.30 (m, 6H), 3.09 and 3.17 (d, J=14.8 Hz, 1H), 3.57-3.90 (m, 10H), 6.56-6.69 (m, 3H), 6.80 (s, 1H), 6.84 and 6.92 (s, 1H), 6.30 and 7.04 (s, 1H) 10.42 and 10.44 (s, 1H);
Description: solid.

Example 37 (16)

2-acetyl-1-(4-chloro-2-methoxyphenyl)-5-methyl-1,2,3,9-tetrahydrospiro[β-carboline-4,1'-cyclopropane]

TLC: Rf 0.33 (hexane:ethyl acetate=1:1);
$^1$H NMR (DMSO-d$_6$): δ 0.68-1.24 (m, 3H), 1.33-1.49 (m, 1H), 2.07 and 2.29 (s, 3H), 2.42 (s, 3 H), 3.07-3.21 (m, 1H), 3.65 (d, J=13.7 Hz, 1H), 3.81 and 3.95 (s, 3H), 6.37 and 7.05 (s, 1H), 6.69-6.77 (m, 2H), 6.88-6.98 (m, 2H), 7.08-7.23 (m, 2H), 10.95 and 10.96 (s, 1H);
Description: solid.

Example 37 (17)

2-acetyl-1-(2-methoxy-4-methylphenyl)-5-methyl-1,2,3,9-tetrahydrospiro[β-carboline-4,1'-cyclopropane]

TLC: Rf 0.32 (hexane:ethyl acetate=1:1);
$^1$H NMR (DMSO-d$_6$): δ 0.68-1.20 (m, 3H), 1.32-1.48 (m, 1H), 2.04-2.44 (m, 9H), 3.11 and 3.18 (d, J=13.4 Hz, 1H), 3.62 and 3.69 (d, J=13.4 Hz, 1H), 3.76 and 3.90 (s, 3H), 6.35-7.11 (m, 7H), 10.92 and 10.94 (s, 1H);

Description: solid.

Example 37 (18)

2-acetyl-1-(2,3-dihydro-1-benzofuran-7-yl)-6-methoxy-1,2,3,9-tetrahydrospiro[β-carboline-4,1'-cyclopropane]

TLC: Rf 0.25 (hexane:ethyl acetate=1:1);

$^1$H NMR (DMSO-d$_6$): δ 0.67-1.25 (m, 3H), 1.53-1.66 (m, 1H), 2.07 and 2.32 (s, 3H), 3.12-3.29 (m, 3H), 3.71 (s, 3H), 3.75 and 3.80 (d, J=13.6 Hz, 1H), 4.53 (t, J=8.6 Hz, 1H), 4.60-4.70 (m, 1H), 6.57-6.78 (m, 4H), 6.24 and 6.94 (s, 1H), 7.13-7.22 (m, 2H), 10.63 (s, 1H);

Description: solid.

Example 37 (19)

2-acetyl-1-(4-chloro-2-methoxyphenyl)-6-methoxy-5-methyl-1,2,3,9-tetrahydrospiro[β-carboline-4,1'-cyclopropane]

TLC: Rf 0.31 (hexane:ethyl acetate=1:1);

$^1$H NMR (DMSO-d$_6$): δ 0.68-1.22 (m, 3H), 1.32-1.49 (m, 1H), 2.07 and 2.23 (s, 3H), 2.23 and 2.28 (s, 3H), 3.05-3.19 (m, 1H), 3.57-3.68 (m, 1H), 3.71 (s, 3H), 3.80 and 3.94 (s, 3H), 6.34 and 7.00 (s, 1H), 6.67-6.76 (m, 1H), 6.80-6.86 (m, 1H), 6.89-6.97 (m, 1H), 7.02-7.08 (m, 1 H), 7.11 and 7.20 (d, J=1.8 Hz, 1H), 10.72 and 10.75 (s, 1H);

Description: solid.

Example 37 (20)

2-acetyl-5-fluoro-1-(2-methoxyphenyl)-1,2,3,9-tetrahydrospiro[β-carboline-4,1'-cyclopropane]

TLC: Rf 0.29 (hexane:ethyl acetate=1:1);

$^1$H NMR (DMSO-d$_6$): δ 0.64-1.14 (m, 3H), 1.29-1.41 (m, 1H), 2.07 and 2.32 (s, 3H), 3.11-3.26 (m, 1H), 3.62-3.78 (m, 1H), 3.78 and 3.92 (s, 3H), 6.42-7.39 (m, 8H), 11.24 (s, 1H);

Description: solid.

Example 37 (21)

2-acetyl-1-(4-chloro-2-methoxyphenyl)-5,6-dimethoxy-1,2,3,9-tetrahydrospiro[β-carboline-4,1'-cyclopropane]

TLC: Rf 0.27 (hexane:ethyl acetate=1:1);

$^1$H NMR (DMSO-d$_6$): δ 0.53-0.72 (m, 1H), 0.80-0.91 (m, 1H), 0.92-1.04 (m, 1H), 1.56-1.73 (m, 1H), 2.06 and 2.28 (s, 3H), 3.01-3.20 (m, 1H), 3.55-3.70 (m, 1H), 3.75-3.94 (m, 9H), 6.31 and 7.02 (s, 1H), 6.68-6.76 (m, 1H), 6.82-6.98 (m, 3H), 7.11 and 7.20 (d, J=2.0 Hz, 1H), 10.73 (s, 1H);

Description: solid.

Example 38

(1S)-2-acetyl-1-(4-chloro-2-methoxyphenyl)-5-fluoro-1,2,3,9-tetrahydrospiro[β-carboline-4,1'-cyclopropane]

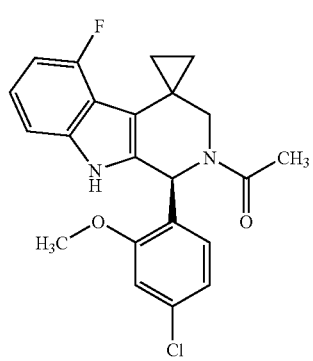

The compound prepared in Example 36 (2) was optically resolved using HPLC (column used: CHIRALCEL OJ manufactured by Daicel Chemical Industries, Ltd.; development solvent: hexane:ethanol=85:15) to obtain the titled compound having the following physical properties.

TLC: Rf 0.39 (ethyl acetate:hexane=2:1);

$^1$H NMR (CDCl$_3$): δ 0.62-1.43 (m, 3H), 1.59-1.75 (m, 1H), 2.21 (s, 3H), 3.07-3.57 (m, 1H), 3.84-4.26 (m, 4H), 6.29-7.18 (m, 7H), 8.34 and 8.67 (s, 1H);

[α]$_D$=+200.0 (CHCl$_3$, c=0.17);

Description: solid.

Example 38 (1)

(−)-2-acetyl-1-(4-chloro-2-methoxyphenyl)-5,6-difluoro-1,2,3,9-tetrahydrospiro[β-carboline-4,1'-cyclopropane]

Using the compound prepared in Example 36 (3) in place of the compound prepared in Example 36 (2), the same operation as in Example 38 was conducted to obtain the titled compound having the following physical properties.

TLC: Rf 0.38 (hexane:ethyl acetate=2:1);

$^1$H NMR (CDCl$_3$): δ 0.64-1.40 (m, 3H), 1.49-1.77 (m, 1H), 2.11-2.34 (m, 3H), 3.05-3.57 (m, 1H), 3.73-4.36 (m, 4H), 6.23-7.16 (m, 6H), 8.33 and 8.94 (s, 1H);

[α]$_D$=−148.7 (CHCl$_3$, c=0.18);

Description: solid.

Example 38 (2)

(+)-2-acetyl-1-(4-chloro-2-methoxyphenyl)-5,6-difluoro-1,2,3,9-tetrahydrospiro[β-carboline-4,1'-cyclopropane]

Using the compound prepared in Example 36 (3) in place of the compound prepared in Example 36 (2), the same operation as in Example 38 was conducted to obtain the titled compound having the following physical properties.

TLC: Rf 0.38 (hexane:ethyl acetate=1:2);

$^1$H NMR (CDCl$_3$): δ 0.57-1.41 (m, 3H), 1.53-1.72 (m, 1H), 2.04-2.42 (m, 3H), 3.02-3.57 (m, 1H), 3.68-4.41 (m, 4H), 6.27-7.23 (m, 6H), 8.33 and 8.93 (s, 1H);

[α]$_D$=+188.9 (CHCl$_3$, c=0.16);

Description: solid.

Example 38 (3)

(+)-2-acetyl-1-(4-chloro-2-methoxyphenyl)-5-methoxy-1,2,3,9-tetrahydrospiro[β-carboline-4,1'-cyclopropane]

Using the compound prepared in Example 36 (5) in place of the compound prepared in Example 36 (2), the same operation as in Example 38 was conducted to obtain the titled compound having the following physical properties.
TLC: Rf 0.44 (hexane:ethyl acetate=2:3);
$^1$H NMR (CDCl$_3$): δ 0.52-0.77 (m, 1H), 0.80-1.26 (m, 2H), 1.76-1.99 (m, 1H), 2.09-2.30 (m, 3H), 2.98-3.56 (m, 1H), 3.76-4.22 (m, 7H), 6.22-7.17 (m, 7H), 8.16 and 8.36 (s, 1H);
$[\alpha]_D$=+238.1 (CHCl$_3$, c=0.15);
Description: solid.

Example 38 (4)

(+)-2-acetyl-1-(2-fluoro-6-methoxyphenyl)-5-methoxy-1,2,3,9-tetrahydrospiro[β-carboline-4,1'-cyclopropane]

Using the compound prepared in Example 37 (7) in place of the compound prepared in Example 36 (2), the same operation as in Example 38 was conducted to obtain the titled compound having the following physical properties.
TLC: Rf 0.35 (hexane:ethyl acetate=2:3);
$^1$H NMR (CDCl$_3$): δ 0.57-2.23 (m, 7H), 3.04-4.03 (m, 7H), 4.08-4.47 (m, 1H), 6.40-7.08 (m, 6H), 7.14-7.38 (m, 1H), 7.79 and 8.04 (s, 1H);
$[\alpha]_D$=+154.9 (CHCl$_3$, c=0.15);
Description: solid.

Example 38 (5)

(+)-2-acetyl-5-fluoro-1-(2-fluoro-6-methoxyphenyl)-1,2,3,9-tetrahydrospiro[β-carboline-4,1'-cyclopropane]

Using the compound prepared in Example 37 (1) in place of the compound prepared in Example 36 (2), the same operation as in Example 38 was conducted to obtain the titled compound having the following physical properties.
TLC: Rf 0.32 (hexane:ethyl acetate=2:3);
$^1$H NMR (CDCl$_3$): δ 0.69-1.21 (m, 3H), 1.66-1.92 (m, 1H), 2.04-2.24 (m, 3H), 3.10-3.88 (m, 1H), 3.94 (s, 3H), 4.14-4.52 (m, 1H), 6.49-7.11 (m, 6H), 7.14-7.47 (m, 1H), 7.93 and 8.17 (s, 1H);
$[\alpha]_D$=+180.8 (CHCl$_3$, c=0.17);
Description: solid.

Example 38 (6)

(+)-2-acetyl-1-(4-chloro-2-methoxyphenyl)-6,7-dimethoxy-1,2,3,9-tetrahydrospiro[β-carboline-4,1'-cyclopropane]

Using the compound prepared in Example 37 (8) in place of the compound prepared in Example 36 (2), the same operation as in Example 38 was conducted to obtain the titled compound having the following physical properties.
TLC: Rf 0.37 (hexane:ethyl acetate=1:2);
$^1$H NMR (CDCl$_3$): δ 0.68-1.81 (m, 4H), 2.12-2.24 (m, 3H), 3.08-3.54 (m, 1H), 3.75-4.28 (m, 10H), 6.25-7.17 (m, 6H), 7.97 and 8.20 (s, 1H);
$[\alpha]_D$=+146.5 (CHCl$_3$, c=0.16);
Description: solid.

Example 39 (1) to Example 39 (10)

Using a corresponding amine derivative in place of [2-(1H-pyrrolo[2,3-b]pyridin-3-yl)ethyl]amine and a corresponding carboxylic acid derivative in place of 3-methoxybenzoic acid, the operation having the same purpose as that in Example 8→Example 9→Example 10→Example 12 was conducted to obtain the following compound.

Example 39 (1)

2-acetyl-5-chloro-1-(4-fluoro-2-methoxyphenyl)-1,2,3,9-tetrahydrospiro[β-carboline-4,1'-cyclopropane]

TLC: Rf 0.41 (hexane:ethyl acetate=1:1);
$^1$H NMR (DMSO-d$_6$): δ 0.63-1.24 (m, 3H), 1.63-1.79 (m, 1H), 2.08 and 2.30 (s, 3H), 3.09-3.19 (m, 1H), 3.59-3.69 (m, 1H), 3.79 and 3.93 (s, 3H), 6.39 and 7.10 (s, 1H), 6.62-6.72 (m, 1H), 6.72-6.78 (m, 1H), 6.93-7.06 (m, 3H), 7.19-7.34 (m, 1H), 11.40-11.46 (m, 1H);
Description: solid.

Example 39 (2)

2-acetyl-5,6-difluoro-1-(4-fluoro-2-methoxyphenyl)-1,2,3,9-tetrahydrospiro[β-carboline-4,1'-cyclopropane]

TLC: Rf 0.70 (hexane:ethyl acetate=1:1);
$^1$H NMR (DMSO-d$_6$): δ 0.68-1.38 (m, 4H), 2.00-2.38 (m, 3H), 3.03-3.39 (m, 1H), 3.56-3.83 (m, 1H), 3.73-3.98 (m, 3H), 6.39 (s, 0.5H), 6.61-6.81 (m, 2H), 6.91-7.14 (m, 3.5H), 11.33 (s, 1H);
Description: solid.

Example 39 (3)

2-acetyl-5,6-difluoro-1-(2-methoxy-4-methylphenyl)-1,2,3,9-tetrahydrospiro[β-carboline-4,1'-cyclopropane]

TLC: Rf 0.32 (hexane:ethyl acetate=1:1);
$^1$H NMR (DMSO-d$_6$): δ 0.66-1.38 (m, 4H), 2.01-2.35 (m, 6H), 3.08-3.28 (m, 1H), 3.60-3.82 (m, 1H), 3.72-3.95 (m, 3H), 6.56-6.64 (m, 1H), 6.64-6.73 (m, 1H), 6.87 and 6.96 (s, 1H), 7.00-7.10 (m, 2H), 6.38 and 7.12 (s, 1H), 11.29 (s, 1H);
Description: solid.

Example 39 (4)

2-acetyl-5-chloro-1-(2-fluoro-6-methoxyphenyl)-1,2,3,9-tetrahydrospiro[β-carboline-4,1'-cyclopropane]

TLC: Rf 0.50 (hexane:ethyl acetate=1:1);
$^1$H NMR (DMSO-d$_6$): δ 0.67-1.21 (m, 3H), 1.69-1.88 (m, 1H), 2.07 and 2.18 (s, 3H), 3.20-3.54 (m, 1H), 3.72 and 3.88 (s, 3H), 3.86 and 4.09 (d, J=14 Hz, 0.5H), 6.53 (s, 1H), 6.69-6.86 (m, 1H), 6.86-7.07 (m, 3H), 7.20-7.22 (m, 2H), 7.29-7.39 (m, 1H), 11.16-11.26 (m, 1H);
Description: solid.

Example 39 (5)

2-acetyl-1-(4-chloro-2-isopropoxyphenyl)-1,2,3,9-tetrahydrospiro[β-carboline-4,1'-cyclopropane]

TLC: Rf 0.33 (hexane:ethyl acetate=2:1);
$^1$H NMR (DMSO-d$_6$, 100° C.): δ 0.72-0.87 (m, 1H), 0.93-1.07 (m, 1H), 1.08-1.25 (m, 4H), 1.36 (d, J=5.9 Hz, 3H), 1.51-1.67 (m, 1H), 2.16 (s, 3H), 3.52 (b, 2H), 4.61-4.90 (m, 1H), 6.72-6.97 (m, 3H), 6.97-7.07 (m, 1H), 7.10 (s, 1H), 7.23 (d, J=7.9 Hz, 1H), 7.28 (d, J=8.1 Hz, 1H), 10.48 (s, 1H);
Description: solid.

Example 39 (6)

2-acetyl-1-[4-chloro-2-(cyclopentyloxy)phenyl]-1,2,3,9-tetrahydrospiro[β-carboline-4,1'-cyclopropane]

TLC: Rf 0.47 (hexane:ethyl acetate=2:1);
$^1$H NMR (DMSO-d$_6$, 100° C.): δ 0.73-0.86 (m, 1H), 0.96-1.08 (m, 1H), 1.11-1.26 (m, 1H), 1.44-2.06 (m, 9H), 2.15 (s, 3H), 3.59 (b, 2H), 4.94 (s, 1H), 6.81-6.97 (m, 3H), 6.98-7.11 (m, 2H), 7.24 (d, J=7.68 Hz, 1H), 7.28 (d, J=8.05 Hz, 1H), 10.49 (s, 1H);
Description: solid.

Example 39 (7)

4-(2-acetyl-1,2,3,9-tetrahydrospiro[β-carboline-4,1'-cyclopropane]-1-yl)-3-methoxybenzonitrile TLC: Rf 0.17 (hexane:ethyl acetate=1:1);
$^1$H NMR (DMSO-d$_6$): δ 0.71-0.98 (m, 1H), 1.00-1.23 (m, 2H), 1.51-1.64 (m, 1H), 2.08 and 2.30 (s, 3H), 3.00-3.34 (m, 1H), 3.53-3.84 (m, 1H), 3.87 and 3.94 (s, 3H), 6.45 and 7.15 (s, 1H), 6.83-6.96 (m, 2H), 6.99-7.08 (m, 1H), 7.20-7.30 (m, 2H), 7.32-7.40 (m, 1H), 7.54 and 7.63 (d, J=1.5 Hz, 1H), 10.81 (s, 1H);
Description: solid.

Example 39 (8)

2-acetyl-1-(4-chloro-2-methoxyphenyl)-5,7-difluoro-1,2,3,9-tetrahydrospiro[β-carboline-4,1'-cyclopropane]

TLC: Rf 0.28 (hexane:ethyl acetate=1:1);
$^1$H NMR (DMSO-d$_6$): δ 0.66-1.15 (m, 3H), 1.25-1.38 (m, 1H), 2.07 and 2.29 (s, 3H), 3.08 and 3.25 (d, J=14 Hz, 1H), 3.59 and 3.76 (d, J=14 Hz, 1H), 3.80 and 3.94 (s, 3H), 6.38 and 7.08 (s, 1H), 6.70-6.82 (m, 2H), 6.91-7.00 (m, 2H), 7.13 and 7.22 (d, J=2.0, 1H), 11.34 and 11.37 (s, 1H);
Description: solid.

Example 39 (9)

2-acetyl-1-(4-chloro-2-methoxyphenyl)-8-fluoro-1,2,3,9-tetrahydrospiro[β-carboline-4,1'-cyclopropane]

TLC: Rf 0.31 (hexane:ethyl acetate=1:1);
$^1$H NMR (DMSO-d$_6$): δ 0.70-1.23 (m, 3H), 1.47-1.60 (m, 1H), 2.07 and 2.31 (s, 3H), 3.05 and 3.23 (d, J=15 Hz, 1H), 3.53-3.77 (d, J=15 Hz, 1H), 3.80 and 3.95 (s, 3H), 6.38 and 7.18 (s, 1H), 6.63-6.69 (m, 1H), 6.82-7.08 (m, 4H), 7.12 and 7.22 (d, J=2.0 Hz, 1H), 11.33 and 11.35 (s, 1H);
Description: solid.

Example 39 (10)

4-(2-acetyl-5-fluoro-1,2,3,9-tetrahydrospiro[β-carboline-4,1'-cyclopropane]-1-yl)-3-methoxybenzonitrile TLC: Rf 0.42 (hexane:ethyl acetate=1:2);
$^1$H NMR (DMSO-d$_6$): δ 0.66-1.13 (m, 3H), 1.31-1.41 (m, 1H), 2.08 and 2.31 (s, 3H), 3.03-3.34 (m, 1H), 3.57 and 3.78 (d, J=14.1 Hz, 1H), 3.86 and 3.99 (s, 3H), 6.46 (s, 0.5H), 6.66-6.78 (m, 1H), 6.86-6.95 (m, 1H), 6.97-7.08 (m, 1H), 7.09-7.17 (m, 1.5H), 7.32-7.40 (m, 1 H), 7.55 and 7.64 (d, J=1.5 Hz, 1H), 11.24 (s, 1H);
Description: solid.

Example 40 (1) to Example 40 (9)

Using 1H-indole-3-ylacetonitrile or alternatively a corresponding nitrile derivative thereof and a corresponding aldehyde derivative in place of 1,3-benzodioxol-5-carboaldehyde, the operation having the same purpose as that in Example 1→Example 2→Example 3→Example 4 was conducted to obtain the following compound.

Example 40 (1)

2-acetyl-5,6-dimethoxy-1-(2-methoxy-4-methylphenyl)-1,2,3,9-tetrahydrospiro[β-carboline-4,1'-cyclopropane]

TLC: Rf 0.20 (hexane:ethyl acetate=1:1);
$^1$H NMR (DMSO-d$_6$): δ 0.52-0.70 (m, 1H), 0.79-0.90 (m, 1H), 0.91-1.02 (m, 1H), 1.54-1.74 (m, 1H), 2.05 and 2.27 (s, 3H), 2.28 (s, 3H), 3.11 (m, 1H), 3.59-3.70 (m, 1H), 3.76 (s, 3H), 3.83 (s, 3H), 3.89 (s, 3H), 6.31 and 7.04 (s, 1H), 6.55-6.73 (m, 2H), 6.80-6.98 (m, 3H), 10.73 (s, 1H);
Description: solid.

Example 40 (2)

2-acetyl-5-methoxy-1-(2-methoxyphenyl)-1,2,3,9-tetrahydrospiro[β-carboline-4,1'-cyclopropane]

TLC: Rf 0.51 (hexane:ethyl acetate=1:1);
$^1$H NMR (DMSO-d$_6$): δ 0.48-1.16 (m, 3H), 1.57-1.69 (m, 1H), 2.06 and 2.30 (s, 3H), 3.06-3.16 (m, 1H), 3.58-3.70 (m, 1H), 3.79 (s, 3H), 3.77 and 3.91 (s, 3H), 6.37 (s, 0.5H), 6.45 (d, J=8.1 Hz, 1H), 6.69-6.77 (m, 1H), 6.79-6.89 (m, 2H), 6.89-6.98 (m, 1H), 7.02 (d, J=8.06 Hz, 0.5H), 7.07-7.14 (m, 1H), 7.23-7.36 (m, 1H), 10.87 (s, 1H);
Description: solid.

Example 40 (3)

4-(2-acetyl-5-methoxy-1,2,3,9-tetrahydrospiro[β-carboline-4,1'-cyclopropane]-1-yl)benzonitrile TLC: Rf 0.38 (hexane:ethyl acetate=2:1);
$^1$H NMR (DMSO-d$_6$): δ 0.55-1.10 (m, 3H), 1.63-1.76 (m, 1H), 2.11 (s, 3H), 3.20 (d, J=14.7 Hz, 1H), 3.46 (d, J=14.7 Hz, 1H), 3.80 (s, 3H), 6.47 (d, J=7.7 Hz, 1H), 6.86 (s, 1H), 6.87-6.91 (m, 1H), 6.98 (t, J=7.88 Hz, 1H), 7.38 (d, J=8.43 Hz, 2H), 7.81 (d, J=8.43 Hz, 2H), 11.12 (s, 1H);
Description: solid.

Example 40 (4)

2-acetyl-1-(2,3-dihydro-1-benzofuran-7-yl)-5-methoxy-1,2,3,9-tetrahydrospiro[β-carboline-4,1'-cyclopropane]

TLC: Rf 0.45 (hexane:ethyl acetate=1:1);
$^1$H NMR (DMSO-$d_6$): δ 0.52-1.06 (m, 3H), 1.58-1.73 (m, 1H), 2.06 and 2.32 (s, 3H), 3.11-3.29 (m, 3H), 3.66-3.77 (m, 1H), 3.79 (s, 3H), 4.47-4.71 (m, 2H), 6.22 and 6.91 (s, 1H), 6.44 (d, J=7.70 Hz, 1H), 6.56-6.68 (m, 1H), 6.68-6.78 (m, 1H), 6.82-6.87 (m, 1H), 6.92-6.98 (m, 1H), 7.13-7.23 (m, 1H), 10.87 (s, 1H);
Description: solid.

Example 40 (5)

2-acetyl-5-methoxy-1-(2-methoxy-4-methylphenyl)-1,2,3,9-tetrahydrospiro[β-carboline-4,1'-cyclopropane]

TLC: Rf 0.46 (hexane:ethyl acetate=1:1);
$^1$H NMR (DMSO-$d_6$): δ 0.46-1.28 (m, 3H), 1.51-1.72 (m, 1H), 2.05 and 2.27 (s, 3H), 2.29 (s, 3H), 3.05-3.15 (m, 1H), 3.58-3.69 (m, 1H), 3.79 (s, 3H), 3.75 and 3.89 (s, 3H), 6.44 (d, J=7.70 Hz, 1H), 6.56-6.70 (m, 2H), 6.80-6.98 (m, 3H), 6.31 and 7.06 (s, 1H), 10.84 (s, 1H);
Description: solid.

Example 40 (6)

2-acetyl-1-(4-chloro-2-methoxyphenyl)-6,8-dimethoxy-1,2,3,9-tetrahydrospiro[β-carboline-4,1'-cyclopropane]

TLC: Rf 0.46 (hexane:ethyl acetate=1:3);
$^1$H NMR (DMSO-$d_6$): δ 0.60-1.32 (m, 3H), 1.44-1.63 (m, 1H), 2.05 and 2.28 (s, 3H), 2.98 and 3.16 (d, J=14.5 Hz, 1H), 3.45-3.96 (m, 10H), 6.20-6.25 (m, 1H), 6.26-6.34 (m, 1.5H), 6.61 (d, J=8.1 Hz, 1H), 6.87-6.98 (m, 1H), 7.07-7.21 (m, 1.5H), 10.72 and 10.75 (s, 1H);
Description: solid.

Example 40 (7)

2-acetyl-6-chloro-1-(4-chloro-2-methoxyphenyl)-1,2,3,9-tetrahydrospiro[β-carboline-4,1'-cyclopropane]

TLC: Rf 0.23 (hexane:ethyl acetate=1:1);
$^1$H NMR (DMSO-$d_6$): δ 0.71-1.22 (m, 3H), 1.45-1.60 (m, 1H), 2.07 and 2.29 (s, 3H), 3.08 and 3.25 (d, J=14.8 Hz, 1H), 3.59 and 3.79 (d, J=14.8 Hz, 1H), 3.81 and 3.94 (s, 3H), 6.39 and 7.09 (s, 1H), 6.63-6.75 (m, 1H), 6.89-6.99 (m, 1H), 6.99-7.06 (m, 1H), 7.10-7.22 (m, 2H), 7.23-7.32 (m, 1H), 11.05 (s, 1H);
Description: solid.

Example 40 (8)

2-acetyl-1-(4-chloro-2-methoxyphenyl)-5-fluoro-8-methoxy-1,2,3,9-tetrahydrospiro[β-carboline-4,1'-cyclopropane]

TLC: Rf 0.41 (hexane:ethyl acetate=1:2);
$^1$H NMR (DMSO-$d_6$): δ 0.59-1.11 (m, 3H), 1.25-1.41 (m, 1H), 2.00-2.38 (m, 3H), 2.93-3.25 (m, 1H), 3.43-3.76 (m, 1H), 3.75-3.97 (m, 6H), 6.25-7.35 (m, 6H), 11.17-11.49 (m, 1H);
Description: solid.

Example 40 (9)

2-acetyl-5-fluoro-1-(4-fluoro-2-methoxyphenyl)-8-methoxy-1,2,3,9-tetrahydrospiro[β-carboline-4,1'-cyclopropane]

TLC: Rf 0.36 (hexane:ethyl acetate=1:2);
$^1$H NMR (DMSO-$d_6$): δ 0.56-1.13 (m, 3H), 1.24-1.40 (m, 1H), 2.01-2.36 (m, 3H), 2.98-3.25 (m, 1H), 3.46-3.75 (m, 1H), 3.74-3.97 (m, 6H), 6.29-7.22 (m, 6H), 11.19-11.49 (m, 1H);
Description: solid.

Example 41 (1)

(+)-2-acetyl-1-(2-fluoro-6-methoxyphenyl)-6-methoxy-1,2,3,9-tetrahydrospiro[β-carboline-4,1'-cyclopropane]

Using the compound prepared in Example 37 (14) in place of the compound prepared in Example 36 (2), the same operation as in Example 38 was conducted to obtain the titled compound having the following physical properties.
TLC: Rf 0.35 (hexane:ethyl acetate=2:3);
$^1$H NMR (CDCl$^3$): δ 0.74-1.23 (m, 3H), 1.70-1.92 (m, 1H), 2.06-2.26 (m, 3H), 3.09-4.02 (m, 7H), 4.12-4.49 (m, 1H), 6.53-7.08 (m, 5H), 7.09-7.16 (m, 1H), 7.16-7.37 (m, 1H), 7.61-8.00 (m, 1H);
[α]$_D$=+180.0 (CHCl$_3$, c=0.16);
Description: solid.

Example 41 (2)

(+)-2-acetyl-1-(2-methoxy-4-methylphenyl)-5-methyl-1,2,3,9-tetrahydrospiro[β-carboline-4,1'-cyclopropane]

Using the compound prepared in Example 37 (17) in place of the compound prepared in Example 36 (2), the same operation as in Example 38 was conducted to obtain the titled compound having the following physical properties.
TLC: Rf 0.40 (hexane:ethyl acetate=1:1);
$^1$H NMR (DMSO-$d_6$): δ 0.67-1.48 (m, 4H), 2.02-2.46 (m, 9H), 3.03-3.25 (m, 1H), 3.57-3.73 (m, 1H), 3.73-3.92 (m, 3H), 6.36 (s, 0.5H), 6.57-6.72 (m, 2H), 6.74 (d, J=7.1 Hz, 1H), 6.84-6.98 (m, 2H), 7.04-7.14 (m, 1.5H), 10.83-11.03 (m, 1H);
[α]$_D$=+177.4 (CHCl$_3$, c=0.14);
Description: solid.

Example 41 (3)

(+)-2-acetyl-1-(4-chloro-2-methoxyphenyl)-6-methoxy-5-methyl-1,2,3,9-tetrahydrospiro[β-carboline-4,1'-cyclopropane]

Using the compound prepared in Example 37 (19) in place of the compound prepared in Example 36 (2), the same operation as in Example 38 was conducted to obtain the titled compound having the following physical properties.
TLC: Rf 0.20 (hexane:ethyl acetate=1:1);
$^1$H NMR (DMSO-$d_6$): δ 0.68-1.16 (m, 3H), 1.32-1.47 (m, 1H), 2.02-2.30 (m, 6H), 3.06-3.19 (m, 1H), 3.58-3.68 (m, 1H), 3.72 (s, 3H), 3.80 and 3.94 (s, 3H), 6.34 and 7.00 (s, 1H), 6.69 and 6.74 (d, J=8.2 Hz, 1H), 6.83 and 6.85 (d, J=8.8 Hz, 1H), 6.89-6.99 (m, 1H), 7.05 and 7.06 (d, J=8.8 Hz, 1H), 7.12 and 7.20 (d, J=2.0 Hz, 1H), 10.74 and 10.77 (s, 1H);
[α]$_D$=+151.1 (CHCl$_3$, c=0.19);
Description: solid.

Example 41 (4)

(+)-2-acetyl-5-fluoro-1-(4-fluoro-2-methoxyphenyl)-1,2,3,9-tetrahydrospiro[β-carboline-4,1'-cyclopropane]

Using the compound prepared in Example 37 (3) in place of the compound prepared in Example 36 (2), the same operation as in Example 38 was conducted to obtain the titled compound having the following physical properties.
TLC: Rf 0.26 (hexane:ethyl acetate=1:1);
$^1$H NMR (DMSO-d$_6$): δ 0.67-1.15 (m, 3H), 1.30-1.41 (m, 1H), 2.07 and 2.30 (s, 3H), 3.10 and 3.24 (d, J=14.5 Hz, 1H), 3.56-3.95 (m, 4H), 6.36-7.15 (m, 7H), 11.25 and 11.27 (s, 1H);
[α]$_D$=+159.7 (CHCl$_3$, c=0.12);
Description: solid.

Example 41 (5)

(+)-2-acetyl-5,6-difluoro-1-(2-methoxy-4-methylphenyl)-1,2,3,9-tetrahydrospiro[β-carboline-4,1'-cyclopropane]

Using the compound prepared in Example 39 (3) in place of the compound prepared in Example 36 (2), the same operation as in Example 38 was conducted to obtain the titled compound having the following physical properties.
TLC: Rf 0.44 (hexane:ethyl acetate=1:2);
$^1$H NMR (DMSO-d$_6$): δ 0.69-1.13 (m, 3H), 1.24-1.36 (m, 1H), 2.02-2.33 (m, 6H), 3.14 and 3.24 (d, J=13.4 Hz, 1H), 3.65 and 3.77 (d, J=13.4 Hz, 1H), 3.75 and 3.90 (s, 3H), 6.38 and 7.12 (s, 1H), 6.57-6.64 (m, 1H), 6.65-6.72 (m, 1H), 6.87 and 6.96 (s, 1H), 7.02-7.10 (m, 2H), 11.30 (s, 1H);
[α]$_D$=+157.1 (CHCl$_3$, c=0.12);
Description: solid.

Example 41 (6)

(+)-2-acetyl-5-chloro-1-(4-chloro-2-methoxyphenyl)-1,2,3,9-tetrahydrospiro[β-carboline-4,1'-cyclopropane]

Using the compound prepared in Example 36 (6) in place of the compound prepared in Example 36 (2), the same operation as in Example 38 was conducted to obtain the titled compound having the following physical properties.
TLC: Rf 0.51 (hexane:ethyl acetate=1:2);
$^1$H NMR (DMSO-d$_6$): δ 0.66-1.22 (m, 3H), 1.66-1.77 (m, 1H), 2.08 and 2.30 (s, 3H), 3.06-3.22 (m, 1H), 3.56-3.70 (m, 1H), 3.80 and 3.95 (s, 3H), 6.39 and 7.10 (s, 1H), 6.69-6.76 (m, 1 H), 6.91-6.99 (m, 1H), 7.00-7.06 (m, 2H), 7.14 and 7.23 (d, J=1.7 Hz, 1H), 7.23-7.30 (m, 1 H), 11.42 and 11.44 (s, 1H);
[α]$_D$=+166.0 (CHCl$_3$, c=0.14);
Description: solid.

Example 42 (1) to Example 42 (128)

It is possible to obtain the following compounds by conducting the same operation as in Example 27 or Example 38 using the respective racemic modifications described in the above Examples.

Example 42 (1): (+)-2-acetyl-1-(1,3-benzodioxol-5-yl)-1,2,3,9-tetrahydrospiro[β-carboline-4,1'-cyclopropane] and (−)-2-acetyl-1-(1,3-benzodioxol-5-yl)-1,2,3,9-tetrahydrospiro[β-carboline-4,1'-cyclopropane] (optical active material of the racemic modification described in Example 4)

Example 42 (2): (+)-1-(1,3-benzodioxol-5-yl)-N-(3,5-dimethylphenyl)-1,9-dihydrospiro[β-carboline-4,1'-cyclopropane]-2(3H)-carboxamide and (−)-1-(1,3-benzodioxol-5-yl)-N-(3,5-dimethylphenyl)-1,9-dihydrospiro[β-carboline-4,1'-cyclopropane]-2(3H)-carboxamide (optical active material of the racemic modification described in Example 5)

Example 42 (3): (+)-2-acetyl-1-(2,6-difluorophenyl)-1,2,3,9-tetrahydrospiro[β-carboline-4,1'-cyclopropane] and (−)-2-acetyl-1-(2,6-difluorophenyl)-1,2,3,9-tetrahydrospiro[β-carboline-4,1'-cyclopropane] (optical active material of the racemic modification described in Example 6 (1))

Example 42 (4): (+)-2-acetyl-1-(3,5-difluorophenyl)-1,2,3,9-tetrahydrospiro[β-carboline-4,1'-cyclopropane] and (−)-2-acetyl-1-(3,5-difluorophenyl)-1,2,3,9-tetrahydrospiro[β-carboline-4,1'-cyclopropane] (optical active material of the racemic modification described in Example 6 (2))

Example 42 (5): (+)-2-acetyl-1-(2,4-difluorophenyl)-1,2,3,9-tetrahydrospiro[β-carboline-4,1'-cyclopropane] and (−)-2-acetyl-1-(2,4-difluorophenyl)-1,2,3,9-tetrahydrospiro[β-carboline-4,1'-cyclopropane] (optical active material of the racemic modification described in Example 6 (3))

Example 42 (6): (+)-2-acetyl-1-(2,3-difluorophenyl)-1,2,3,9-tetrahydrospiro[β-carboline-4,1'-cyclopropane] and (−)-2-acetyl-1-(2,3-difluorophenyl)-1,2,3,9-tetrahydrospiro[β-carboline-4,1'-cyclopropane] (optical active material of the racemic modification described in Example 6 (4))

Example 42 (7): (+)-2-acetyl-1-(2,5-difluorophenyl)-1,2,3,9-tetrahydrospiro[β-carboline-4,1'-cyclopropane] and (−)-2-acetyl-1-(2,5-difluorophenyl)-1,2,3,9-tetrahydrospiro[β-carboline-4,1'-cyclopropane] (optical active material of the racemic modification described in Example 6 (5))

Example 42 (8): (+)-2-acetyl-1-(3,4-difluorophenyl)-1,2,3,9-tetrahydrospiro[β-carboline-4,1'-cyclopropane] and (−)-2-acetyl-1-(3,4-difluorophenyl)-1,2,3,9-tetrahydrospiro[β-carboline-4,1'-cyclopropane] (optical active material of the racemic modification described in Example 6 (6))

Example 42 (9): (+)-2-acetyl-6-chloro-1-(3-fluorophenyl)-1,2,3,9-tetrahydrospiro[β-carboline-4,1'-cyclopropane] and (−)-2-acetyl-6-chloro-1-(3-fluorophenyl)-1,2,3,9-tetrahydrospiro[β-carboline-4,1'-cyclopropane] (optical active material of the racemic modification described in Example 6 (7))

Example 42 (10): (+)-2-acetyl-1-(3-fluorophenyl)-6-methoxy-1,2,3,9-tetrahydrospiro[β-carboline-4,1'-cyclopropane] and (−)-2-acetyl-1-(3-fluorophenyl)-6-methoxy-1,2,3,9-tetrahydrospiro[β-carboline-4,1'-cyclopropane] (optical active material of the racemic modification described in Example 6 (8))

Example 42 (11): (+)-1-(3-fluorophenyl)-2-isobutyryl-1,2,3,9-tetrahydrospiro[β-carboline-4,1'-cyclopropane] and (−)-1-(3-fluorophenyl)-2-isobutyryl-1,2,3,9-tetrahydrospiro[β-carboline-4,1'-cyclopropane] (optical active material of the racemic modification described in Example 6 (9))

Example 42 (12): (+)-2-(cyclopropylcarbonyl)-1-(3-fluorophenyl)-1,2,3,9-tetrahydrospiro[β-carboline-4,1'-cyclopropane] and (−)-2-(cyclopropylcarbonyl)-1-(3-fluorophenyl)-1,2,3,9-tetrahydrospiro[β-carboline-4,1'-cyclopropane] (optical active material of the racemic modification described in Example 6 (10))

Example 42 (13): (+)-2-benzoyl-1-(3-fluorophenyl)-1,2,3,9-tetrahydrospiro[β-carboline-4,1'-cyclopropane] and (−)-2-benzoyl-1-(3-fluorophenyl)-1,2,3,9-tetrahydrospiro[β-carboline-4,1'-cyclopropane] (optical active material of the racemic modification described in Example 6 (11))

Example 42 (14): (+)-1-(3-fluorophenyl)-N,N-dimethyl-1,9-dihydrospiro[β-carboline-4,1'-cyclopropane]-2(3H)-carboxamide and (−)-1-(3-fluorophenyl)-N,N-dimethyl-1,9-dihydrospiro[β-carboline-4,1'-cyclopropane]-2(3H)-carboxamide (optical active material of the racemic modification described in Example 6 (12))

Example 42 (15): (+)-methyl 1-(3-fluorophenyl)-1,9-dihydrospiro[β-carboline-4,1'-cyclopropane]-2(3H)-carboxylate and (−)-methyl 1-(3-fluorophenyl)-1,9-dihydrospiro[β-carboline-4,1'-cyclopropane]-2(3H)-carboxylate (optical active material of the racemic modification described in Example 6 (13))

Example 42 (16): (+)-2-acetyl-1-(2,3-dihydro-1H-inden-5-yl)-1,2,3,9-tetrahydrospiro[β-carboline-4,1'-cyclopropane] and (−)-2-acetyl-1-(2,3-dihydro-1H-inden-5-yl)-1,2,3,9-tetrahydrospiro[β-carboline-4,1'-cyclopropane] (optical active material of the racemic modification described in Example 6 (14))

Example 42 (17): (+)-2-acetyl-6-fluoro-1-(3-fluorophenyl)-1,2,3,9-tetrahydrospiro[β-carboline-4,1'-cyclopropane] and (−)-2-acetyl-6-fluoro-1-(3-fluorophenyl)-1,2,3,9-tetrahydrospiro[β-carboline-4,1'-cyclopropane] (optical active material of the racemic modification described in Example 6 (15))

Example 42 (18): (+)-2-acetyl-1-(2,4-difluorophenyl)-6-fluoro-1,2,3,9-tetrahydrospiro[β-carboline-4,1'-cyclopropane] and (−)-2-acetyl-1-(2,4-difluorophenyl)-6-fluoro-1,2,3,9-tetrahydrospiro[β-carboline-4,1'-cyclopropane] (optical active material of the racemic modification described in Example 6 (16))

Example 42 (19): (+)-2-acetyl-1-(3,4-difluorophenyl)-6-fluoro-1,2,3,9-tetrahydrospiro[β-carboline-4,1'-cyclopropane] and (−)-2-acetyl-1-(3,4-difluorophenyl)-6-fluoro-1,2,3,9-tetrahydrospiro[β-carboline-4,1'-cyclopropane] (optical active material of the racemic modification described in Example 6 (17))

Example 42 (20): (+)-2-acetyl-1-(3-fluorophenyl)-7-methoxy-1,2,3,9-tetrahydrospiro[β-carboline-4,1'-cyclopropane] and (−)-2-acetyl-1-(3-fluorophenyl)-7-methoxy-1,2,3,9-tetrahydrospiro[β-carboline-4,1'-cyclopropane] (optical active material of the racemic modification described in Example 6 (18))

Example 42 (21): (+)-2-acetyl-7-fluoro-1-(3-fluorophenyl)-1,2,3,9-tetrahydrospiro[β-carboline-4,1'-cyclopropane] and (−)-2-acetyl-7-fluoro-1-(3-fluorophenyl)-1,2,3,9-tetrahydrospiro[β-carboline-4,1'-cyclopropane] (optical active material of the racemic modification described in Example 6 (19))

Example 42 (22): (+)-2-acetyl-1-(3-fluorophenyl)-5-methoxy-1,2,3,9-tetrahydrospiro[β-carboline-4,1'-cyclopropane] and (−)-2-acetyl-1-(3-fluorophenyl)-5-methoxy-1,2,3,9-tetrahydrospiro[β-carboline-4,1'-cyclopropane] (optical active material of the racemic modification described in Example 6 (20))

Example 42 (23): (+)-1-(2,6-difluorophenyl)-N-(3,5-dimethylphenyl)-1,9-dihydrospiro[β-carboline-4,1'-cyclopropane]-2(3H)-carboxamide and (−)-1-(2,6-difluorophenyl)-N-(3,5-dimethylphenyl)-1,9-dihydrospiro[β-carboline-4,1'-cyclopropane]-2(3H)-carboxamide (optical active material of the racemic modification described in Example 7 (1))

Example 42 (24): (+)-1-(3,5-difluorophenyl)-N-(3,5-dimethylphenyl)-1,9-dihydrospiro[β-carboline-4,1'-cyclopropane]-2(3H)-carboxamide and (−)-1-(3,5-difluorophenyl)-N-(3,5-dimethylphenyl)-1,9-dihydrospiro[β-carboline-4,1'-cyclopropane]-2(3H)-carboxamide (optical active material of the racemic modification described in Example 7 (2))

Example 42 (25): (+)-1-(2,4-difluorophenyl)-N-(3,5-dimethylphenyl)-1,9-dihydrospiro[β-carboline-4,1'-cyclopropane]-2(3H)-carboxamide and (−)-1-(2,4-difluorophenyl)-N-(3,5-dimethylphenyl)-1,9-dihydrospiro[β-carboline-4,1'-cyclopropane]-2(3H)-carboxamide (optical active material of the racemic modification described in Example 7 (3))

Example 42 (26): (+)-1-(2,3-difluorophenyl)-N-(3,5-dimethylphenyl)-1,9-dihydrospiro[β-carboline-4,1'-cyclopropane]-2(3H)-carboxamide and (−)-1-(2,3-difluorophenyl)-N-(3,5-dimethylphenyl)-1,9-dihydrospiro[β-carboline-4,1'-cyclopropane]-2(3H)-carboxamide (optical active material of the racemic modification described in Example 7 (4))

Example 42 (27): (+)-1-(2,5-difluorophenyl)-N-(3,5-dimethylphenyl)-1,9-dihydrospiro[β-carboline-4,1'-cyclopropane]-2(3H)-carboxamide and (−)-1-(2,5-difluorophenyl)-N-(3,5-dimethylphenyl)-1,9-dihydrospiro[β-carboline-4,1'-cyclopropane]-2(3H)-carboxamide (optical active material of the racemic modification described in Example 7 (5))

Example 42 (28): (+)-1-(3,4-difluorophenyl)-N-(3,5-dimethylphenyl)-1,9-dihydrospiro[β-carboline-4,1'-cyclopropane]-2(3H)-carboxamide and (−)-1-(3,4-difluorophenyl)-N-(3,5-dimethylphenyl)-1,9-dihydrospiro[β-carboline-4,1'-cyclopropane]-2(3H)-carboxamide (optical active material of the racemic modification described in Example 7 (6))

Example 42 (29): (+)-6-chloro-N-(3,5-dimethylphenyl)-1-(3-fluorophenyl)-1,9-dihydrospiro[β-carboline-4,1'-cyclopropane]-2(3H)-carboxamide and (−)-6-chloro-N-(3,5-dimethylphenyl)-1-(3-fluorophenyl)-1,9-dihydrospiro[β-carboline-4,1'-cyclopropane]-2(3H)-carboxamide (optical active material of the racemic modification described in Example 7 (7))

Example 42 (30): (+)—N-(3,5-dimethylphenyl)-1-(3-fluorophenyl)-6-methoxy-1,9-dihydrospiro[β-carboline-4,1'-cyclopropane]-2(3H)-carboxamide and (−)—N-(3,5-dimethylphenyl)-1-(3-fluorophenyl)-6-methoxy-1,9-dihydrospiro[β-carboline-4,1'-cyclopropane]-2(3H)-carboxamide ((optical active material of the racemic modification described in Example 7 (8))

Example 42 (31): (+)-1-(2,3-dihydro-1H-inden-5-yl)-N-(3,5-dimethylphenyl)-1,9-dihydrospiro[β-carboline-4,1'-cyclopropane]-2(3H)-carboxamide and (−)-1-(2,3-dihydro-1H-inden-5-yl)-N-(3,5-dimethylphenyl)-1,9-dihydrospiro[β-carboline-4,1'-cyclopropane]-2(3H)-carboxamide (optical active material of the racemic modification described in Example 7 (9))

Example 42 (32): (+)-2-acetyl-1-(3-fluorophenyl)-6,7-dimethoxy-1,2,3,9-tetrahydrospiro[β-carboline-4,1'-cyclopropane] and (−)-2-acetyl-1-(3-fluorophenyl)-6,7-dimethoxy-1,2,3,9-tetrahydrospiro[β-carboline-4,1'-cyclopropane] (optical active material of the racemic modification described in Example 7 (10))

Example 42 (33): (+)-2-acetyl-1-(2,4-difluorophenyl)-6,7-dimethoxy-1,2,3,9-tetrahydrospiro[β-carboline-4,1'-cyclopropane] and (−)-2-acetyl-1-(2,4-difluorophenyl)-6,7-dimethoxy-1,2,3,9-tetrahydrospiro[β-carboline-4,1'- cyclopropane] (optical active material of the racemic modification described in Example 7 (11))

Example 42 (34): (+)-2-acetyl-1-(2,4-difluorophenyl)-7-fluoro-1,2,3,9-tetrahydrospiro[β-carboline-4,1'-cyclopropane] and (−)-2-acetyl-1-(2,4-difluorophenyl)-7-fluoro-1,2,3,9-tetrahydrospiro[β-carboline-4,1'-cyclopropane] (optical active material of the racemic modification described in Example 7 (12))

Example 42 (35): (+)-2-acetyl-1-(3,4-difluorophenyl)-7-fluoro-1,2,3,9-tetrahydrospiro[β-carboline-4,1'-cyclopropane] and (−)-2-acetyl-1-(3,4-difluorophenyl)-7-fluoro-1,2,3,9-tetrahydrospiro[β-carboline-4,1'-cyclopropane] (optical active material of the racemic modification described in Example 7 (13))

Example 42 (36): (+)-2-acetyl-5-fluoro-1-(3-fluorophenyl)-1,2,3,9-tetrahydrospiro[β-carboline-4,1'-cyclopropane] and (−)-2-acetyl-5-fluoro-1-(3-fluorophenyl)-1,2,3,9-tetrahydrospiro[β-carboline-4,1'-cyclopropane] (optical active material of the racemic modification described in Example 7 (14))

Example 42 (37): (+)-2-acetyl-1-(2,4-difluorophenyl)-5-fluoro-1,2,3,9-tetrahydrospiro[β-carboline-4,1'-cyclopropane] and (−)-2-acetyl-1-(2,4-difluorophenyl)-5-fluoro-1,2,3,9-tetrahydrospiro[β-carboline-4,1'-cyclopropane] (optical active material of the racemic modification described in Example 7 (15))

Example 42 (38): (+)-2-acetyl-1-(3,4-difluorophenyl)-5-fluoro-1,2,3,9-tetrahydrospiro[β-carboline-4,1'-cyclopropane] and (−)-2-acetyl-1-(3,4-difluorophenyl)-5-fluoro-1,2,3,9-tetrahydrospiro[β-carboline-4,1'-cyclopropane] (optical active material of the racemic modification described in Example 7 (16))

Example 42 (39): (+)-2-acetyl-1-(3-fluorophenyl)-8-methoxy-1,2,3,9-tetrahydrospiro[β-carboline-4,1'-cyclopropane] and (−)-2-acetyl-1-(3-fluorophenyl)-8-methoxy-1,2,3,9-tetrahydrospiro[β-carboline-4,1'-cyclopropane] (optical active material of the racemic modification described in Example 7 (17))

Example 42 (40): (+)-2-acetyl-1-(2,4-difluorophenyl)-8-methoxy-1,2,3,9-tetrahydrospiro[β-carboline-4,1'-cyclopropane] and (−)-2-acetyl-1-(2,4-difluorophenyl)-8-methoxy-1,2,3,9-tetrahydrospiro[β-carboline-4,1'-cyclopropane] (optical active material of the racemic modification described in Example 7 (18))

Example 42 (41): (+)-2-acetyl-1-(3,4-difluorophenyl)-8-methoxy-1,2,3,9-tetrahydrospiro[β-carboline-4,1'-cyclopropane] and (−)-2-acetyl-1-(3,4-difluorophenyl)-8-methoxy-1,2,3,9-tetrahydrospiro[β-carboline-4,1'-cyclopropane] (optical active material of the racemic modification described in Example 7 (19))

Example 42 (42): (+)-2-acetyl-1-(3-fluorophenyl)-6,8-dimethoxy-1,2,3,9-tetrahydrospiro[β-carboline-4,1'-cyclopropane] and (−)-2-acetyl-1-(3-fluorophenyl)-6,8-dimethoxy-1,2,3,9-tetrahydrospiro[β-carboline-4,1'-cyclopropane] (optical active material of the racemic modification described in Example 7 (20))

Example 42 (43): (+)-2-acetyl-1-(3,4-difluorophenyl)-6,8-dimethoxy-1,2,3,9-tetrahydrospiro[β-carboline-4,1'-cyclopropane] and (−)-2-acetyl-1-(3,4-difluorophenyl)-6,8-dimethoxy-1,2,3,9-tetrahydrospiro[β-carboline-4,1'-cyclopropane] (optical active material of the racemic modification described in Example 7 (21))

Example 42 (44): (+)—N-(3,5-dimethylphenyl)-8-(3-methoxyphenyl)-5,6,8,9-tetrahydro-7H-pyrido[4',3':4,5]pyrrolo[2,3-b]pyridine-7-carboxamide and (−)-N-(3,5-dimethylphenyl)-8-(3-methoxyphenyl)-5,6,8,9-tetrahydro-7H-pyrido[4',3':4,5]pyrrolo[2,3-b]pyridine-7-carboxamide (optical active material of the racemic modification described in Example 11)

Example 42 (45): (+)7-acetyl-8-(3-methoxyphenyl)-6,7,8,9-tetrahydro-5H-pyrido[4',3':4,5]pyrrolo[2,3-b]pyridine and (−)-7-acetyl-8-(3-methoxyphenyl)-6,7,8,9-tetrahydro-5H-pyrido[4',3':4,5]pyrrolo[2,3-b]pyridine (optical active material of the racemic modification described in Example 12)

Example 42 (46): (+)-N-(3,5-dimethylphenyl)-8-(2-fluorophenyl)-5,6,8,9-tetrahydro-7H-pyrido[4',3':4,5]pyrrolo[2,3-b]pyridine-7-carboxamide and (−)-N-(3,5-dimethylphenyl)-8-(2-fluorophenyl)-5,6,8,9-tetrahydro-7H-pyrido[4',3':4,5]pyrrolo[2,3-b]pyridine (optical active material of the racemic modification described in Example 13 (1))

Example 42 (47): (+)-8-(3-fluorophenyl)-N-[2-(trifluoromethyl)phenyl]-5,6,8,9-tetrahydro-7H-pyrido[4',3':4,5]pyrrolo[2,3-b]pyridine-7-carboxamide and (−)-8-(3-fluorophenyl)-N-[2-(trifluoromethyl)phenyl]-5,6,8,9-tetrahydro-7H-pyrido[4',3':4,5]pyrrolo[2,3-b]pyridine-7-carboxamide (optical active material of the racemic modification described in Example 13 (2))

Example 42 (48): (+)-8-(3-fluorophenyl)-N-(3-methoxyphenyl)-5,6,8,9-tetrahydro-7H-pyrido[4',3':4,5]pyrrolo[2,3-b]pyridine-7-carboxamide and (−)-8-(3-fluorophenyl)-N-(3-methoxyphenyl)-5,6,8,9-tetrahydro-7H-pyrido[4',3':4,5]pyrrolo[2,3-b]pyridine-7-carboxamide (optical active material of the racemic modification described in Example 13 (3))

Example 42 (49): (+)-N-(3-chlorophenyl)-8-(3-fluorophenyl)-5,6,8,9-tetrahydro-7H-pyrido[4',3':4,5]pyrrolo[2,3-b]pyridine-7-carboxamide and (−)-N-(3-chlorophenyl)-8-(3-fluorophenyl)-5,6,8,9-tetrahydro-7H-pyrido[4',3':4,5]pyrrolo[2,3-b]pyridine-7-carboxamide (optical active material of the racemic modification described in Example 13 (4))

Example 42 (50): (+)-8-(1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide and (−)-8-(1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide (optical active material of the racemic modification described in Example 13 (5))

Example 42 (51): (+)-8-(3,5-difluorophenyl)-N-(3,5-dimethylphenyl)-5,6,8,9-tetrahydro-7H-pyrido[4',3':4,5]pyrrolo[2,3-b]pyridine-7-carboxamide and (−)-8-(3,5-difluorophenyl)-N-(3,5-dimethylphenyl)-5,6,8,9-tetrahydro-7H-pyrido[4',3':4,5]pyrrolo[2,3-b]pyridine-7-carboxamide (optical active material of the racemic modification described in Example 13 (6))

Example 42 (52): (+)-8-(2,2-difluoro-1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide and (−)-8-(2,2-difluoro-1,3-benzodioxol-5-yl)-N-(3,5-dimethylphenyl)-5,6,8,9-tetrahydro-7H-pyrido[4',3':4,5]pyrrolo[2,3-b]pyridine-7-carboxamide (optical active material of the racemic modification described in Example 13 (7))

Example 42 (53): (+)-N-(adamantane-1-yl)-8-(3-fluorophenyl)-5,6,8,9-tetrahydro-7H-pyrido[4',3':4,5]pyrrolo[2,3-b]pyridine-7-carboxamide and (−)-N-(adamantane-1-yl)-8-(3-fluorophenyl)-5,6,8,9-tetrahydro-7H-pyrido[4',3':4,5]pyrrolo[2,3-b]pyridine-7-carboxamide (optical active material of the racemic modification described in Example 13 (8))

Example 42 (54): (+)-8-(2,3-dihydro-1H-inden-5-yl)-N-(3,5-dimethylphenyl)-5,6,8,9-tetrahydro-7H-pyrido[4',3':4, 5]pyrrolo[2,3-b]pyridine-7-carboxamide and (−)-8-(2,3-dihydro-1H-inden-5-yl)-N-(3,5-dimethylphenyl)-5,6,8,9-tetrahydro-7H-pyrido[4',3':4,5]pyrrolo[2,3-b]pyridine-7-carboxamide (optical active material of the racemic modification described in Example 13 (9))

Example 42 (55): (+)-7-acetyl-8-(2-fluorophenyl)-6,7,8,9-tetrahydro-5H-pyrido[4',3':4,5]pyrrolo[2,3-b]pyridine and (−)-7-acetyl-8-(2-fluorophenyl)-6,7,8,9-tetrahydro-5H-pyrido[4',3:4,5]pyrrolo[2,3-b]pyridine (optical active material of the racemic modification described in Example 14 (1))

Example 42 (56): (+)-7-acetyl-8-(1,3-benzodioxol-5-yl)-6,7,8,9-tetrahydro-5H-pyrido[4',3':4,5]pyrrolo[2,3-b]pyridine and (−)-7-acetyl-8-(1,3-benzodioxol-5-yl)-6,7,8,9-tetrahydro-5H-pyrido[4',3:4,5]pyrrolo[2,3-b]pyridine (optical active material of the racemic modification described in Example 14 (2))

Example 42 (57): (+)-7-acetyl-8-(3,5-difluorophenyl)-6,7,8,9-tetrahydro-5H-pyrido[4',3':4,5]pyrrolo[2,3-b]pyridine and (−)-7-acetyl-8-(3,5-difluorophenyl)-6,7,8,9-tetrahydro-5H-pyrido[4',3:4,5]pyrrolo[2,3-b]pyridine (optical active material of the racemic modification described in Example 14 (3))

Example 42 (58): (+)-7-acetyl-8-(2,2-difluoro-1,3-benzodioxol-5-yl)-6,7,8,9-tetrahydro-5H-pyrido[4',3':4,5]pyrrolo[2,3-b]pyridine and (−)-7-acetyl-8-(2,2-difluoro-1,3-benzodioxol-5-yl)-6,7,8,9-tetrahydro-5H-pyrido[4',3':4,5]pyrrolo[2,3-b]pyridine (optical active material of the racemic modification described in Example 14 (4))

Example 42 (59): (+)-7-acetyl-8-(2,3-dihydro-1H-inden-5-yl)-6,7,8,9-tetrahydro-5H-pyrido[4',3':4,5]pyrrolo[2,3-b]pyridine and (−)-7-acetyl-8-(2,3-dihydro-1H-inden-5-yl)-6,7,8,9-tetrahydro-5H-pyrido[4',3:4,5]pyrrolo[2,3-b]pyridine (optical active material of the racemic modification described in Example 14 (5))

Example 42 (60): (+)-N-(3,5-dimethylphenyl)-8'-(3-fluorophenyl)-1',8'-dihydrospiro[cyclopropane-1,5'-pyrido[4',3':4,5]pyrrolo[2,3-b]pyridine]-7'(6'H)-carboxamide and (−)-N-(3,5-dimethylphenyl)-8'-(3-fluorophenyl)-1',8'-dihydrospiro[cyclopropane-1,5'-pyrido[4',3':4,5]pyrrolo[2,3-b]pyridine]-7'(6'H)-carboxamide (optical active material of the racemic modification described in Example 15)

Example 42 (61): (+)-7'-acetyl-8'-(3-fluorophenyl)-1',6',7',8'-tetrahydrospiro[cyclopropane-1,5'-pyrido[4',3':4,5]pyrrolo[2,3-b]pyridine] and (−)-7'-acetyl-8'-(3-fluorophenyl)-1',6',7',8'-tetrahydrospiro[cyclopropane-1,5'-pyrido[4',3':4,5]pyrrolo[2,3-b]pyridine] (optical active material of the racemic modification described in Example 16)

Example 42 (62): (+)-2-acetyl-1-(3-fluorophenyl)-9-methyl-1,2,3,9-tetrahydrospiro[β-carboline-4,1'-cyclopropane] and (−)-2-acetyl-1-(3-fluorophenyl)-9-methyl-1,2,3,9-tetrahydrospiro[β-carboline-4,1'-cyclopropane] (optical active material of the racemic modification described in Example 18 (1))

Example 42 (63): (+)-methyl 1-(3-fluorophenyl)-9-methyl-1,9-dihydrospiro[β-carboline-4,1'-cyclopropane]-2(3H)-carboxylate and (−)-methyl 1-(3-fluorophenyl)-9-methyl-1,9-dihydrospiro[β-carboline-4,1'-cyclopropane]-2(3H)-carboxylate (optical active material of the racemic modification described in Example 18 (2))

Example 42 (64): (+)-N-(3,5-dimethylphenyl)-8-(3-fluorophenyl)-9-methyl-5,6,8,9-tetrahydro-7H-pyrido[4',3':4,5]pyrrolo[2,3-b]pyridine-7-carboxamide and (−)-N-(3,5-dimethylphenyl)-8-(3-fluorophenyl)-9-methyl-5,6,8,9-tetrahydro-7H-pyrido[4',3':4,5]pyrrolo[2,3-b]pyridine-7-carboxamide (optical active material of the racemic modification described in Example 20 (1))

Example 42 (65): (+)-N-(3,5-dimethylphenyl)-8-(3-fluorophenyl)-1-methyl-1,5,6,8-tetrahydro-7H-pyrido[4',3':4,5]pyrrolo[2,3-b]pyridine-7-carboxamide and (−)-N-(3,5-dimethylphenyl)-8-(3-fluorophenyl)-1-methyl-1,5,6,8-tetrahydro-7H-pyrido[4',3':4,5]pyrrolo[2,3-b]pyridine-7-carboxamide (optical active material of the racemic modification described in Example 20 (2))

Example 42 (66): (+)-7-acetyl-8-(3-fluorophenyl)-9-methyl-6,7,8,9-tetrahydro-5H-pyrido[4',3':4,5]pyrrolo[2,3-b]pyridine and (−)-7-acetyl-8-(3-fluorophenyl)-9-methyl-6,7,8,9-tetrahydro-5H-pyrido[4',3':4,5]pyrrolo[2,3-b]pyridine (optical active material of the racemic modification described in Example 21)

Example 42 (67): (+)-N-(4,6-dimethylpyridin-2-yl)-8-(3-fluorophenyl)-5,6,8,9-tetrahydro-7H-pyrido[4',3':4,5]pyrrolo[2,3-b]pyridine-7-carboxamide and (−)-N-(4,6-dimethylpyridin-2-yl)-8-(3-fluorophenyl)-5,6,8,9-tetrahydro-7H-pyrido[4',3':4,5]pyrrolo[2,3-b]pyridine-7-carboxamide (optical active material of the racemic modification described in Example 22)

Example 42 (68): (+)-N-(2,2-difluoro-1,3-benzodioxol-5-yl)-8-(3-fluorophenyl)-5,6,8,9-tetrahydro-7H-pyrido[4',3':4,5]pyrrolo[2,3-b]pyridine-7-carboxamide and (−)-N-(2,2-difluoro-1,3-benzodioxol-5-yl)-8-(3-fluorophenyl)-5,6,8,9-tetrahydro-7H-pyrido[4',3':4,5]pyrrolo[2,3-b]pyridine-7-carboxamide (optical active material of the racemic modification described in Example 22 (1))

Example 42 (69): (+)-N-(3,5-dimethylphenyl)-6-(3-fluorophenyl)-5,6,8,9-tetrahydro-7H-pyrido[3',4':4,5]pyrrolo[2,3-c]pyridine-7-carboxamide and (−)-N-(3,5-dimethylphenyl)-6-(3-fluorophenyl)-5,6,8,9-tetrahydro-7H-pyrido[3',4':4,5]pyrrolo[2,3-c]pyridine-7-carboxamide (optical active material of the racemic modification described in Example 25)

Example 42 (70): (+)-7-acetyl-6-(3-fluorophenyl)-6,7,8,9-tetrahydro-5H-pyrido[3',4':4,5]pyrrolo[2,3-c]pyridine and (−)-7-acetyl-6-(3-fluorophenyl)-6,7,8,9-tetrahydro-5H-pyrido[3',4':4,5]pyrrolo[2,3-c]pyridine (optical active material of the racemic modification described in Example 26)

Example 42 (71): (+)-N-(3,5-dimethylphenyl)-8'-(3-fluorophenyl)-1'-methyl-1',8'-dihydrospiro[cyclopropane-1,5'-pyrido[4',3':4,5]pyrrolo[2,3-b]pyridine]-7'(6'H)-carboxamide and (−)-N-(3,5-dimethylphenyl)-8'-(3-fluorophenyl)-1'-methyl-1',8'-dihydrospiro[cyclopropane-1,5'-pyrido[4',3':4,5]pyrrolo[2,3-b]pyridine]-7'(6'H)-carboxamide (optical active material of the racemic modification described in Example 29)

Example 42 (72): (+)-7'-acetyl-8'-(3-fluorophenyl)-1'-methyl-1',6',7',8'-tetrahydrospiro[cyclopropane-1,5'-pyrido[4',3':4,5]pyrrolo[2,3-b]pyridine] and (−)-7'-acetyl-8'-(3-fluorophenyl)-1'-methyl-1',6',7',8'-tetrahydrospiro[cyclopropane-15'-pyrido[4',3':4,5]pyrrolo[2,3-b]pyridine] (optical active material of the racemic modification described in Example 29 (3))

Example 42 (73): (+)-N-(3,5-dimethylphenyl)-8-(3-methoxyphenyl)-1-methyl-1,5,6,8-tetrahydro-7H-pyrido[4',3':4,5]pyrrolo[2,3-b]pyridine-7-carboxamide and (−)-N-(3,5-dimethylphenyl)-8-(3-methoxyphenyl)-1-methyl-1,5,6,8-tetrahydro-7H-pyrido[4',3':4,5]pyrrolo[2,3-b]pyridine-7-carboxamide (optical active material of the racemic modification described in Example 29 (4))

Example 42 (74): (+)—N-(3,5-dimethylphenyl)-8-(2-fluorophenyl)-1-methyl-1,5,6,8-tetrahydro-7H-pyrido[4',3':4,5]pyrrolo[2,3-b]pyridine-7-carboxamide and (−)-N-(3,5-dimethylphenyl)-8-(2-fluorophenyl)-1-methyl-1,5,6,8-tetrahydro-7H-pyrido[4',3':4,5]pyrrolo[2,3-b]pyridine-7- carboxamide (optical active material of the racemic modification described in Example 29 (5))

Example 42 (75): (+)-8-(2,2-difluoro-1,3-benzodioxol-5-yl)-N-(3,5-dimethylphenyl)-1-methyl-1,5,6,8-tetrahydro-7H-pyrido[4',3':4,5]pyrrolo[2,3-b]pyridine-7-carboxamide and (−)-8-(2,2-difluoro-1,3-benzodioxol-5-yl)-N-(3,5-dimethylphenyl)-1-methyl-1,5,6,8-tetrahydro-7H-pyrido[4',3':4,5]pyrrolo[2,3-b]pyridine-7-carboxamide (optical active material of the racemic modification described in Example 29 (6))

Example 42 (76): (+)-N-(3,5-dimethylphenyl)-6-(3-fluorophenyl)-2-methoxy-5,6,8,9-tetrahydro-7H-pyrido[4',3':4,5]pyrrolo[3,2-b]pyridine-7-carboxamide and (−)-N-(3,5-dimethylphenyl)-6-(3-fluorophenyl)-2-methoxy-5,6,8,9-tetrahydro-7H-pyrido[4',3':4,5]pyrrolo[3,2-b]pyridine-7-carboxamide (optical active material of the racemic modification described in Example 31)

Example 42 (77): (+)-2-chloro-N-(3,5-dimethylphenyl)-6-(3-fluorophenyl)-5,6,8,9-tetrahydro-7H-pyrido[4',3':4,5]pyrrolo[3,2-b]pyridine-7-carboxamide and (−)-2-chloro-N-(3,5-dimethylphenyl)-6-(3-fluorophenyl)-5,6,8,9-tetrahydro-7H-pyrido[4',3':4,5]pyrrolo[3,2-b]pyridine-7-carboxamide (optical active material of the racemic modification described in Example 33 (1))

Example 42 (78): (+)-N-(3,5-dimethylphenyl)-6-(3-fluorophenyl)-5,6,8,9-tetrahydro-7H-pyrido[4',3':4,5]pyrrolo[3,2-b]pyridine-7-carboxamide and (−)-N-(3,5-dimethylphenyl)-6-(3-fluorophenyl)-5,6,8,9-tetrahydro-7H-pyrido[4',3':4,5]pyrrolo[3,2-b]pyridine-7-carboxamide (optical active material of the racemic modification described in Example 33 (2))

Example 42 (79): (+)-7-acetyl-6-(3-fluorophenyl)-2-methoxy-6,7,8,9-tetrahydro-5H-pyrido[4',3':4,5]pyrrolo[3,2-b]pyridine and (−)-7-acetyl-6-(3-fluorophenyl)-2-methoxy-6,7,8,9-tetrahydro-5H-pyrido[4',3':4,5]pyrrolo[3,2-b]pyridine (optical active material of the racemic modification described in Example 34 (1))

Example 42 (80): (+)-7-acetyl-2-chloro-6-(3-fluorophenyl)-6,7,8,9-tetrahydro-5H-pyrido[4',3':4,5]pyrrolo[3,2-b]pyridine and (−)-7-acetyl-2-chloro-6-(3-fluorophenyl)-6,7,8,9-tetrahydro-5H-pyrido[4',3':4,5]pyrrolo[3,2-b]pyridine (optical active material of the racemic modification described in Example 34 (2))

Example 42 (81): (+)-7-acetyl-6-(3-fluorophenyl)-6,7,8,9-tetrahydro-5H-pyrido[4',3':4,5]pyrrolo[3,2-b]pyridine and (−)-7-acetyl-6-(3-fluorophenyl)-6,7,8,9-tetrahydro-5H-pyrido[4',3':4,5]pyrrolo[3,2-b]pyridine (optical active material of the racemic modification described in Example 34 (3))

Example 42 (82): (+)-2-ethyl-1-(3-fluorophenyl)-1,2,3,9-tetrahydrospiro[β-carboline-4,1'-cyclopropane] and (−)-2-ethyl-1-(3-fluorophenyl)-1,2,3,9-tetrahydrospiro[β-carboline-4,1'-cyclopropane] (optical active material of the racemic modification described in Example 35)

Example 42 (83): (+)-2-acetyl-1-(4-chloro-2-methoxyphenyl)-1,2,3,9-tetrahydrospiro[β-carboline-4,1'-cyclopropane] and (−)-2-acetyl-1-(4-chloro-2-methoxyphenyl)-1,2,3,9-tetrahydrospiro[β-carboline-4,1'-cyclopropane] (optical active material of the racemic modification described in Example 36 (1))

Example 42 (84): (+)-2-acetyl-1-(4-chloro-2-methoxyphenyl)-5-fluoro-1,2,3,9-tetrahydrospiro[β-carboline-4,1'-cyclopropane] and (−)-2-acetyl-1-(4-chloro-2-methoxyphenyl)-5-fluoro-1,2,3,9-tetrahydrospiro[β-carboline-4,1'-cyclopropane] (optical active material of the racemic modification described in Example 36 (2))

Example 42 (85): (−)-2-acetyl-1-(4-chloro-2-methoxyphenyl)-6-fluoro-1,2,3,9-tetrahydrospiro[β-carboline-4,1'-cyclopropane] ((−) isomer of the racemic modification described in Example 36 (4))

Example 42 (86): (−)-2-acetyl-1-(4-chloro-2-methoxyphenyl)-5-methoxy-1,2,3,9-tetrahydrospiro[β-carboline-4,1'-cyclopropane] ((−) isomer of the racemic modification described in Example 36 (5))

Example 42 (87): (−)-2-acetyl-5-chloro-1-(4-chloro-2-methoxyphenyl)-1,2,3,9-tetrahydrospiro[β-carboline-4,1'-cyclopropane] ((−) isomer of the racemic modification described in Example 36 (6))

Example 42 (88): (+)-2-acetyl-5-chloro-1-(2-methoxy-4-methylphenyl)-1,2,3,9-tetrahydrospiro[β-carboline-4,1'-cyclopropane] and (−)-2-acetyl-5-chloro-1-(2-methoxy-4-methylphenyl)-1,2,3,9-tetrahydrospiro[β-carboline-4,1'-cyclopropane] (optical active material of the racemic modification described in Example 36 (7))

Example 42 (89): (−)-2-acetyl-5-fluoro-1-(2-fluoro-6-methoxyphenyl)-1,2,3,9-tetrahydrospiro[β-carboline-4,1'-cyclopropane] ((−) isomer of the racemic modification described in Example 37 (1))

Example 42 (90): (+)-2-acetyl-6-fluoro-1-(4-fluoro-2-methoxyphenyl)-1,2,3,9-tetrahydrospiro[β-carboline-4,1'-cyclopropane] and (−)-2-acetyl-6-fluoro-1-(4-fluoro-2-methoxyphenyl)-1,2,3,9-tetrahydrospiro[β-carboline-4,1'-cyclopropane] (optical active material of the racemic modification described in Example 37 (2))

Example 42 (91): (−)-2-acetyl-5-fluoro-1-(4-fluoro-2-methoxyphenyl)-1,2,3,9-tetrahydrospiro[β-carboline-4,1'-cyclopropane] ((−) isomer of the racemic modification described in Example 37 (3))

Example 42 (92): (+)-2-acetyl-1-(5-fluoro-2-methoxyphenyl)-5-methoxy-1,2,3,9-tetrahydrospiro[β-carboline-4,1'-cyclopropane] and (−)-2-acetyl-1-(5-fluoro-2-methoxyphenyl)-5-methoxy-1,2,3,9-tetrahydrospiro[β-carboline-4,1'-cyclopropane] (optical active material of the racemic modification described in Example 37 (4))

Example 42 (93): (+)-2-acetyl-1-(4-fluoro-2-methoxyphenyl)-5-methoxy-1,2,3,9-tetrahydrospiro[β-carboline-4,1'-cyclopropane] and (−)-2-acetyl-1-(4-fluoro-2-methoxyphenyl)-5-methoxy-1,2,3,9-tetrahydrospiro[β-carboline-4,1'-cyclopropane] (optical active material of the racemic modification described in Example 37 (5))

Example 42 (94): (+)-2-acetyl-1-(2,4-dimethoxyphenyl)-5-methoxy-1,2,3,9-tetrahydrospiro[β-carboline-4,1'-cyclopropane] and (−)-2-acetyl-1-(2,4-dimethoxyphenyl)-5-methoxy-1,2,3,9-tetrahydrospiro[β-carboline-4,1'-cyclopropane] (optical active material of the racemic modification described in Example 37 (6))

Example 42 (95): (−)-2-acetyl-1-(2-fluoro-6-methoxyphenyl)-5-methoxy-1,2,3,9-tetrahydrospiro[β-carboline-4,1'-cyclopropane] ((−) isomer of the racemic modification described in Example 37 (7))

Example 42 (96): (−)-2-acetyl-1-(4-chloro-2-methoxyphenyl)-6,7-dimethoxy-1,2,3,9-tetrahydrospiro[β-carboline-4,1'-cyclopropane] ((−) isomer of the racemic modification described in Example 37 (8))

Example 42 (97): (+)-2-acetyl-1-(2-methoxy-4-methylphenyl)-1,2,3,9-tetrahydrospiro[β-carboline-4,1'-cyclopropane] and (−)-2-acetyl-1-(2-methoxy-4-methylphenyl)-1,2,3,9-tetrahydrospiro[β-carboline-4,1'-cyclopropane] (optical active material of the racemic modification described in Example 37 (9))

Example 42 (98): (+)-2-acetyl-5-fluoro-1-(2-methoxy-4-methylphenyl)-1,2,3,9-tetrahydrospiro[β-carboline-4,1'-cyclopropane] and (−)-2-acetyl-5-fluoro-1-(2-methoxy-4- methylphenyl)-1,2,3,9-tetrahydrospiro[β-carboline-4,1'-cyclopropane] (optical active material of the racemic modification described in Example 37 (10))

Example 42 (99): (+)-2-acetyl-1-(4-chloro-2-methoxyphenyl)-6-methoxy-1,2,3,9-tetrahydrospiro[β-carboline-4,1'-cyclopropane] and (−)-2-acetyl-1-(4-chloro-2-methoxyphenyl)-6-methoxy-1,2,3,9-tetrahydrospiro[β-carboline-4,1'-cyclopropane] (optical active material of the racemic modification described in Example 37 (11))

Example 42 (100): (+)-2-acetyl-1-(4-fluoro-2-methoxyphenyl)-6-methoxy-1,2,3,9-tetrahydrospiro[β-carboline-4,1'-cyclopropane] and (−)-2-acetyl-1-(4-fluoro-2-methoxyphenyl)-6-methoxy-1,2,3,9-tetrahydrospiro[β-carboline-4,1'-cyclopropane] (optical active material of the racemic modification described in Example 37 (12))

Example 42 (101): (+)-2-acetyl-6-methoxy-1-(2-methoxy-4-methylphenyl)-1,2,3,9-tetrahydrospiro[β-carboline-4,1'-cyclopropane] and (−)-2-acetyl-6-methoxy-1-(2-methoxy-4-methylphenyl)-1,2,3,9-tetrahydrospiro[β-carboline-4,1'-cyclopropane] (optical active material of the racemic modification described in Example 37 (13))

Example 42 (102): (−)-2-acetyl-1-(2-fluoro-6-methoxyphenyl)-6-methoxy-1,2,3,9-tetrahydrospiro[β-carboline-4,1'-cyclopropane] ((−) isomer of the racemic modification described in Example 37 (14))

Example 42 (103): (+)-2-acetyl-6,7-dimethoxy-1-(2-methoxy-4-methylphenyl)-1,2,3,9-tetrahydrospiro[β-carboline-4,1'-cyclopropane] and (−)-2-acetyl-6,7-dimethoxy-1-(2-methoxy-4-methylphenyl)-1,2,3,9-tetrahydrospiro[β-carboline-4,1'-cyclopropane] (optical active material of the racemic modification described in Example 37 (15))

Example 42 (104): (+)-2-acetyl-1-(4-chloro-2-methoxyphenyl)-5-methyl-1,2,3,9-tetrahydrospiro[β-carboline-4,1'-cyclopropane] and (−)-2-acetyl-1-(4-chloro-2-methoxyphenyl)-5-methyl-1,2,3,9-tetrahydrospiro[β-carboline-4,1'-cyclopropane] (optical active material of the racemic modification described in Example 37 (16))

Example 42 (105): (−)-2-acetyl-1-(2-methoxy-4-methylphenyl)-5-methyl-1,2,3,9-tetrahydrospiro[β-carboline-4,1'-cyclopropane] ((−) isomer of the racemic modification described in Example 37 (17))

Example 42 (106): (+)-2-acetyl-1-(2,3-dihydro-1-benzofuran-7-yl)-6-methoxy-1,2,3,9-tetrahydrospiro[β-carboline-4,1'-cyclopropane] and (−)-2-acetyl-1-(2,3-dihydro-1-benzofuran-7-yl)-6-methoxy-1,2,3,9-tetrahydrospiro[β-carboline-4,1'-cyclopropane] (optical active material of the racemic modification described in Example 37 (18))

Example 42 (107): (−)-2-acetyl-1-(4-chloro-2-methoxyphenyl)-6-methoxy-5-methyl-1,2,3,9-tetrahydrospiro[β-carboline-4,1'-cyclopropane] ((−) isomer of the racemic modification described in Example 37 (19))

Example 42 (108): (+)-2-acetyl-5-fluoro-1-(2-methoxyphenyl)-1,2,3,9-tetrahydrospiro[β-carboline-4,1'-cyclopropane] and (−)-2-acetyl-5-fluoro-1-(2-methoxyphenyl)-1,2,3,9-tetrahydrospiro[β-carboline-4,1'-cyclopropane] (optical active material of the racemic modification described in Example 37 (20))

Example 42 (109): (+)-2-acetyl-1-(4-chloro-2-methoxyphenyl)-5,6-dimethoxy-1,2,3,9-tetrahydrospiro[β-carboline-4,1'-cyclopropane] and (−)-2-acetyl-1-(4-chloro-2-methoxyphenyl)-5,6-dimethoxy-1,2,3,9-tetrahydrospiro[β-carboline-4,1'-cyclopropane] (optical active material of the racemic modification described in Example 37 (21))

Example 42 (110): (+)-2-acetyl-5-chloro-1-(4-fluoro-2-methoxyphenyl)-1,2,3,9-tetrahydrospiro[1-carboline-4,1'-cyclopropane] and (−)-2-acetyl-5-chloro-1-(4-fluoro-2-methoxyphenyl)-1,2,3,9-tetrahydrospiro[β-carboline-4,1'-cyclopropane] (optical active material of the racemic modification described in Example 39 (1))

Example 42 (111): (+)-2-acetyl-5,6-difluoro-1-(4-fluoro-2-methoxyphenyl)-1,2,3,9-tetrahydrospiro[β-carboline-4,1'-cyclopropane] and (−)-2-acetyl-5,6-difluoro-1-(4-fluoro-2-methoxyphenyl)-1,2,3,9-tetrahydrospiro[β-carboline-4,1'-cyclopropane] (optical active material of the racemic modification described in Example 39 (2))

Example 42 (112): (−)-2-acetyl-5,6-difluoro-1-(2-methoxy-4-methylphenyl)-1,2,3,9-tetrahydrospiro[β-carboline-4,1'-cyclopropane] ((−) isomer of the racemic modification described in Example 39 (3))

Example 42 (113): (+)-2-acetyl-5-chloro-1-(2-fluoro-6-methoxyphenyl)-1,2,3,9-tetrahydrospiro[1-carboline-4,1'-cyclopropane] and (−)-2-acetyl-5-chloro-1-(2-fluoro-6-methoxyphenyl)-1,2,3,9-tetrahydrospiro[β-carboline-4,1'-cyclopropane] (optical active material of the racemic modification described in Example 39 (4))

Example 42 (114): (+)-2-acetyl-1-(4-chloro-2-isopropoxyphenyl)-1,2,3,9-tetrahydrospiro[β-carboline-4,1'-cyclopropane] and (−)-2-acetyl-1-(4-chloro-2-isopropoxyphenyl)-1,2,3,9-tetrahydrospiro[β-carboline-4,1'-cyclopropane] (optical active material of the racemic modification described in Example 39 (5))

Example 42 (115): (+)-2-acetyl-1-[4-chloro-2-(cyclopentyloxy)phenyl]-1,2,3,9-tetrahydrospiro[β-carboline-4,1'-cyclopropane] and (−)-2-acetyl-1-[4-chloro-2-(cyclopentyloxy)phenyl]-1,2,3,9-tetrahydrospiro[β-carboline-4,1'-cyclopropane] (optical active material of the racemic modification described in Example 39 (6))

Example 42 (116): (+)-4-(2-acetyl-1,2,3,9-tetrahydrospiro[β-carboline-4,1'-cyclopropane]-1-yl)-3-methoxybenzonitrile and (−)-4-(2-acetyl-1,2,3,9-tetrahydrospiro[β-carboline-4,1'-cyclopropane]-1-yl)-3-methoxybenzonitrile (optical active material of the racemic modification described in Example 39 (7))

Example 42 (117): (+)-2-acetyl-1-(4-chloro-2-methoxyphenyl)-5,7-difluoro-1,2,3,9-tetrahydrospiro[β-carboline-4,1'-cyclopropane] and (−)-2-acetyl-1-(4-chloro-2-methoxyphenyl)-5,7-difluoro-1,2,3,9-tetrahydrospiro[β-carboline-4,1'-cyclopropane] (optical active material of the racemic modification described in Example 39 (8))

Example 42 (118): (+)-2-acetyl-1-(4-chloro-2-methoxyphenyl)-8-fluoro-1,2,3,9-tetrahydrospiro[β-carboline-4,1'-cyclopropane] and (−)-2-acetyl-1-(4-chloro-2-methoxyphenyl)-8-fluoro-1,2,3,9-tetrahydrospiro[β-carboline-4,1'-cyclopropane] (optical active material of the racemic modification described in Example 39 (9))

Example 42 (119): (+)-4-(2-acetyl-5-fluoro-1,2,3,9-tetrahydrospiro[β-carboline-4,1'-cyclopropane]-1-yl)-3-methoxybenzonitrile and (−)-4-(2-acetyl-5-fluoro-1,2,3,9-tetrahydrospiro[β-carboline-4,1'-cyclopropane]-1-yl)-3-methoxybenzonitrile (optical active material of the racemic modification described in Example 39 (10))

Example 42 (120): (+)-2-acetyl-5,6-dimethoxy-1-(2-methoxy-4-methylphenyl)-1,2,3,9-tetrahydrospiro[β-carboline-4,1'-cyclopropane] and (−)-2-acetyl-5,6-dimethoxy-1-(2-methoxy-4-methylphenyl)-1,2,3,9-tetrahydrospiro[β-carboline-4,1'-cyclopropane] (optical active material of the racemic modification described in Example 40 (1))

Example 42 (121): (+)-2-acetyl-5-methoxy-1-(2-methoxyphenyl)-1,2,3,9-tetrahydrospiro[β-carboline-4,1'-cyclopropane] and (−)-2-acetyl-5-methoxy-1-(2-methoxyphenyl)-1,2,3,9-tetrahydrospiro[β-carboline-4,1'-cyclopropane] (optical active material of the racemic modification described in Example 40 (2))

Example 42 (122): (+)-4-(2-acetyl-5-methoxy-1,2,3,9-tetrahydrospiro[β-carboline-4,1'-cyclopropane]-1-yl)benzonitrile and (−)-4-(2-acetyl-5-methoxy-1,2,3,9-tetrahydrospiro[β-carboline-4,1'-cyclopropane]-1-yl) benzonitrile (optical active material of the racemic modification described in Example 40 (3))

Example 42 (123): (+)-2-acetyl-1-(2,3-dihydro-1-benzofuran-7-yl)-5-methoxy-1,2,3,9-tetrahydrospiro[β-carboline-4,1'-cyclopropane] and (−)-2-acetyl-1-(2,3-dihydro-1-benzofuran-7-yl)-5-methoxy-1,2,3,9-tetrahydrospiro[β-carboline-4,1'-cyclopropane] (optical active material of the racemic modification described in Example 40 (4))

Example 42 (124): (+)-2-acetyl-5-methoxy-1-(2-methoxy-4-methylphenyl)-1,2,3,9-tetrahydrospiro[β-carboline-4,1'-cyclopropane] and (−)-2-acetyl-5-methoxy-1-(2-methoxy-4-methylphenyl)-1,2,3,9-tetrahydrospiro[β-carboline-4,1'-cyclopropane] (optical active material of the racemic modification described in Example 40 (5))

Example 42 (125): (+)-2-acetyl-1-(4-chloro-2-methoxyphenyl)-6,8-dimethoxy-1,2,3,9-tetrahydrospiro[β-carboline-4,1'-cyclopropane] and (−)-2-acetyl-1-(4-chloro-2-methoxyphenyl)-6,8-dimethoxy-1,2,3,9-tetrahydrospiro[β-carboline-4,1'-cyclopropane] (optical active material of the racemic modification described in Example 40 (6))

Example 42 (126): (+)-2-acetyl-6-chloro-1-(4-chloro-2-methoxyphenyl)-1,2,3,9-tetrahydrospiro[β-carboline-4,1'-cyclopropane] and (−)-2-acetyl-6-chloro-1-(4-chloro-2-methoxyphenyl)-1,2,3,9-tetrahydrospiro[β-carboline-4,1'-cyclopropane] (optical active material of the racemic modification described in Example 40 (7))

Example 42 (127): (+)-2-acetyl-1-(4-chloro-2-methoxyphenyl)-5-fluoro-8-methoxy-1,2,3,9-tetrahydrospiro[β-carboline-4,1'-cyclopropane] and (−)-2-acetyl-1-(4-chloro-2-methoxyphenyl)-5-fluoro-8-methoxy-1,2,3,9-tetrahydrospiro[β-carboline-4,1'-cyclopropane] (optical active material of the racemic modification described in Example 40 (8))

Example 42 (128): (+)-2-acetyl-5-fluoro-1-(4-fluoro-2-methoxyphenyl)-8-methoxy-1,2,3,9-tetrahydrospiro[β-carboline-4,1'-cyclopropane] and (−)-2-acetyl-5-fluoro-1-(4-fluoro-2-methoxyphenyl)-8-methoxy-1,2,3,9-tetrahydrospiro[β-carboline-4,1'-cyclopropane] (optical active material of the racemic modification described in Example 40 (9))

BIOLOGICAL EXAMPLES

It was proved by the following experiments that the compound of the present invention has the effect of the present invention, particularly an antistress effect. The methods for experiments will be shown below, but are not limited thereto. PK11195 described in the following Examples is described in Eur. J. Pharmacol., 119, pp. 153-167, 1985 as an MBR selective ligand (1-(2-chlorophenyl)-N-methyl-N-(1-methylpropyl)-3-isoquinolinecarboxamide). Also, CB34 is described in British Journal of Pharmacology, 127, pp. 177-187, 1999 as an MBR selective agonist [5,7-dichloro-2-(4-chlorophenyl)-3-dipropylaminocarbonylimidazo[1,2-a]pyridine.

Biological Example 1

Receptor Binding Experiment

Affinity of the compound of the present invention for MBR was measured using a rat membrana cerebri specimen. The measuring method of the present invention has improved measurement accuracy and measurement sensitivity so as to evaluate the compound of the present invention as follows. A Wistar male rat was decapitated and the whole brain was extirpated, and then the cerebellum was removed. For the rat membrana cerebri specimen used in the binding experiment, 50 mmol/L of an ice-cold tris-hydrochloric acid buffer (pH 7.4) was added and it was homogenized and centrifuged. After the resulting deposit was washed, it was resuspended to be prepared to about 1 mg/ml. The binding experiment was conducted using [$^3$H]PK11195 as an MBR selective ligand.

In the case of calculating the all binding amount in a saturation experiment, the membrane specimen, [$^3$H]PK11195 at several concentrations, dimethyl sulfoxide (DMSO) in a final concentration of 0.5 vol %, and 50 mmol/L of a tris-hydrochloric acid buffer (pH 7.4) were mixed (all amount 200 μl), followed by incubation at room temperature for one hour. In the case of calculating the nonspecific binding amount, [$^3$H]PK11195 in a final concentration of 20 μmol/L was added instead of DMSO, followed by incubation for one hour. They were rapidly filtered on a GF/B filter pretreated with 0.3% polyethylenimine using a harvester, and washed with 50 mmol/L of a tris-hydrochloric acid buffer (pH 7.4) twice. After the filter was dried, radioactivity was measured by a liquid scintillation counter. With respect to the data obtained in the binding experiment, a Scatchard analysis was performed using analysis software KELL (Ver. 6 BIOSOFT) to calculate a dissociation constant ($K_D$ value).

In the case of calculating the all binding amount in a competition experiment, the membrane specimen, [$^3$H]PK11195 in a final concentration of 0.5 or 1 nmol/L, DMSO in a final concentration of 0.5 vol %, and 50 mmol/L of a tris-hydrochloric acid buffer (pH 7.4) were mixed (all amount 200 μl), followed by incubation at room temperature for one hour. In the case of calculating the nonspecific binding amount, PK11195 in a final concentration of 20 μmol/L instead of DMSO was added, followed by incubation. In the case of calculating the affinity of the compound of the present invention, a DMSO solution of the present invention in a final concentration of 10 pmol/L to 1 μmol/L instead of DMSO was added, followed by incubation. One hour later, they were sucking filtered in the above method, and the radioactivity on the filter was measured with a liquid scintillation counter. From the obtained data, the concentration of the compound of the present invention ($IC_{50}$ value) needed to inhibit the specific binding amount of [$^3$H]PK11195 by 50% was calculated. An inhibition constant ($K_i$ value) was calculated using a $K_D$ value and an $IC_{50}$ value according to the formula of Cheng and Prusoff (Biochem. Pharmacol. 1973; 22: pp. 3099-3108).

As a result, it was revealed that the compound of the present invention had high affinity to MBR.

For example, a $K_i$ value of the compound of Example 38 was 0.08 nM.

Biological Example 2

Study on Antistress Effect (1)

Psychological stressor was loaded using a Wistar male rat (Brain Res. 1994; 641: pp. 21-28). Water was accumulated by the depth of about 10 cm in a container having a platform in the center. Thirty-minutes after a medium or the compound of the present invention (the compound of Example 38) was intravenously administered at a dose of 0.01 mg/kg or orally administered at a dose of 1 mg/kg, stressor loading was initiated, and one hour later, the number of dejection was counted (10 animals in each group). The rat administered the compound of the present invention and the rat to which the stressor was not loaded had little dejection after one hour. On the other hand, it was revealed that the medium treatment group to which the stressor was loaded showed remarkable dejection (the number of dejection: mean number 10.5 by intravenous administration, and mean number 8.5 by oral administration), while the compound of the present invention significantly inhibited the number of dejection than the medium treatment group (the number of dejection: mean number 8.2 by intravenous administration and mean number 6.2 by oral administration).

As a result, it was found that the compound of the present invention had an antistress effect.

Biological Example 3

Study on Antistress Effect (2)

Physical stressor was loaded using a male Sprague-Dawley (SD) rat (CHARLES RIVER LABORATORIES JAPAN, INC., 7 week old at being used) (Gastroenterology 1988; 94: pp. 611-622; Jpn. J. Phrmacol. 1998; 77: pp. 211-217). Thirty minutes after a medium (0.5% Tween 80 physiological saline) or the compound of the present invention (the compound of Example 38) was orally administered at a dose of 1 mg/kg, stressor loading was initiated by restraining both anterior branches of the rat with a binding band (Marvel Ltd.). Evaluation was performed by measuring the number of dejection 30 and 60 minutes after the initiation of stressor loading (15 animals in each group). It was revealed that the medium treatment group loaded the stressor showed remarkable dejection (the number of dejection: mean number 10.1 (60 minutes after)), while the compound of the present invention significantly inhibited the number of dejection than the medium treatment group (the number of dejection: mean number 7.5 (60 minutes after)).

As a result, it was found that the compound of the present invention had an antistress effect.

Biological Example 4

Oral Absorbability of Rat

Using a fasted SD male rat (CHARLES RIVER LABORATORIES JAPAN, INC.), under the condition that the compound of the present invention (the compound of Example 38) was solubilized, the plasma concentration after administration in the tail vein at a dose of 0.1 mg/kg and the plasma concentration after gastric gavage administration at a dose of 1 mg/kg were measured. The blood was collected from a rat jugular vein under an unanesthetized condition 5, 15, and 30 minutes, and 1, 2, 3, 4, 6, and 8 hours after intravenous administration, and 15 and 30 minutes, and 1, 2, 3, 4, 6, and 8 hours after oral administration. Then the blood was centrifuged at 3000 rpm for 10 minutes and the supernatant was collected as plasma. The concentration of the compound in plasma was measured with LC/MS/MS (1100 HPLC System (Agilent Co. Ltd.), API 4000 (MDS SCIEX Ltd.)). From the obtained plasma concentration, an area under the curve (AUC, ng·h/ml) and a maximum plasma concentration ($C_{max}$, ng/mL) were calculated. In addition, Bioavailability (B.A.) of the compound of the present invention was calculated from AUC in oral administration and AUC in intravenous administration.

As a result, it was found that the compound of the present invention showed B.A. of 86.9% and is excellent in oral absorbability.

Biological Example 5

Competition Experiment of MBR Ligand

Using a Wistar male rat, psychological stressor similar to that in Biological Example 2 described above was loaded. Each treatment group was set as follows: a medium was intravenously administered (treatment group 1), the compound of the present invention (the compound of Example 38) was intravenously administered at a dose of 0.1 mg/kg (treatment group 2), an MBR selective agonist (CB34) was intravenously administered at a dose of 1 mg/kg (treatment group 3), or after the compound of the present invention (the compound of Example 38) was intravenously administered at a dose of 0.1 mg/kg, an MBR selective agonist was intravenously administered at a dose of 0.1 mg/kg (treatment group 4). In each group, stressor loading was initiated 10 minutes after administration, and the number of dejection was counted one hour later (10 animals in each group). The rats in the treatment groups 1, 3, and 4 showed remarkable dejection (the number of dejection: treatment group 1 (mean number 10.9), treatment group 3 (mean number 9.5), treatment group 4 (mean number 10.1)), while the number of dejection was inhibited in the rat in the treatment group 2 (the number of dejection: mean number 7.3). From this result, it was revealed that the effect observed in single administration of the compound of the present invention was reduced by administration of the MBR selective agonist.

As a result, it was speculated that the compound of the present invention expressed an antistress effect since it had an MBR antagonism.

Biological Example 6

Study on Inhibitory Action on Abdominal Pain in RCS Loading Model

A Wistar male rat (6 week old at being received) was anesthetized with pentobarbital sodium (Kyoritsu Seiyaku Corporation), its abdomen was incised and the abdominal muscle was exposed, and then Force Transducer (F-12IS-SL (STAR MEDICAL Ltd.)) was fitted. Penicillin was intramuscular administered after the operation, and a recuperative period of 5 days was set.

During from AM 9:00 to PM 5:00 on a $1^{st}$ day of the initiation of stress loading, the feeding environment temperature was alternately changed to 24° C. and 2° C. in an hour interval, and during from PM 5:00 to AM 9:00 in the next morning, the rat was fed under the environment of 2° C. From a $2^{nd}$ day to a $4^{th}$ day, during AM 9:00 to PM 6:00, the feeding environment temperature was alternately changed to 24° C. and 2° C. in an hour interval, and during PM 6:00 to AM 9:00 in the next morning, the rat was fed under the environment of 2° C. and Repeated cold stress (RCS) was loaded. A medium or the compound of the present invention (the compound of Example 38) was orally administered twice a day at a dose of 1 mg/kg. For the animal to which RCS was not loaded (non-stress loaded rat), a medium was administered.

After RCS was loaded for 4 days, abdominal pain evaluation was performed on a $5^{th}$ day (10 to 12 animals in each group). At evaluating abdominal pain, the stress loaded rat and the nonstress loaded rat received only an indwelling operation were put in a measuring cage, and a balloon (Fogarty catheter 6F (Baxter Ltd.)) was inserted by about 3 cm into the rectum from the anus and fixed. After confirming that abdominal exercise was stable, the liquid amount in the balloon was stepwisely increased to 0, 0.3, 0.6, 0.9, and 1.2 mL in 5 minutes interval. Contraction of abdominal muscle for extension stimulation in each balloon liquid amount was recorded using the Chart software (Chart v5.0.2. (ADInstruments Inc.)) by passing the signal from the pressure transducer amplified by the amplifier (Windo Gragf (GOULD Inc.)) through the data collection system (PowerLab (ADInstruments Inc.)). During 5 minutes in which balloon extension stimulation was loaded, the number of signals from the pressure transducer in 3 minutes was counted, and the obtained number was regarded as the number of abdominal muscle contraction and set as the index of abdominal pain. As shown in FIG. 1, for the number of abdominal muscle contraction increased as compared to the nonstress loaded rat in the medium treatment group, the compound of the present invention significantly inhibited the number of abdominal muscle contraction in all balloon capacities.

As a result, it was found that the compound of the present invention had an inhibitory action on abdominal pain induced by stress.

Preparation Example 1

The following respective components were mixed by a conventional method and then compressed into tablets to obtain 10,000 tablets each containing 10 mg of an active ingredient.
(1S)-2-acetyl-1-(4-chloro-2-methoxyphenyl)-5-fluoro-1,2,3,9-tetrahydrospiro[β-carboline-4,1'-cyclopropane] (100 g)
Carboxymethylcellulose calcium (disintegrant) (20.0 g)
Magnesium stearate (lubricant) (10.0 g)
Microcrystalline cellulose (870 g)

Preparation Example 2

The following respective components were mixed by a conventional method, the mixture was filtered by a dust removing filter, filled in an ampule in 5 ml each, and then heat-sterilized using an autoclave to obtain 10,000 ampules each containing 20 mg of an active ingredient.
(1S)-2-acetyl-1-(4-chloro-2-methoxyphenyl)-5-fluoro-1,2,3,9-tetrahydrospiro[β-carboline-4,1'-cyclopropane] (200 g)
Mannitol (2 kg)
Distilled water (50 L)

INDUSTRIAL APPLICABILITY

The compound of the present invention represented by the general formula (I) has affinity for MBR and has an antistress effect, and is therefore useful as a preventive and/or therapeutic medicine for diseases caused by stress, particularly digestive system disorders caused by stress.

The invention claimed is:
1. A compound of (1S)-2-acetyl-1-(4-chloro-2-methoxyphenyl)-5-fluoro-1,2,3,9-tetrahydrospiro [beta-carboline-4-1'-cyclopropane], a salt thereof, or an N-oxide thereof.
2. A compound of (1S)-2-acetyl-1-(4-chloro-2-methoxyphenyl)-5-fluoro-1,2,3,9-tetrahydrospiro[beta-carboline-4-1'-cyclopropane].

* * * * *